(12) United States Patent
Ali et al.

(10) Patent No.: US 7,947,664 B2
(45) Date of Patent: May 24, 2011

(54) ANGIOTENSIN II RECEPTOR ANTAGONISTS

(75) Inventors: Amjad Ali, Freehold, NJ (US); Michael Man-Chu Lo, Edison, NJ (US); Christopher Franklin, Quincy, NJ (US); Brent R. Whitehead, Piscataway, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/812,547

(22) PCT Filed: Jan. 8, 2009

(86) PCT No.: PCT/US2009/030382
§ 371 (c)(1),
(2), (4) Date: Jul. 12, 2010

(87) PCT Pub. No.: WO2009/094242
PCT Pub. Date: Jul. 30, 2009

(65) Prior Publication Data
US 2010/0292192 A1 Nov. 18, 2010

Related U.S. Application Data

(60) Provisional application No. 61/062,267, filed on Jan. 24, 2008.

(51) Int. Cl.
*C07D 257/04* (2006.01)
*A01N 57/00* (2006.01)
(52) U.S. Cl. ......................................... 514/92; 548/250
(58) Field of Classification Search ........................ None
See application file for complete search history.

(56) References Cited

U.S. PATENT DOCUMENTS 5,138,069 A  8/1992  Carini et al.
5,366,997 A  11/1994  Keefer et al.

FOREIGN PATENT DOCUMENTS
WO    WO2009/099853    *  8/2009

OTHER PUBLICATIONS

AngiotensinIIReceptorAntagonist, http://en.wikipedia.org/wiki/Angiotensin_II_receptor_antagonist, 2010.*
US International Search Report; completed Feb. 24, 2009; Performed by Authorized Officer Lee W. Young.

* cited by examiner

*Primary Examiner* — Sun Jae Y Loewe
(74) *Attorney, Agent, or Firm* — Mark R. Daniel; Richard S. Parr

(57) ABSTRACT

A compound having the structure $$R-Y$$
$$|$$
$$[Y]_{0-1}$$

wherein R is an angiotensin receptor antagonist active group, Y is selected from the group consisting of 1)
$$-C(R^1H)OC(O)OCH_2-\underset{1-4}{\underbrace{\phantom{XXX}}}-R^5,$$

and
2)  $-C(R^1H)OC(O)X((CR^{12}R^{13})-(CHR^{10})_m-(CH_2)_n-Z_p-(CH_2)_q-(CHR^{11})_r-(CR^{16}R^{17}))-R^5$;
Z is $-O-$ or $-(CR^{14}R^{15})-$;
m, n, p, q, and r are independently selected from the group consisting of 0 and 1;
X is $-O-$ or $-(CR^{18}R^{19})-$;
$R^1$ is selected from the group consisting of hydrogen, $C_{1-4}$ alkyl, aryl and $C_{1-4}$ alkylaryl;
$R^5$ is $-O-N=N(O)-NR^3R^4$;
or a pharmaceutically acceptable salt or hydrate thereof, which is useful for treating hypertension.

18 Claims, No Drawings

ANGIOTENSIN II RECEPTOR ANTAGONISTS

CROSS REFERENCE TO RELATED APPLICATIONS

This application is a U.S. National Phase application under 35 U.S.C. §371 of PCT Application No. PCT/US2009/030382 filed Jan. 8, 2009, which claims priority under 35 U.S.C. §119(e) from U.S. Provisional Application No. 61/062,267 filed on Jan. 24, 2008.

BACKGROUND OF THE INVENTION

U.S. Pat. No. 5,138,069 generically and specifically describes 2-butyl-4-chloro-1-[p-(o-1H-tetrazol-5-ylphenyl)-benzyl]imidazole-5-methanol potassium salt and 2-butyl-4-chloro-1-[(2'-1H-tetrazol-5-yl)biphenyl-4-yl)methyl]imidazole-5-carboxylic acid. Columns 261-263 of U.S. Pat. No. 5,136,069 describe general procedures for formulating compounds described in the patent, including capsules, tablets, injection formulations, and suspensions. U.S. Pat. No. 5,153,197, describes the use of these compounds, alone and in combination with a diuretic, to treat a patient having hypertension.

SUMMARY OF THE INVENTION

The present invention includes angiotensin II receptor antagonist diazeniumdiolate derivatives, including 2-butyl-4-chloro-1-[(2'-(1-H-tetrazol-5-yl)biphenyl-4-yl)methyl]-imidazole-5-carboxylate derivatives, including various pharmaceutically acceptable salts and hydrates of these forms, and pharmaceutical formulations for controlled and sustained delivery of these forms to a patient.

The salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, by administering an angiotensin II receptor antagonist of the invention to a patient having one or more of these conditions.

DETAILED DESCRIPTION OF THE INVENTION AND PREFERRED EMBODIMENTS

Compounds of the invention are angiotensin II receptor antagonist diazeniumdiolate derivatives having the general formula:

wherein R is selected from the group consisting of

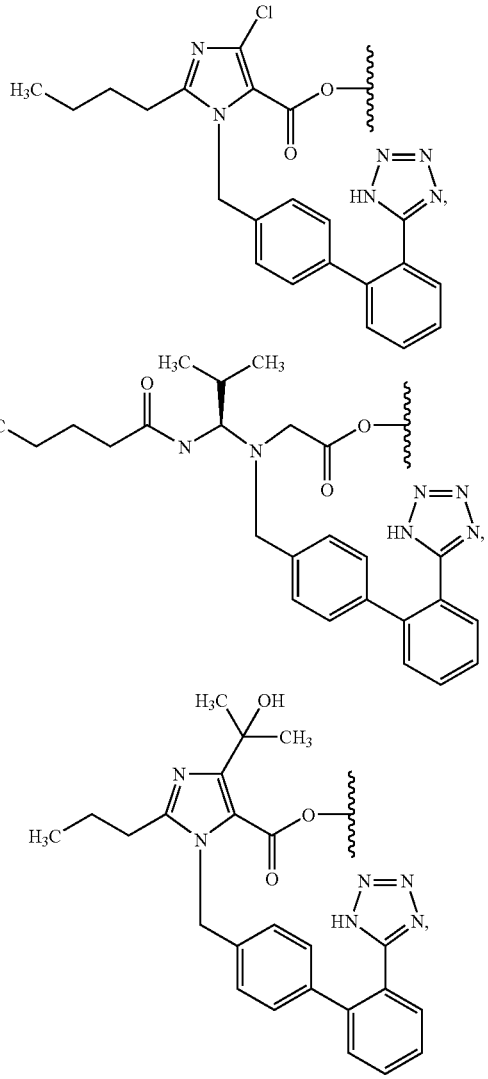

-continued

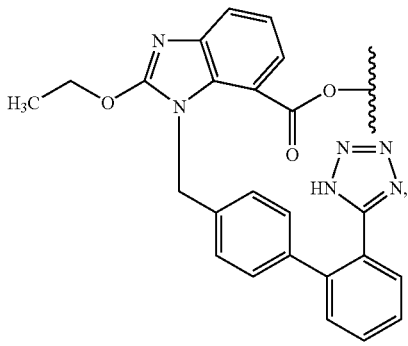

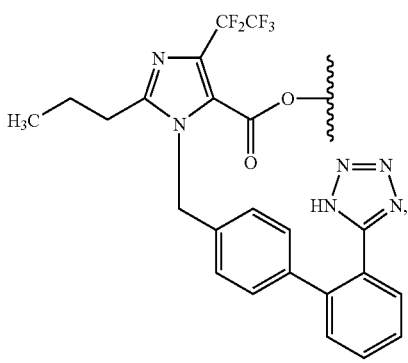

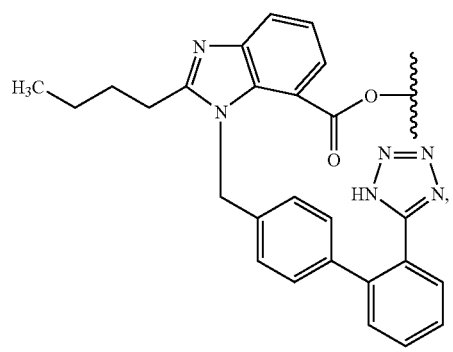

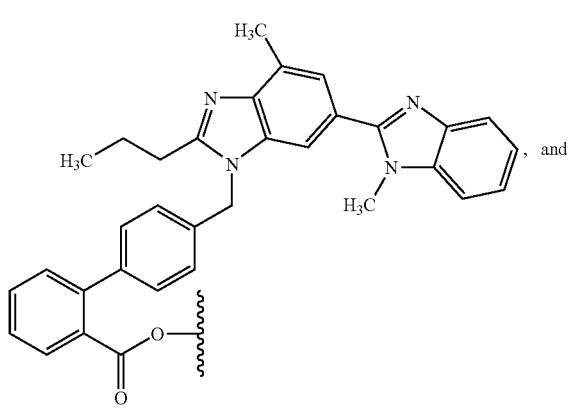

-continued

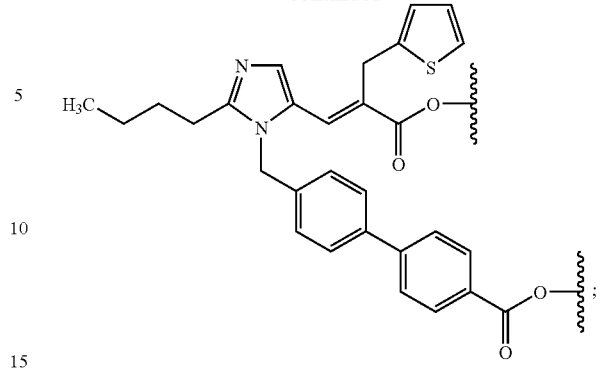

Y is selected from the group consisting of

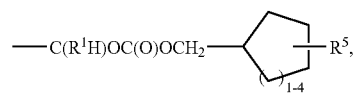

and

2) —C(R¹H)OC(O)X((CR¹²R¹³)—(CHR¹⁰)$_m$—(CH$_2$)$_n$—Z$_p$—(CH$_2$)$_q$—(CHR¹¹)$_r$—(CR¹⁶R¹⁷))—R⁵;

Z is —O— or —(CR¹⁴R¹⁵)—;

m, n, p, q, and r are independently selected from the group consisting of 0 and 1;

X is —O— or —(CR¹⁸R¹⁹)—;

R¹ is selected from the group consisting of hydrogen, C$_{1-4}$ alkyl, aryl, C$_{1-4}$ alkylarylene, and arylC$_{1-4}$ alkylene;

R⁵ is —O—N=N(O)—NR³R⁴;

R³ and R⁴ are independently selected from the group consisting of unsubstituted or substituted C$_{1-6}$ alkyl, unsubstituted or substituted C$_{1-6}$ alkenyl, unsubstituted or substituted morpholino, amino, unsubstituted or substituted benzyl, unsubstituted or substituted phenyl, unsubstituted or substituted arylC$_{1-4}$ alkyl, or R³ and R⁴ together with the nitrogen atom to which they are attached, form a ring selected from the group consisting of

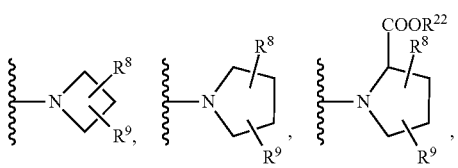

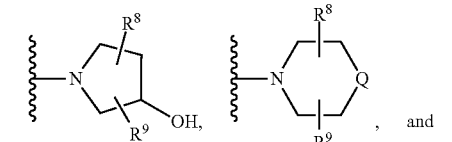

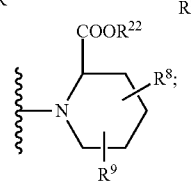

Q is selected from the group consisting of —(CR²⁰R²¹)—, —S—, —N(R⁶)— and —O—;

$R^6$ is selected from the group consisting of hydrogen, unsubstituted or substituted $C_{1-6}$ alkyl, and —$COOR^{22}$;

$R^8$, $R^9$ and $R^{22}$ are independently selected from the group consisting of hydrogen and unsubstituted or substituted $C_{1-6}$ alkyl;

$R^{10}$ and $R^{11}$ are independently selected from the group consisting of hydrogen and unsubstituted or substituted $C_{1-6}$ alkyl;

$R^{12}$, $R^{13}$, $R^{14}$, $R^{15}$, $R^{16}$, $R^{17}$, $R^{18}$, $R^{19}$, $R^{20}$ and $R^{21}$ are independently selected from the group consisting of hydrogen, unsubstituted or substituted $C_{1-6}$ alkyl, and unsubstituted or substituted aryl;

or a pharmaceutically acceptable salt thereof.

In one embodiment, $R^1$ is selected from the group consisting of $CH_3$ and $CH(CH_3)_2$.

In another embodiment, Y is —$C(R^1H)OC(O)X((CR^{12}R^{13})$—$(CHR^{10})_m$—$(CH_2)_n$—$Z_p$—$(CH_2)_q$—$(CHR^{11})_r$—$(CR^{16}R^{17}))$—$R^5$.

In another embodiment, $R^1$ is $CH_3$.

In another embodiment, $R^{10}$ and $R^{11}$ are independently selected from the group consisting of hydrogen and $CH_3$.

In another embodiment, $R^{12}$, $R^{14}$, and $R^{16}$ are independently selected from the group consisting of hydrogen, $CH_3$, and —$C_6H_5$.

In another embodiment, $R^{13}$, $R^{15}$ and $R^{17}$ are independently selected from the group consisting of hydrogen and $CH_3$.

In another embodiment, $R^{18}$, $R^{19}$, $R^{20}$, and $R^{21}$ are hydrogen.

In another embodiment, p is 1 and m, n, q, and r are 0.

In another embodiment, m, p and r are 1 and n and q are 0.

In another embodiment, m, n, p, q and r are 1.

In another embodiment, $CR^{12}R^{13}$ is selected from the group consisting of $CH_2$, $CH(CH_3)$, $CH(C_6H_5)$, and $C(CH_3)_2$.

In another embodiment, $CHR^{10}$ is selected from the group consisting of $CH_2$ and $CH(CH_3)$.

In another embodiment, Z is selected from the group consisting of —O—, —$(CH_2)$—, —$CH(CH_3)$—, —$CH(C_6H_5)$—, and —$(C(CH_3)_2)$—.

In another embodiment, $CHR^{11}$ is selected from the group consisting of $CH_2$ and $CH(CH_3)$.

In another embodiment, $CR^{16}R^{17}$ is selected from the group consisting of $CH_2$, $CH(CH_3)$, and $CH(C_6H_5)$.

In another embodiment, $R^3$ is —$CH_2CH_3$ or —$CH_3$, and $R^4$ is —$CH_2CH_3$, —$C(CH_3)_3$, —$CH(CH_3)_2$, or a cyclohexyl ring, or $R^3$ and $R^4$ together with the nitrogen atom to which they are attached form a ring selected from the group consisting of

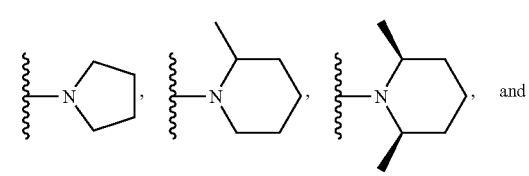

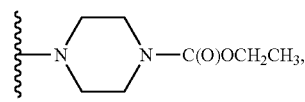

and all other variables are as previously defined.

In another embodiment, $R^3$ is —$CH_2CH_3$ and $R^4$ is —$CH_2CH_3$, or $R^3$ and $R^4$ together with the nitrogen atom to which they are attached form a pyrrolidine ring, and all other variables are as previously defined.

In another embodiment, R is selected from the group consisting of

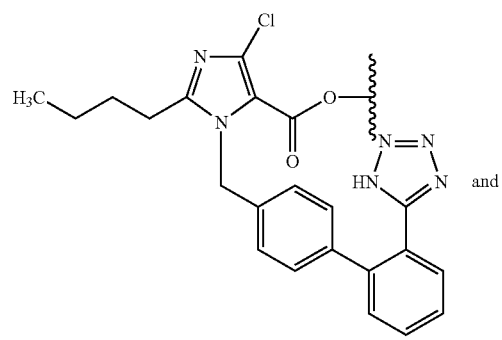

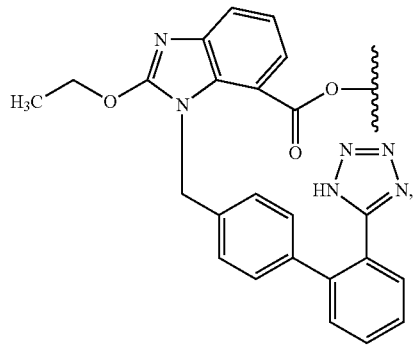

and all other variables are as previously defined.

In another embodiment, $R^5$ is selected from the group consisting of

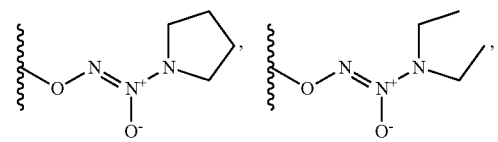

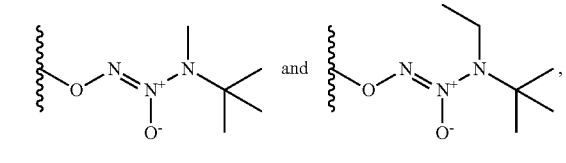

and all other variables are as previously defined.

In another embodiment, the compound is selected from the group of compounds shown in Compound Tables 1 and 2:
| COMPOUND TABLE 1 |
| --- |
| 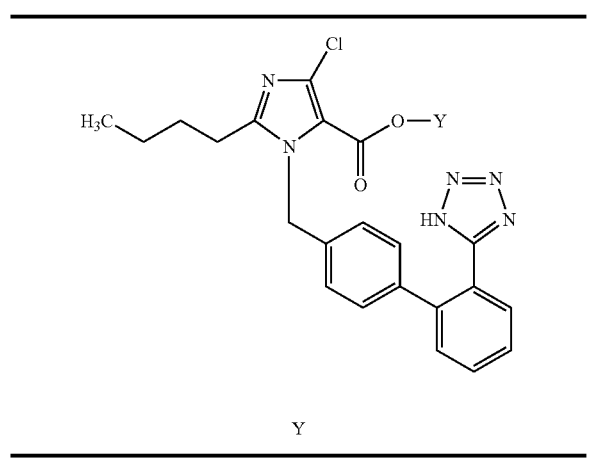 |
| Y |
| 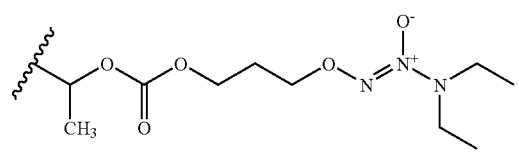 |
| 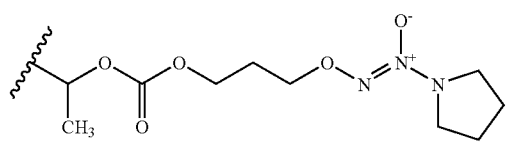 |
| 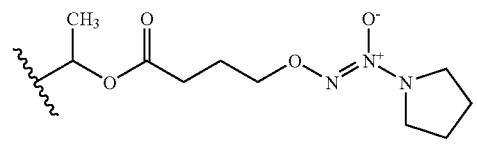 |
| COMPOUND TABLE 2 |
| --- |
| 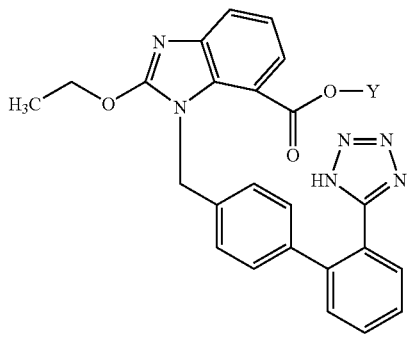 |
| Y |
| 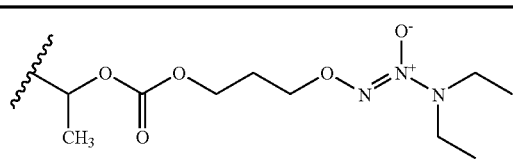 |
|  |
|  |
|  |
In another embodiment, the compound has the structure
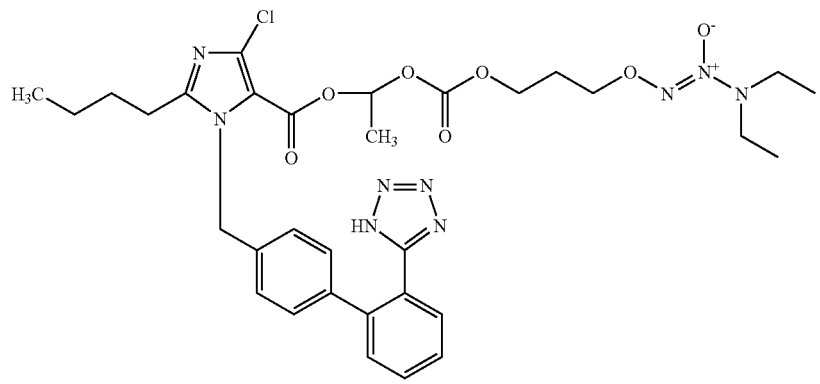
or a pharmaceutically acceptable salt thereof.

In one embodiment of the invention are angiotensin II receptor antagonist diazeniumdiolate derivatives having the general formula Ia:

Ia wherein R is selected from the group consisting of

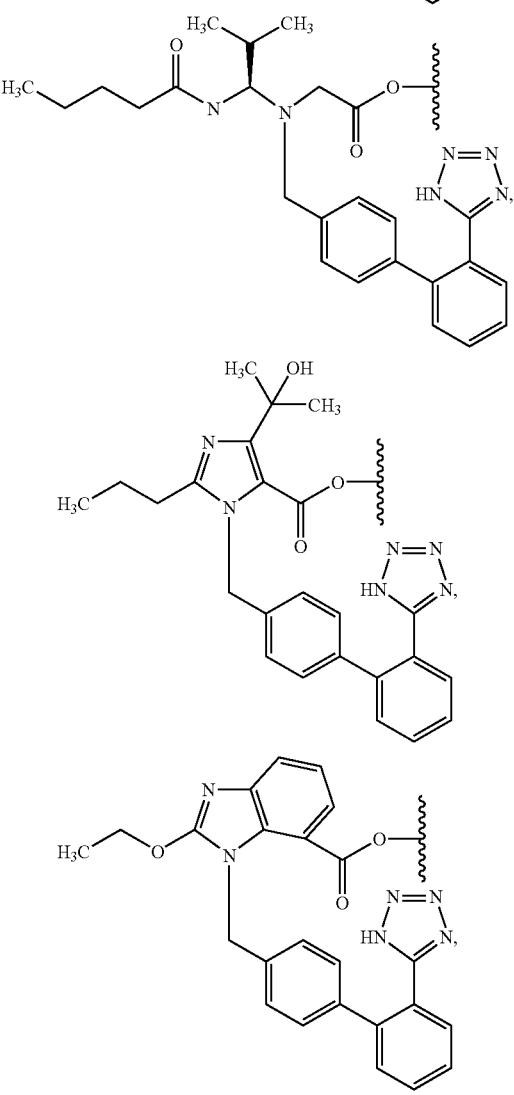

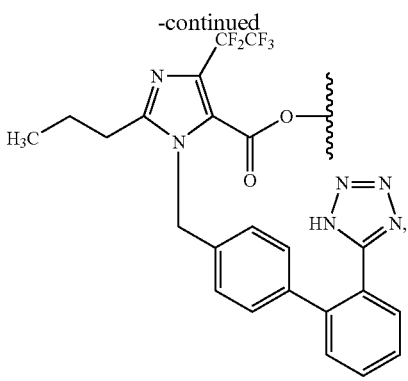

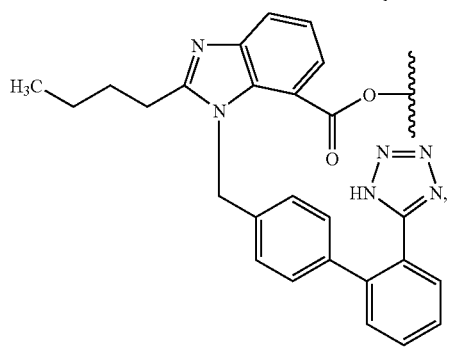

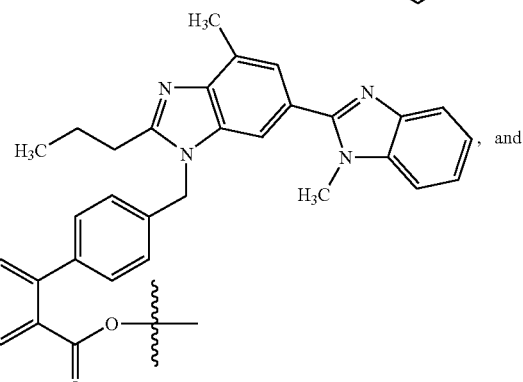

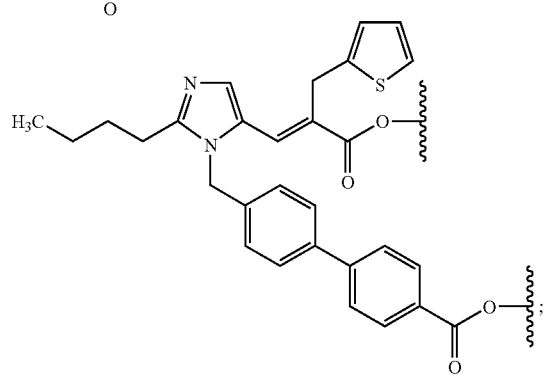

Y is —C(R$^1$H)OC(O)X(CH$_2$)$_{0-5}$(CHR$^2$)R$^5$,
X is O or CH$_2$;
R$^1$ is selected from the group consisting of hydrogen and C$_{1-4}$ alkyl;
R$^2$ is selected from the group consisting of C$_{1-12}$ alkyl, C$_{3-8}$ cycloalkyl, unsubstituted or substituted morpholino, amino, unsubstituted or substituted benzyl, unsubstituted or substituted phenyl, unsubstituted or substituted arylC$_{1-4}$ alkyl;
R$^5$ is —O—N═N(O)—NR$^3$R$^4$;

R³ and R⁴ are independently selected from the group consisting of unsubstituted or substituted $C_{1-6}$ alkyl, unsubstituted or substituted $C_{1-6}$ alkenyl, unsubstituted or substituted morpholino, amino, unsubstituted or substituted benzyl, unsubstituted or substituted phenyl, unsubstituted or substituted aryl$C_{1-4}$ alkyl, or R³ and R⁴ together with the nitrogen atom to which they are attached, form a ring selected from the grown consisting of

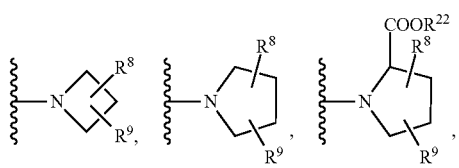

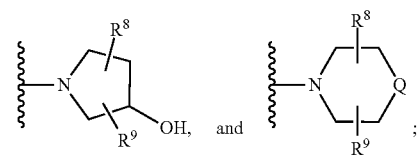

Q is selected from the group consisting of $CH_2$, S and $NR^6$;

R⁶, R⁸ and R⁹ are independently selected from the group consisting of hydrogen and unsubstituted or substituted $C_{1-6}$ alkyl;

R⁷ is selected from the group consisting of $C_{3-8}$ cycloalkyl, unsubstituted or substituted morpholino, amino, unsubstituted or substituted benzyl, unsubstituted or substituted phenyl, unsubstituted or substituted aryl$C_{1-4}$ alkyl;

or a pharmaceutically acceptable salt thereof.

In another embodiment of formula Ia, R¹ is $CH_3$ and R² is H, and all other variables are as previously defined.

In another embodiment of formula Ia, R³ is —$CH_2CH_3$ and R⁴ is —$CH_2CH_3$, or R³ and R⁴ together with the nitrogen atom to which they are attached form a pyrrolidine ring, and all other variables are as previously defined.

In another embodiment of formula Ia, R is selected from the group consisting of

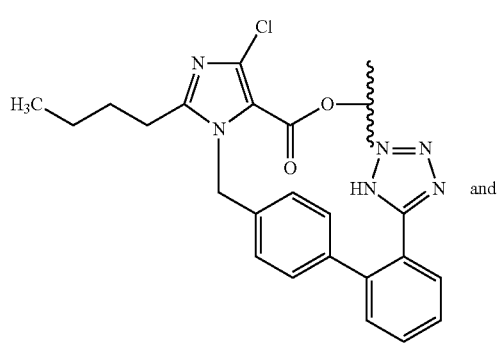

and

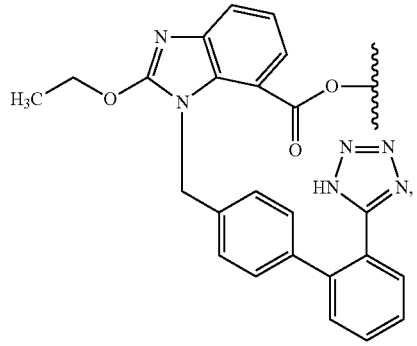

and all other variables are as previously defined.

In another embodiment of formula Ia, R⁵ is selected from the group consisting of

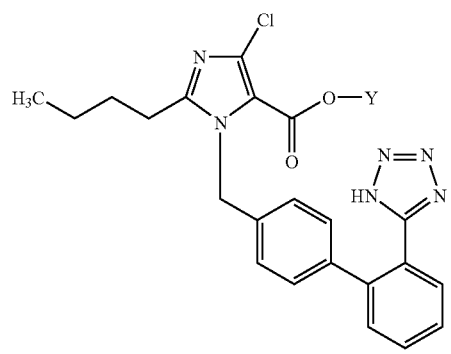

and all other variables are as previously defined.

In another embodiment of formula Ia, the compound is selected from the group of compounds shown in Compound Tables 1 and 2:

COMPOUND TABLE 1

| |
|---|
| 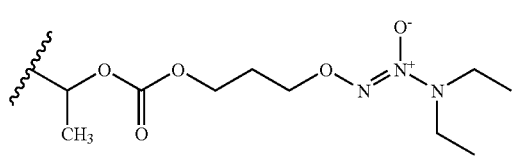 |
| Y |
| 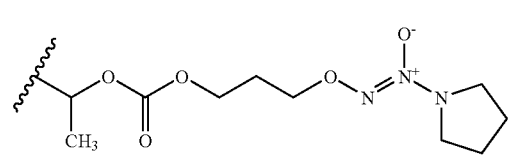 |

COMPOUND TABLE 1-continued
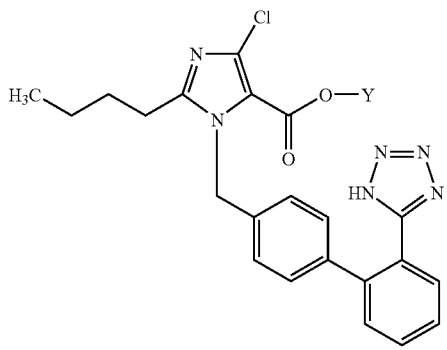
Y
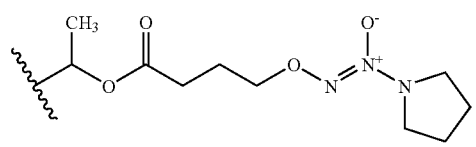
COMPOUND TABLE 2
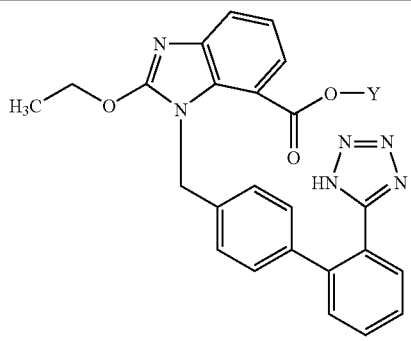
Y
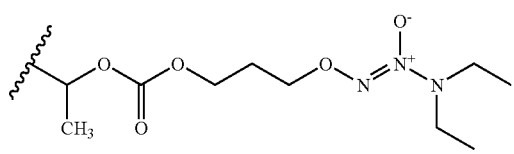
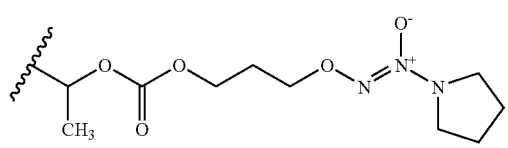
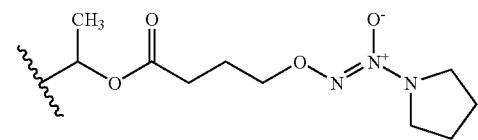
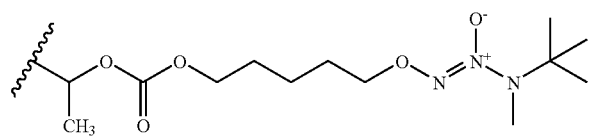
In another embodiment of formula Ia, the compound is selected from the group of compounds shown in Compound Tables 1a and 2a:
COMPOUND TABLE 1a
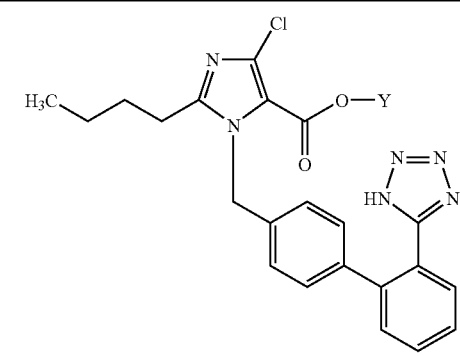
Y
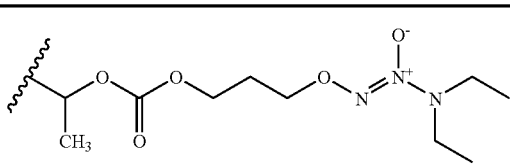
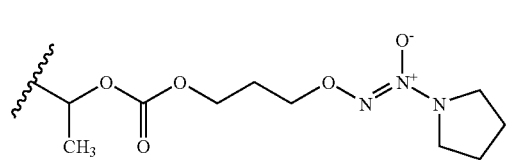
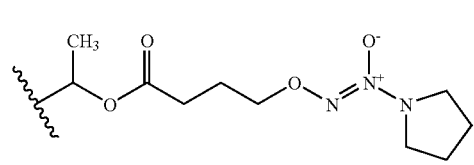
COMPOUND TABLE 2a
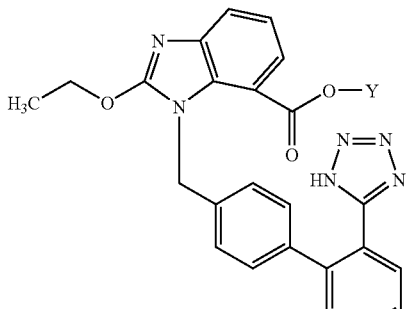
Y
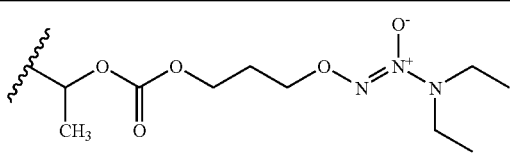

COMPOUND TABLE 2a-continued

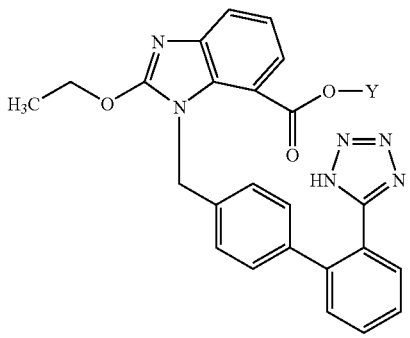

Y

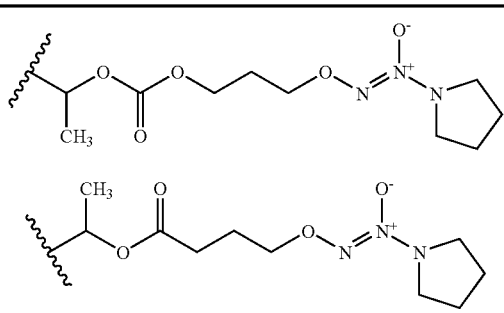

In another embodiment of formula Ia, the compound has the structure

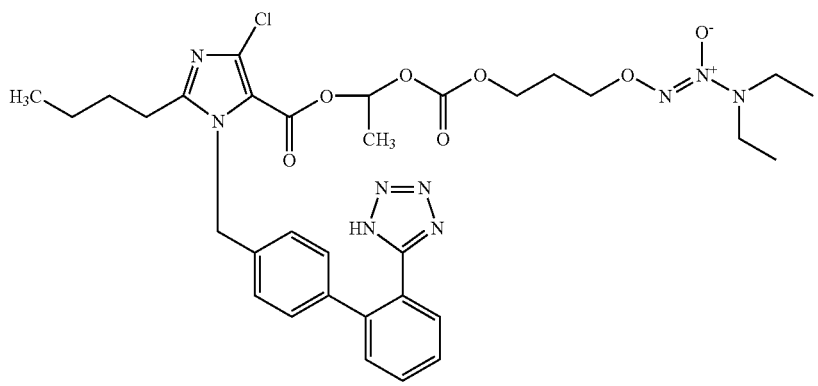

The compounds of the present invention may have one or two chiral centers, providing for up to two ((R) and (S)) or four (R,R), (S,S), (R,S), and (S,R) stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. The structure marking "*" indicates the location of a carbon atom that is a chiral center.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g. "⌇—", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

The term "alkenyl" includes both branched and straight chain unsaturated hydrocarbon groups containing at least two carbon atoms joined by a double bond. The alkene ethylene is represented, for example, by "$CH_2CH_2$" or alternatively, by "$H_2C=CH_2$". "$C_{2-5}$ alkenyl" (or "$C_2$-$C_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "$C_{2-3}$ alkenyl" have an analogous meaning.

The term "cycloalkyl" means a cyclic ring of an alkane having a specified number of ring atoms (e.g., "$C_3$-$C_8$ cycloalkyl" has three to eight total carbon atoms, e.g., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "aryl" refers to a functional group or substituent derived from a simple aromatic ring, e.g., phenyl, benzyl, tolyl, o-xylyl. The term "benzyl" refers to —$CH_2C_6H_5$. The term "phenyl" refers to —$C_6H_5$.

The term alkylarylene (e.g., $C_{1-4}$ alkylarylene) refers to a substituent group wherein the aryl portion of the substituent is attached to the substituted molecule, e.g.

The term arylalkylene (e.g., aryl$C_{1-4}$ alkylene) refers to a substituent group wherein the alkyl portion of the substituent is attached to the substituted molecule, e.g.

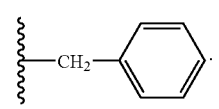

The term "amino" refers to $NH_2$.

The term "morpholino" refers to the ring

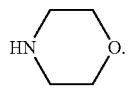

Unless indicated otherwise, the term "heterocycle" (and variations thereof such as "heterocyclic" or "heterocyclyl") broadly refers to (i) a stable 4- to 8-membered, saturated or unsaturated monocyclic ring, (ii) a stable 7- to 12-membered bicyclic ring system, or (iii) a stable 11- to 15-membered tricyclic ring system, wherein each ring in (ii) and (iii) is independent of, or fused to, the other ring or rings and each ring is saturated or unsaturated, and the monocyclic ring, bicyclic ring system or tricyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the bicyclic and tricyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Saturated heterocyclics form a subset of the heterocycles. Unless expressly stated to the contrary, the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring, a stable 7- to 12-membered bicyclic ring system, or a stable 11- to 15-membered tricyclic ring system, which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Unsaturated heterocyclics form another subset of the heterocycles. Unless expressly stated to the contrary, the term "unsaturated heterocyclic" generally refers to a heterocycle as defined above in which the entire ring system (whether mono- or poly-cyclic) is not saturated, i.e., such rings are either unsaturated or partially unsaturated. Unless expressly stated to the contrary, the term "heteroaromatic ring" refers a 5- or 6-membered monocyclic aromatic ring, a 7- to 12-membered bicyclic ring system, or a 11- to 15-membered tricyclic ring system, which consists of carbon atoms and one or more heteroatoms selected from N, O and S. In the case of substituted heteraromatic rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

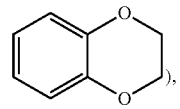

imidazo(2,1-b)(1,3)thiazole, (i.e.,

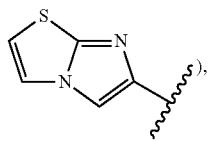

and benzo-1,3-dioxolyl (i.e.,

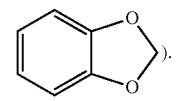

In certain contexts herein,

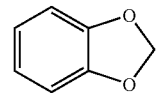

is alternatively referred to as phenyl having as a substituent methylenedioxy attached to two adjacent carbon atoms.

The term "heteroaryl", alone or in combination, refers to certain heterocyclic rings which are six-membered aromatic rings containing one to four nitrogen atoms; benzofused six-membered aromatic rings containing one to three nitrogen atoms; five-membered aromatic rings containing one oxygen, one nitrogen or one sulfur atom; benzofused five-membered aromatic rings containing one oxygen, one nitrogen or one sulfur atom; five-membered aromatic rings containing two heteroatoms independently selected from oxygen, nitrogen and sulfur and benzofused derivatives of such rings; five-membered aromatic rings containing three nitrogen atoms and benzofused derivatives thereof; a tetrazolyl ring; a thiazinyl ring; or coumarinyl.

Examples of such ring systems are furanyl, thienyl, pyrrolyl, pyridinyl, pyrimidinyl, indolyl, quinolinyl, isoquinolinyl, imidazolyl, triazinyl, thiazolyl, isothiazolyl, pyridazinyl, pyrazolyl, oxazolyl, isoxazolyl, benzothienyl, quinazolinyl and quinoxalinyl.

Unless otherwise specifically noted as only "unsubstituted" or only "substituted", morpholino, benzyl, phenyl, aryl, alkyl, alkenyl, and cycloalkyl groups are unsubstituted or substituted, where substituted groups may contain from 1 to 3 substituents in addition to the point of attachment to the rest of the compound, wherein such substituents result in formation of a stable compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl- $S(O)_{0-2}$—, $(C_0$-$C_6$ alkyl)$S(O)_{0-2}(C_0$-$C_6$ alkyl)-, $(C_0$-$C_6$ alkyl)$C(O)NH$—, $H_2N$—$C(NH)$—, —$O(C_1$-$C_6$ alkyl)$CF_3$, $(C_0$-$C_6$ alkyl)$C(O)$—, $(C_0$-$C_6$ alkyl)$OC(O)$—, $(C_0$-$C_6$ alkyl)$O(C_1$-$C_6$ alkyl)-, $(C_0$-$C_6$ alkyl)$C(O)_{1-2}(C_0$-$C_6$ alkyl)-, $(C_0$-$C_6$ alkyl)$OC(O)NH$—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The angiotensin II receptor antagonists of the invention are useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system.

The angiotensin II receptor antagonists of the invention are especially useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment and/or prophylaxis of diseases, which are associated with a dysregulation of the renin-angiotensin system, in particular to a method for the treatment or prophylaxis of the above-mentioned diseases, said methods comprising administering to a patient a pharmaceutically active amount of an angiotensin II receptor antagonist of the invention.

The invention also relates to the use of angiotensin II receptor antagonists of the invention for the preparation of a medicament for the treatment and/or prophylaxis of the above-mentioned diseases.

The above-mentioned angiotensin II receptor antagonists of the invention are also of use in combination with other pharmacologically active compounds comprising angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S,5S,7S)—N—(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone)) or with other drugs beneficial for the prevention or the treatment of the above-mentioned diseases including nitroprusside and diazoxide.

The dosage regimen utilizing the angiotensin II receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the angiotensin II receptor antagonists, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the angiotensin II receptor antagonists may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The angiotensin II receptor antagonists of the invention can be administered in such oral forms as tablets, capsules and granules. The angiotensin II receptor antagonists are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose acetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

2-Butyl-4-chloro-1-[(2'-(1-H-tetrazol-5-yl)biphenyl-4-yl) methyl]-imidazole-5-carboxylic acid is the active metabolite of 2-butyl-4-chloro-1-[p-(o-1H-tetrazol-5-ylphenyl)-benzyl] imidazole-5-methanol which is available as a monopotassium salt (also known as losartan potassium salt). Losartan potassium salt is available commercially as the active ingredient in COZAAR® (Merck & Co., Inc. (Whitehouse Station, N.J.)). The preparation of losartan potassium salt is described in U.S. Pat. Nos. 5,138,069, 5,130,439, and 5,310,928. Tetrazolylphenylboronic acid intermediates useful in the synthesis of losartan potassium salt are described in U.S. Pat. No. 5,206,374. Additional patents which describe procedures useful for making losartan include U.S. Pat. Nos. 4,820,843, 4,870,186, 4,874,867, 5,039,814, and 5,859,258.

Intermediate 1

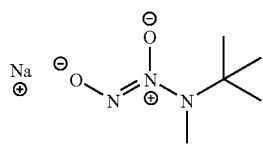

Sodium 1-(N-tert-butylmethylamino)diazen-1-ium-1, 2-diolate

To a methanolic solution (3 L) of N-tert-butylmethylamine (151 g, 1.73 mol) was added a 25 wt % methanolic solution of sodium methoxide (400 mL, 1.73 mol). The solution was stirred for 24 hours at 25° C. under nitric oxide (250 psi). The methanol was removed in vacuo, and diethyl ether was added to precipitate a white solid. The solid was filtered, washed with diethyl ether, and dried under vacuum at 25° C. to obtain the title compound. $^1$H NMR (500 MHz, D$_2$O) δ 1.17 (s, 9H), 2.71 (s, 3H).

Intermediate 2

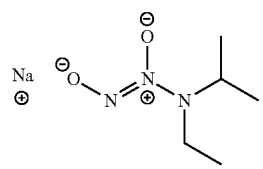

Sodium 1-(N-ethylisopropylamino)diazen-1-ium-1,2-diolate

The title compound was prepared by following the procedure for intermediate 1, except that the reagent N-tert-butyl-methylamine was replaced by N-ethylisopropylamine. $^1$H NMR (500 MHz, D$_2$O) δ 1.06 (t, J=7.1 Hz, 3H), 1.13 (d, J=6.4 Hz, 6H), 3.08 (q, J=7.1 Hz, 2H), 3.39 (septet, J=6.4 Hz, 1H).

Intermediate 3

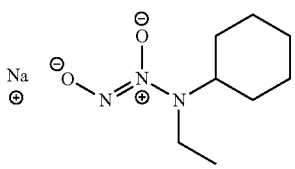

Sodium 1-(N-ethylcyclohexylamino)diazen-1-ium-1,2-diolate

The title compound was prepared by following the procedure for intermediate 1, except that the reagent N-tert-butyl-methylamine was replaced by N-ethylcyclohexylamine. $^1$H NMR (500 MHz, D$_2$O) δ 1.05 (t, J=7.1 Hz, 3H), 1.10-1.20 (m, 1H), 1.20-1.32 (m, 5H), 1.76-1.83 (m, 4H), 2.99-3.05 (m, 1H), 3.08 (q, J=6.8 Hz, 2H).

Intermediate 4

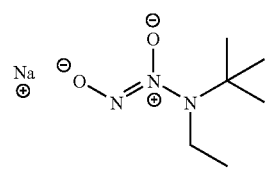

Sodium 1-(N-tert-butylethylamino)diazen-1-ium-1,2-diolate

The title compound was prepared by following the procedure for intermediate 1, except that the reagent N-tert-butyl-methylamine was replaced by N-tert-butylethylamine. $^1$H NMR (500 MHz, D$_2$O) δ 0.90 (t, J=7.0 Hz, 3H), 1.18 (s, 9H), 3.06 (q, J=6.9 Hz, 2H).

Intermediate 5

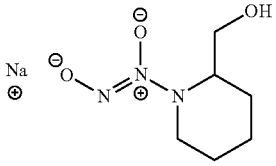

Sodium 1-[2-(hydroxymethyl)pyrrolidin-1-yl]diazen-1-ium-1,2-diolate

The title compound was prepared by following the procedure for intermediate 1, except that the reagent N-tert-butylmethylamine was replaced by (±)-2-piperidinemethanol. $^1$H NMR (500 MHz, D$_2$O) δ 1.34 (tq, J=4.1, 13.2 Hz, 1H), 1.48 (dq, J=3.4, 13.3 Hz, 1H), 1.58-1.70 (m, 1H), 1.80 (tt, J=3.2, 13.5 Hz, 2H), 1.93 (qd, J=3.0, 10.3 Hz, 1H), 3.02-3.13 (m, 3H), 3.34 (dd, J=5.7, 11.7 Hz, 1H), 3.41 (dd, J=3.2, 11.7 Hz, 1H).

Intermediate 6

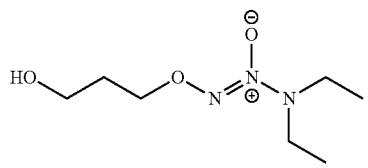

O$^2$-(3-hydroxypropyl) 1-(N,N-diethylamino)diazen-1-ium-1,2-diolate

To a N,N-dimethylformamide (2 mL) suspension of sodium 1-(N,N-diethylamino)diazen-1-ium-1,2-diolate (363 mg, 2.34 mmol) was added 3-bromopropan-1-ol (205 μL, 2.34 mmol). The reaction mixture was heated with microwaves (80° C., 10 min), and was then purified by column chromatography on silica gel, eluting with ethyl acetate/hexanes to give the title compound as a colorless liquid. $^1$H NMR (500 MHz, CDCl$_3$) δ 1.09 (t, J=7.1 Hz, 6H), 1.66 (t, J=5.1 Hz, 1H), 2.02 (quintet, J=6.3 Hz, 2H), 3.09 (q, J=7.2 Hz, 4H), 3.79 (q, J=5.6 Hz, 2H), 4.42 (t, J=6.3 Hz, 2H).

Intermediate 7

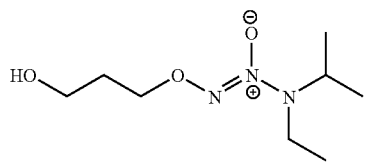

O$^2$-(3-hydroxypropyl) 1-(N-ethylisopropylamino) diazen-1-ium-1,2-diolate

The title compound was prepared by following the procedure for intermediate 6, except that the reagent sodium 1-(N, N-diethylamino)diazen-1-ium-1,2-diolate was replaced by sodium 1-(N-ethylisopropylamino)diazen-1-ium-1,2-diolate. $^1$H NMR (500 MHz, CDCl$_3$) δ 1.06 (t, J=7.1 Hz, 3H), 1.13 (d, J=6.4 Hz, 6H), 2.00 (quintet, J=6.2 Hz, 2H), 3.08 (q, J=7.1 Hz, 2H), 3.39 (septet, J=6.4 Hz, 1H), 3.74-3.80 (m, 2H), 4.42 (t, J=6.2 Hz, 2H).

Intermediate 8

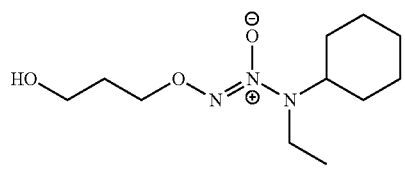

O$^2$-(3-hydroxypropyl) 1-(N-ethylcyclohexylamino) diazen-1-ium-1,2-diolate

The title compound was prepared by following the procedure for intermediate 6, except that the reagent sodium 1-(N, N-diethylamino)diazen-1-ium-1,2-diolate was replaced by sodium 1-(N-ethylcyclohexylamino)diazen-1-ium-1,2-diolate. $^1$H NMR (500 MHz, CDCl$_3$) δ 1.05 (t, J=7.1 Hz, 3H), 1.10-1.20 (m, 1H), 1.20-1.30 (m, 4H), 1.59-1.66 (m, 1H), 1.75-1.83 (m, 4H), 2.00 (quintet, J=6.2 Hz, 2H), 2.98-3.05 (m, 1H), 3.08 (q, J=6.8 Hz, 2H), 3.77 (q, J=5.7 Hz, 2H), 4.42 (t, J=6.4 Hz, 2H).

Intermediate 9

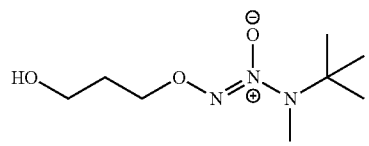

O$^2$-(3-hydroxypropyl) 1-(N-tert-butylmethylamino) diazen-1-ium-1,2-diolate

The title compound was prepared by following the procedure for intermediate 6, except that the reagent sodium 1-(N, N-diethylamino)diazen-1-ium-1,2-diolate was replaced by sodium 1-(N-tert-butylmethylamino)diazen-1-ium-1,2-diolate. $^1$H NMR (500 MHz, CDCl$_3$) δ 1.22 (s, 9H), 2.01 (quintet, J=6.2 Hz, 2H), 2.80 (s, 3H), 3.76 (t, J=5.2 Hz, 2H), 4.40 (t, J=6.4 Hz, 2H).

Intermediate 10

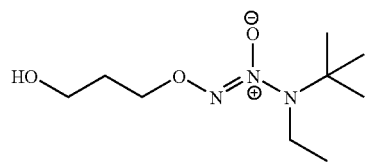

O$^2$-(3-hydroxypropyl) 1-(N-tert-butylethylamino) diazen-1-ium-1,2-diolate

The title compound was prepared by following the procedure for intermediate 6, except that the reagent sodium 1-(N, N-diethylamino)diazen-1-ium-1,2-diolate was replaced by sodium 1-(N-tert-butylethylamino)diazen-1-ium-1,2-diolate. ¹H NMR (500 MHz, CDCl₃) δ 1.02 (t, J=6.9 Hz, 3H), 1.22 (s, 9H), 1.98 (quintet, J=6.2 Hz, 2H), 3.09 (q, J=7.1 Hz, 2H), 3.75 (t, J=6.0 Hz, 2H), 4.41 (t, J=6.4 Hz, 2H).

Intermediate 11

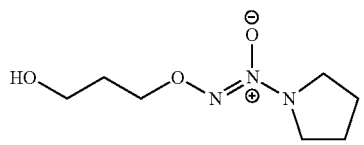

O²-(3-hydroxypropyl) 1-(pyrrolidin-1-yl)diazen-1-ium-1,2-diolate

The title compound was prepared by following the procedure for intermediate 6, except that the reagent sodium 1-(N,N-diethylamino)diazen-1-ium-1,2-diolate was replaced by sodium 1-(pyrrolidin-1-yl)diazen-1-ium-1,2-diolate (prepared as described in Saavedra, J. E.; Billiar T. R.; Williams, D. L.; Kim, Y.-M.; Watkins, S. C.; Keefer, L. K. *J. Med. Chem.* 1997, 40, 1947-1954.). ¹H NMR (500 MHz, CDCl₃) δ 1.89 (quintet, J=6.0 Hz, 2H), 1.90-2.00 (m, 4H), 3.55 (t, J=7.0 Hz, 4H), 3.63 (t, J=6.0 Hz, 2H), 4.31 (t, J=6.0 Hz, 2H).

Intermediate 12

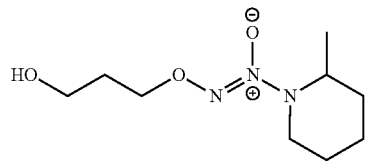

O²-(3-hydroxypropyl) 1-(2-methylpiperidin-1-yl)diazen-1-ium-1,2-diolate

The title compound was prepared by following the procedure for intermediate 6, except that the reagent sodium 1-(N,N-diethylamino)diazen-1-ium-1,2-diolate was replaced by sodium 1-(2-methylpiperidin-1-yl)diazen-1-ium-1,2-diolate (prepared as described in Chakrapani, H.; Showalter, B. M.; Citro, M. L.; Keefer, L. K.; Saavedra, J. E. *Org. Lett.* 2007, 9, 4551-4554.). ¹H NMR (500 MHz, CDCl₃) δ 1.02 (d, J=5.9 Hz, 3H), 1.30-1.50 (m, 1H), 1.64-1.83 (m, 5H), 2.00 (quintet, J=5.9 Hz, 2H), 3.14-3.24 (m, 3H), 3.77 (t, J=5.7 Hz, 2H), 4.42 (t, J=6.4 Hz, 2H).

Intermediate 13

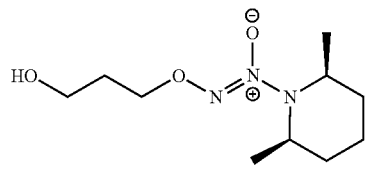

O²-(3-hydroxypropyl) 1-(cis-2,6-dimethylpiperidin-1-yl)diazen-1-ium-1,2-diolate

The title compound was prepared by following the procedure for intermediate 6, except that the reagent sodium 1-(N,N-diethylamino)diazen-1-ium-1,2-diolate was replaced by sodium 1-(cis-2,6-dimethylpiperidin-1-yl)diazen-1-ium-1,2-diolate (prepared as described in Chakrapani, H.; Showalter, B. M.; Citro, M. L.; Keefer, L. K.; Saavedra, J. E. *Org. Lett.* 2007, 9, 4551-4554.). ¹H NMR (500 MHz, CDCl₃) δ 1.02 (d, J=6.2 Hz, 6H), 1.38-1.50 (m, 2H), 1.60-1.71 (m, 2H), 1.76-1.82 (m, 2H), 2.00 (quintet, J=6.1 Hz, 2H), 3.13-3.22 (m, 2H), 3.77 (t, J=5.5 Hz, 2H), 4.44 (t, J=6.5 Hz, 2H).

Intermediate 14

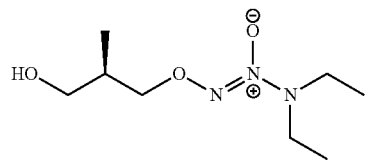

O²-[(2R)-3-hydroxy-2-methylpropyl] 1-(N,N-diethylamino)diazen-1-ium-1,2-diolate

The title compound was prepared by following the procedure for intermediate 6, except that the reagent 3-bromopropan-1-ol was replaced by (R)-(−)-3-bromo-2-methyl-1-propanol. ¹H NMR (500 MHz, CDCl₃) δ 0.98 (d, J=7.0 Hz, 3H), 1.09 (t, J=7.0 Hz, 6H), 1.74 (br s, 1H), 2.13-2.22 (m, 1H), 3.09 (q, J=7.0 Hz, 4H), 3.63 (d, J=5.5 Hz, 2H), 4.25 (d, J=5.5 Hz, 2H).

Intermediate 15

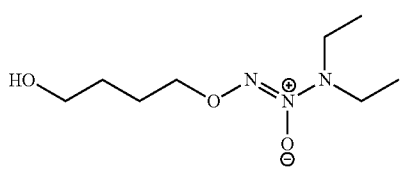

O²-(4-hydroxybutyl) 1-(N,N-diethylamino)diazen-1-ium-1,2-diolate

The title compound was prepared by following the procedure for intermediate 6, except that the reagent 3-bromopropan-1-ol was replaced by 4-bromo-1-butanol. ¹H NMR (500 MHz, CDCl₃) δ 1.06 (t, J=7.0 Hz, 6H), 1.60-1.68 (m, 2H), 1.79-1.87 (m, 2H), 1.93 (br s, 1H), 3.06 (q, J=7.0 Hz, 4H), 3.60-3.67 (m, 2H), 4.29 (t, J=6.5 Hz, 2H).

Intermediate 16

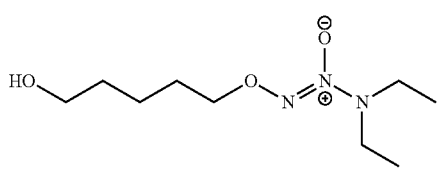

O²-(5-hydroxypentyl) 1-N,N-diethylamino)diazen-1-ium-1,2-diolate

The title compound was prepared by following the procedure for intermediate 6, except that the reagent 3-bromopropan-1-ol was replaced by 5-bromo-1-pentanol. ¹H NMR (500 MHz, CDCl₃) δ 1.04 (t, J=7.0 Hz, 6H), 1.43 (quintet, J=7.5 Hz, 2H), 1.56 (quintet, J=7.5 Hz, 2H), 1.75 (quintet, J=7.5 Hz, 2H), 1.95 (br s, 1H), 3.03 (q, J=7.0 Hz, 4H), 3.59 (t, J=6.5 Hz, 2H), 4.23 (t, J=6.5 Hz, 2H).

Intermediate 17

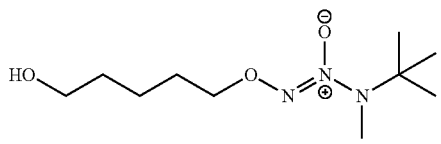

O²-(5-hydroxypentyl) 1-(N-tert-bulmethylamino)diazen-1-ium-1,2-diolate

The title compound was prepared by following the procedure for intermediate 16, except that the reagent sodium 1-(N,N-diethylamino)diazen-1-ium-1,2-diolate was replaced by sodium 1-(N-tert-butylmethylamino)diazen-1-ium-1,2-diolate. ¹H NMR (500 MHz, CDCl₃) δ 1.23 (s, 9H), 1.38 (br s, 1H), 1.47 (quintet, J=7.0 Hz, 2H), 1.60 (quintet, J=7.0 Hz, 2H), 1.80 (quintet, J=7.0 Hz, 2H), 2.81 (s, 3H), 3.64 (t, J=6.5 Hz, 2H), 4.26 (t, J=6.5 Hz, 2H).

Intermediate 18

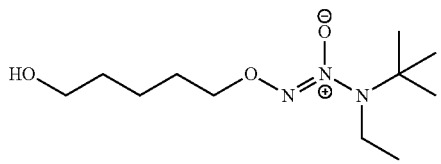

O²-(5-hydroxypentyl) 1-(N-tert-butylethylamino)diazen-1-ium-1,2-diolate

The title compound was prepared by following the procedure for intermediate 16, except that the reagent sodium 1-(N,N-diethylamino)diazen-1-ium-1,2-diolate was replaced by sodium 1-(N-tert-butylethylamino)diazen-1-ium-1,2-diolate. ¹H NMR (500 MHz, CDCl₃) δ 1.03 (t, J=7.0 Hz, 3H), 1.23 (s, 9H), 1.42-1.50 (m, 2H), 1.59 (quintet, J=7.0 Hz, 2H), 1.79 (quintet, J=7.0 Hz, 2H), 3.10 (q, J=6.5 Hz, 2H), 3.63 (t, J=6.5 Hz, 2H), 4.27 (t, J=6.5 Hz, 2H).

Intermediate 19

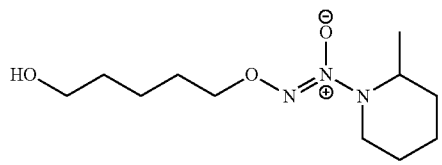

O²-(5-hydroxypentyl) 1-(2-methylpiperidin-1-yl)diazen-1-ium-1,2-diolate

The title compound was prepared by following the procedure for intermediate 16, except that the reagent sodium 1-(N,N-diethylamino)diazen-1-ium-1,2-diolate was replaced by sodium 1-(2-methylpiperidin-1-yl)diazen-1-ium-1,2-diolate. ¹H NMR (500 MHz, CDCl₃) δ 1.01 (d, J=6.0 Hz, 3H), 1.30-1.50 (m, 4H), 1.59 (quintet, J=7.0 Hz, 2H), 1.67-1.83 (m, 6H), 3.13-3.22 (m, 3H), 3.63 (t, J=6.5 Hz, 2H), 4.27 (t, J=6.5 Hz, 2H).

Intermediate 20

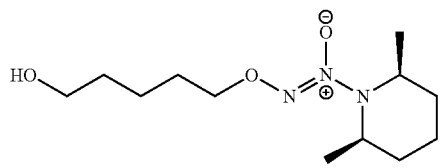

O²-(5-hydroxypentyl) 1-(cis-2,6-dimethylpiperidin-1-yl)diazen-1-ium-1,2-diolate

The title compound was prepared by following the procedure for intermediate 16, except that the reagent sodium 1-(N,N-diethylamino)diazen-1-ium-1,2-diolate was replaced by sodium 1-(cis-2,6-dimethylpiperidin-1-yl)diazen-1-ium-1,2-diolate. ¹H NMR (500 MHz, CDCl₃) δ 1.01 (d, J=6.5 Hz, 6H), 1.38-1.50 (m, 6H), 1.55-1.62 (m, 2H), 1.75-1.83 (m, 4H), 3.12-3.20 (m, 2H), 3.63 (t, J=6.5 Hz, 2H), 4.29 (t, J=6.5 Hz, 2H).

Intermediate 21

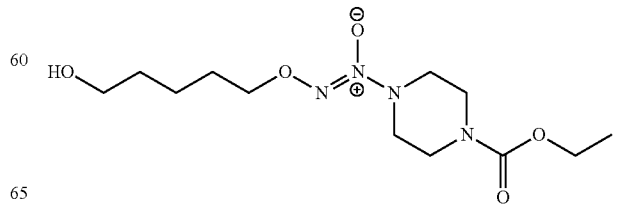

O²-(5-hydroxypentyl) 1-[4-(ethoxycarbonyl)piper-azin-1-yl]diazen-1-ium-1,2-diolate The title compound was prepared by following the procedure for intermediate 16, except that the reagent sodium 1-(N,N-diethylamino)diazen-1-ium-1,2-diolate was replaced by sodium 1-(4-ethoxycarbonylpiperazin-1-yl)diazen-1-ium-1,2-diolate (prepared as described in Saavedra, J. E.; Booth, M. N.; Hrabie, J. A.; Davies, K. M.; Keefer, L. K. *J. Org. Chem.* 1999, 64, 5124-5131.). ¹H NMR (500 MHz, CDCl₃) δ 1.24 (t, J=7.0 Hz, 3H), 1.41-1.51 (m, 2H), 1.53-1.61 (m, 1H), 1.71-1.80 (m, 3H), 3.30-3.38 (m, 4H), 3.41-3.47 (m, 1H), 3.58-3.66 (m, 5H), 4.12 (q, J=7.0 Hz, 2H), 4.19 (q, J=6.0 Hz, 2H).

Intermediate 22

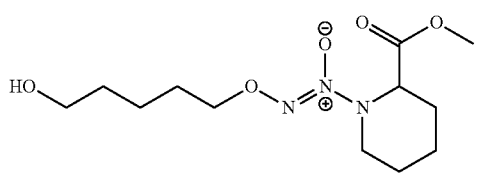

O²-(5-hydroxypentyl) 1-[2-(methoxycarbonyl)piperi-din-1-yl]diazen-1-ium-1,2-diolate Step A: O²-(5-(benzyloxy)pentyl) 1-[2-(hydroxym-ethyl)pyrrolidin-1-yl]diazen-1-ium-1,2-diolate The title compound was prepared by following the procedure for intermediate 6, except that the reagent sodium 1-(N,N-diethylamino)diazen-1-ium-1,2-diolate was replaced by sodium 1-[2-(hydroxymethyl)pyrrolidin-1-yl]diazen-1-ium-1,2-diolate, and 3-bromopropan-1-ol was replaced by benzyl 5-bromopentyl ether. LC-MS (M+H) found 352.4.

Step B: O²-(5-(benzyloxy)pentyl) 1-[2-(carboxylato)piperidin-1-yl]diazen-1-ium-1,2-diolate Ruthenium(IV) oxide (24 mg, 0.18 mmol) was added to an acetonitrile/ethyl acetate/water (1:1:1) solution (9 mL) of O²-(5-(benzyloxy)pentyl) 1-[2-(hydroxymethyl)pyrrolidin-1-yl]diazen-1-ium-1,2-diolate (517 mg, 1.47 mmol) and sodium periodate (940 mg, 4.39 mmol). The reaction mixture was stirred for 1 hour and filtered through a pad of diatomaceous earth. Water was removed azeotropically, and the residue was brought up in diethyl ether (15 mL). The product was extracted into 1N sodium hydroxide solution (5 mL). The aqueous extracts were neutralized with 1N hydrochloric acid (6 mL) and extracted into diethyl ether (3×25 mL). The organic extracts were washed with water, brine, and dried (magnesium sulfate) to give the title compound as a brown oil. LC-MS (M+H) found 366.4.

Step C: O²-(5-(benzyloxy)pentyl) 1-[2-(methoxycar-bonyl)piperidin-1-yl]diazen-1-ium-1,2-diolate A 2.0M hexanes solution of (trimethylsilyl)diazomethane (0.43 mL, 0.86 mmol) was added dropwise to a tert-butyl methyl ether (3 mL) and methanol (0.20 mL) solution of O²-(5-(benzyloxy)pentyl) 1-[2-(carboxylato)piperidin-1-yl]diazen-1-ium-1,2-diolate (315 mg, 0.862 mmol) at ambient temperature. The reaction mixture was stirred for 30 minutes and concentrated in vacuo. The residue was purified by column chromatography on silica gel, eluting with 0-70% ethyl acetate/hexanes to give the title compound as a yellow oil. LC-MS (M+H) found 380.5.

Step D: O²-(5-hydroxypentyl) 1-[2-(methoxycarbo-nyl)piperidin-1-yl]diazen-1-ium-1,2-diolate Palladium on carbon (29 mg, 0.03 mmol) was added to an ethanol solution (5 mL) of O²-(5-(benzyloxy)pentyl) 1-[2-(methoxycarbonyl)piperidin-1-yl]diazen-1-ium-1,2-diolate (91 mg, 0.24 mmol). The reaction vessel was evacuated and refilled with hydrogen, introduced through a balloon. After 24 hours, the reaction mixture was filtered through diatomaceous earth, and the residue was purified by column chromatography on silica gel, eluting with 0-100% ethyl acetate/hexanes to give the title compound as a yellow oil. ¹H NMR (500 MHz, CDCl₃) δ 1.44-1.50 (m, 2H), 1.51-1.57 (m, 2H), 1.61-1.68 (m, 2H), 1.72-1.80 (m, 2H), 1.80-1.89 (m, 2H), 1.98-2.04 (m, 2H), 3.47 (t, J=6.4 Hz, 2H), 3.50-3.56 (m, 1H), 3.58-3.63 (m, 1H), 3.70 (s, 3H), 4.21 (t, J=6.8 Hz, 2H), 4.43 (t, J=5.5 Hz, 1H); LC-MS (M+H) found 290.4.

Intermediate 23

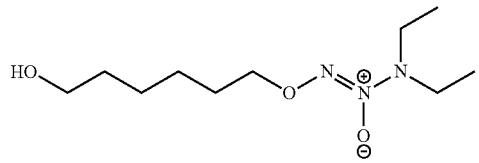

O²-(6-hydroxyhexyl) 1-(N,N-diethylamino)diazen-1-ium-1,2-diolate

The title compound was prepared by following the procedure for intermediate 6, except that the reagent 3-bromopro-pan-1-ol was replaced by 6-bromo-1-hexanol. ¹H NMR (500 MHz, CDCl₃) δ 1.04 (t, J=7.0 Hz, 6H), 1.29-1.41 (m, 2H), 1.47-1.56 (m, 2H), 1.69-1.77 (m, 2H), 1.92-2.03 (m, 2H), 3.03 (q, J=7.0 Hz, 4H), 3.58 (t, J=6.5 Hz, 2H), 4.22 (t, J=6.5 Hz, 2H).

Intermediate 24

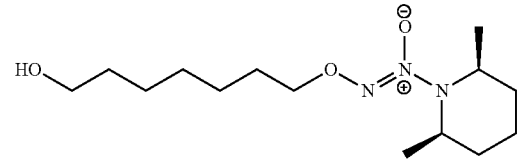

O²-(7-hydroxyheptyl) 1-(cis-2,6-dimethylpiperidin-1-yl)diazen-1-ium-1,2-diolate

The title compound was prepared by following the procedure for intermediate 20, except that the reagent 5-bromo-1-pentanol was replaced by 7-bromo-1-heptanol. ¹H NMR (500 MHz, CDCl₃) δ 1.00 (d, J=6.0 Hz, 6H), 1.28-1.48 (m, 8H), 1.49-1.58 (m, 4H), 1.70-1.79 (m, 4H), 3.11-3.19 (m, 2H), 3.60 (t, J=7.0 Hz, 2H), 4.26 (t, J=7.0 Hz, 2H).

Intermediate 25

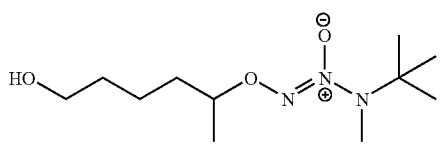

O²-(6-hydroxyhexan-2-yl) 1-(N-tert-butylmethylamino)diazen-1-ium-1,2-diolate

The title compound was prepared by following the procedure for intermediate 9, except that the reagent 3-bromopropan-1-ol was replaced by 5-bromohexan-1-ol (prepared as described in Pelletier, J. D.; Poirier, D. *Tetrahedron Lett.* 1994, 35, 1051-1054.). ¹H NMR (500 MHz, CDCl₃) δ 1.23 (s, 9H), 1.35 (d, J=6.4 Hz, 3H), 1.42-1.52 (m, 2H), 1.54-1.66 (m, 3H), 1.78-1.86 (m, 1H), 2.80 (s, 3H), 3.63 (t, J=6.4 Hz, 2H), 4.43 (sextet, J=6.4 Hz, 1H).

Intermediate 26

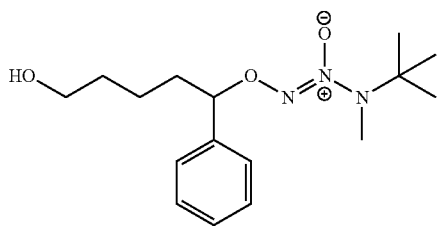

O²-(5-hydroxy-1-phenylpentyl) 1-(N-tert-butylmethylamino)diazen-1-ium-1,2-diolate Step A: 1-phenylpentane-1,5-diol A 2.0 M tetrahydrofuran solution of lithium aluminum hydride (2.80 mL, 5.60 mmol) was added to a tetrahydrofuran solution (10 mL) of methyl 5-oxo-5-phenylpentanoate (500 mg, 2.78 mmol) at 0° C. The reaction mixture was stirred for one hour and quenched with the sequential addition of water (0.2 mL), 10% sodium hydroxide solution (0.2 mL), and water (0.6 mL). It was concentrated in vacuo to give the title compound as a colorless oil. ¹H NMR (500 MHz, CDCl₃) δ 1.32-1.42 (m, 1H), 1.46-1.55 (m, 1H), 1.56-1.64 (m, 2H), 1.70-1.78 (m, 1H), 1.78-1.88 (m, 1H), 3.63 (t, J=6.6 Hz, 2H), 4.68 (dd, J=5.7, 7.8 Hz, 1H), 7.25-7.30 (m, 1H), 7.32-7.35 (m, 4H).

Step B: 5-bromo-5-phenylpentan-1-ol

Boron tribromide (1.2 mL, 12.69 mol) was slowly added to a dichloromethane solution (40 mL) of 1-phenylpentane-1,5-diol (1.89 g, 10.52 mmol) at 0° C. The reaction mixture was stirred for one hour and quenched with water. The aqueous layer was extracted with dichloromethane (3×10 mL), and the combined organics were dried (magnesium sulfate). The residue was purified by column chromatography on silica gel, eluting with 0-100% ethyl acetate/hexanes to give the title compound as a yellow oil. ¹H NMR (500 MHz, CDCl₃) δ 1.33-1.44 (m, 1H), 1.52-1.70 (m, 2H), 1.90-2.00 (m, 1H), 2.13-2.22 (m, 1H), 2.27-2.36 (m, 1H), 3.65 (t, J=6.3 Hz, 2H), 4.96 (dd, J=6.9, 8.0 Hz, 1H), 7.24-7.30 (m, 1H), 7.33 (t, J=7.8 Hz, 2H), 7.39 (d, J=7.1 Hz, 2H).

Step C: O²-(5-hydroxy-1-phenylpentyl) 1-(N-tert-butylmethylamino)diazen-1-ium-1,2-diolate The title compound was prepared by following the procedure for intermediate 9, except that the reagent 3-bromopropan-1-ol was replaced by 5-bromo-5-phenylpentan-1-ol. ¹H NMR (500 MHz, CDCl₃) δ 1.08 (s, 9H), 1.46-1.50 (m, 2H), 1.48-1.60 (m, 2H), 1.87-1.96 (m, 1H), 2.10-2.20 (m, 1H), 2.74 (s, 3H), 3.62 (t, J=6.2 Hz, 2H), 5.22 (t, J=6.6 Hz, 1H), 7.26-7.29 (m, 1H), 7.30-7.32 (m, 4H).

Intermediate 27

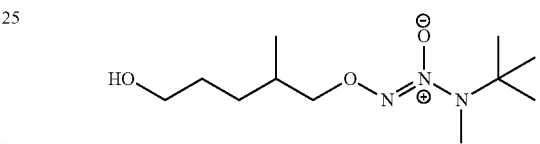

O²-(5-hydroxy-2-methylpentyl) 1-(N-tert-butylmethylamino)diazen-1-ium-1,2-diolate Step A: Ethyl 5-iodo-4-methylpentanoate A 1.0 M tetrahydrofuran solution of borane tetrahydrofuran complex (15.0 mL, 15.0 mmol) was slowly added to a tetrahydrofuran solution (7 mL) of ethyl 4-methyl-4-pentenoate (6.07 g, 42.7 mmol) at 0° C. The solution was heated to 50° C. for one hour then cooled to ambient temperature. Anhydrous methanol (1 mL) was added to quench the excess hydride, followed by sodium acetate (43 mL, 43.0 mmol) in methanol. To this reaction mixture at ambient temperature was added slowly iodine monochloride (1.5 mL, 30 mmol). The reaction mixture was stirred for two hours and poured into water (50 mL). Saturated aqueous sodium thiosulfate was added, and the mixture was extracted with diethyl ether (3×100 mL). The combined organic extracts were washed with brine, dried (magnesium sulfate), and concentrated in vacuo. The residue was purifed by column chromatography on silica gel, eluting with 0-30% ethyl acetate/hexanes to give the title compound as a colorless oil. ¹H NMR (500 MHz, CDCl₃) δ 1.00 (d, J=5.5 Hz, 3H), 1.25 (t, J=7.0 Hz, 3H), 1.45-1.60 (m, 2H), 1.70-1.78 (m, 1H), 2.30 (t, J=7.1 Hz, 2H), 3.15 (dd, J=4.7, 9.4 Hz, 1H), 3.21 (dd, J=6.3, 9.4 Hz, 1H), 4.12 (q, J=7.1 Hz, 2H).

Step B: O²-(5-ethoxy-2-methyl-5-oxopentyl) 1-(N-tert-butylmethylamino)diazen-1-ium-1,2-diolate The title compound was prepared by following the procedure for intermediate 17, except that the reagent 5-bromo-1-pentanol was replaced by ethyl 5-iodo-4-methylpentanoate.

¹H NMR (500 MHz, CDCl₃) δ 0.97 (d, J=6.6 Hz, 3H), 1.23 (s, 9H), 1.24 (t, J=7.1 Hz, 3H), 1.46-1.56 (m, 2H), 1.75-1.84 (m, 1H), 1.86-2.02 (m, 2H), 2.80 (s, 3H), 4.00-4.10 (m, 2H), 4.11 (q, J=7.0 Hz, 2H).

Step C: O²-(5-hydroxy-2-methylpentyl) 1-(N-tert-butylmethylamino)diazen-1-ium-1,2-diolate The title compound was prepared by following step A for intermediate 26, except that the reagent methyl 5-oxo-5-phenylpentanoate was replaced by O²-(5-ethoxy-2-methyl-5-oxopentyl) 1-(N-tert-butylmethylamino)diazen-1-ium-1,2-diolate. ¹H NMR (500 MHz, CDCl₃) δ 0.96 (d, J=6.9 Hz, 3H), 1.23 (s, 9H), 1.49-1.58 (m, 1H), 1.64-1.71 (m, 1H), 1.73-1.82 (m, 2H), 1.93-2.20 (m, 1H), 2.80 (s, 3H), 4.03-4.12 (m, 2H), 4.18 (t, J=6.7 Hz, 2H).

Intermediate 28

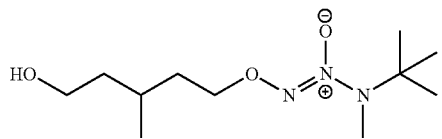

O²-(5-hydroxy-3-methylpentyl) 1-(N-tert-butylmethylamino)diazen-1-ium-1,2-diolate Step A: 5-iodo-3-methylpentane-1-ol To a solution of 3-methyl-1,5-pentanediol (26.9 g, 239 mmol) in acetonitrile (300 mL) was added sodium iodide (35.9 g, 239 mmol), followed by zirconium (IV) chloride (6.6 mL, 80 mmol) in several portions. The suspension was heated at 90° C. for 20 minutes and diluted with diethyl ether (200 mL), washed with water, saturated sodium thiosulfate solution, and brine. The organic layer was dried (magnesium sulfate), filtered, and concentrated in vacuo. The residue was purified by column chromatography on silica gel, eluting with 0-50% ethyl acetate/hexanes to give the title compound as a yellow oil. ¹H NMR (500 MHz, CDCl₃) δ 0.90 (d, J=6.5 Hz, 3H), 1.36-1.44 (m, 1H), 1.55-1.64 (m, 1H), 1.64-1.75 (m, 2H), 1.84-1.92 (m, 1H), 2.16 (br s, 1H), 3.13-3.19 (m, 1H), 3.21-3.27 (m, 1H), 3.62-3.72 (m, 2H).

Step B: O²-(5-hydroxy-3-methylpentyl) 1-(N-tert-butylmethylamino)diazen-1-ium-1,2-diolate The title compound was prepared by following the procedure for intermediate 17, except that the reagent 5-bromo-1-pentanol was replaced by 5-iodo-3-methylpentan-1-ol. ¹H NMR (500 MHz, CDCl₃) δ 0.91 (d, J=6.5 Hz, 3H), 1.19 (s, 9H), 1.42 (qd, J=7.0, 14.0 Hz, 1H), 1.52-1.61 (m, 2H), 1.68-1.84 (m, 2H), 1.97 (br s, 1H), 2.77 (s, 3H), 3.58-3.69 (m, 2H), 4.22-4.32 (m, 2H).

Intermediate 29

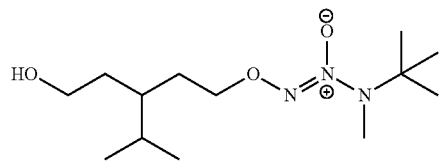

O²-[3-(2-hydroxyethyl)-4-methylpentyl]1-(N-tert-butylmethylamino)diazen-1-ium-1,2-diolate The title compound was prepared by following the procedure for intermediate 28, except that the reagent 3-methyl-1,5-pentanediol was replaced by 3-isopropylpentane-1,5-diol (prepared as described in Irwin, A. J.; Jones, J. B. *J. Am. Chem. Soc.* 1977, 99, 556-561.). ¹H NMR (500 MHz, CDCl₃) δ 0.88 (d, J=6.5 Hz, 6H), 1.25 (s, 9H), 1.37-1.46 (m, 1H), 1.60-1.84 (m, 5H), 1.98 (br s, 1H), 2.82 (s, 3H), 3.64-3.72 (m, 2H), 4.25-4.37 (m, 2H).

Intermediate 30

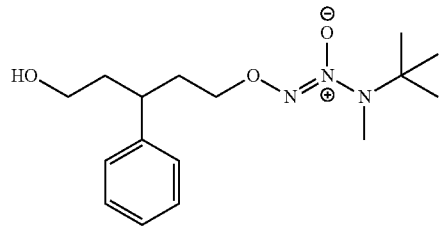

O²-(5-hydroxy-3-phenylpentyl) 1-(N-tert-butylmethylamino)diazen-1-ium-1,2-diolate Step A: 3-phenylpentane-1,5-diol 3-Phenylglutaric acid (3.39 g, 16.3 mmol) was dissolved in tetrahydrofuran (163 mL) and cooled to 0° C. A 1.0 M tetrahydrofuran solution of borane tetrahydrofuran complex (65 mL, 65 mmol) was added dropwise, and the reaction was allowed to warm to room temperature overnight. The reaction was cooled to 0° C., quenched with methanol slowly, followed by water, and concentrated in vacuo. The resulting solid was stirred with 1N hydrochloric acid for 20 minutes. The solution was extracted into ethyl acetate. The combined organic layers were dried (magnesium sulfate), filtered, and concentrated in vacuo. The residue was purified by column chromatography on silica gel, eluting with ethyl acetate to give the title compound as a colorless oil. ¹H NMR (500 MHz, CDCl₃) δ 1.75-1.86 (m, 2H), 1.86-1.96 (m, 2H), 2.45 (br s, 2H), 2.87-2.95 (m, 1H), 3.39-3.48 (m, 2H), 3.49-3.57 (m, 2H), 7.15-7.22 (m, 3H), 7.25-7.31 (m, 2H).

Step B: 5-bromo-3-phenylpentan-1-ol

3-Phenylpentane-1,5-diol (452 mg, 2.51 mmol) was dissolved in 48% aqueous hydrobromic acid (284 μL, 2.51 mmol) and toluene (2.5 mL), placed in a sealed tube, and heated in a microwave oven at 180° C. for 10 minutes. The mixture was cooled and purified by column chromatography on silica gel, eluting with 0-100% ethyl acetate/hexanes to give the title compound as a colorless oil. $^1$H NMR (500 MHz, CDCl$_3$) δ 1.57 (br s, 1H), 1.81-1.97 (m, 2H), 2.08-2.23 (m, 2H), 2.97 (quintet, J=5.0 Hz, 1H), 3.06-3.14 (m, 1H), 3.24-3.31 (m, 1H), 3.42-3.49 (m, 1H), 3.49-3.56 (m, 1H), 7.17-7.25 (m, 3H), 7.28-7.33 (m, 2H).

Step C: O$^2$-(5-hydroxy-3-phenylpentyl) 1-(N-tert-butylmethylamino)diazen-1-ium-1,2-diolate The title compound was prepared by following the procedure for intermediate 17, except that the reagent 5-bromo-1-pentanol was replaced by 5-bromo-3-phenylpentan-1-ol. $^1$H NMR (500 MHz, CDCl$_3$) δ 1.23 (s, 9H), 1.83-2.06 (m, 4H), 2.15-2.24 (m, 1H), 2.97 (s, 3H), 3.43-3.51 (m, 1H), 3.51-3.57 (m, 1H), 4.04-4.15 (m, 2H), 7.16-7.24 (m, 3H), 7.27-7.32 (m, 2H).

Intermediate 31

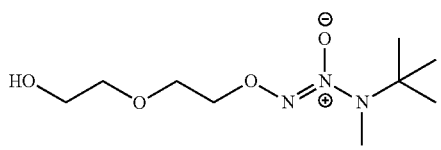

O$^2$-[2-(2-hydroxyethoxy)ethyl] 1-(N-tert-butylmethylamino)diazen-1-ium-1,2-diolate Step A: 2-(2-bromoethoxy)ethanol Phosphorus tribromide (1.19 mL, 12.6 mmol) was dissolved in diethylene glycol (10.0 mL, 105 mmol) at 0° C., placed in a sealed tube and heated in a microwave oven at 180° C. for 5 minutes. The mixture was cooled and purified by column chromatography on silica gel, eluting with 0-100% ethyl acetate/hexanes to give the title compound as a colorless oil. $^1$H NMR (500 MHz, CDCl$_3$) δ 2.36 (br s, 1H), 3.48 (t, J=6.0 Hz, 2H), 3.61 (t, J=4.5 Hz, 2H), 3.73 (q, J=4.5 Hz, 2H), 3.80 (t, J=6.0 Hz, 2H).

Step B: O$^2$-[2-(2-hydroxyethoxy)ethyl] 1-(N-tert-butylmethylamino)diazen-1-ium-1,2-diolate The title compound was prepared by following the procedure for intermediate 17, except that the reagent 5-bromo-1-pentanol was replaced by 2-(2-bromoethoxy)ethanol.

Intermediate 32

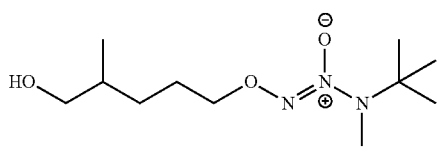

O$^2$-(5-hydroxy-4-methylpentyl) 1-(N-tert-butylmethylamino)diazen-1-ium-1,2-diolate The title compound was prepared by following the procedure for intermediate 27, except that the reagent ethyl 4-methyl-4-pentenoate was replaced by ethyl 2-methyl-4-pentenoate. $^1$H NMR (500 MHz, CDCl$_3$) δ 0.92 (d, J=6.9 Hz, 3H), 1.23 (s, 9H), 1.47-1.54 (m, 2H), 1.60-1.90 (m, 3H), 2.80 (s, 3H), 3.41-3.52 (m, 2H), 4.25 (t, J=6.8 Hz, 2H).

Intermediate 33

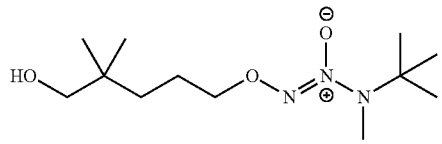

O$^2$-(5-hydroxy-4,4-dimethylpentyl) 1-(N-tert-butylmethylamino)diazen-1-ium-1,2-diolate The title compound was prepared by following the procedure for intermediate 27, except that the reagent ethyl 4-methyl-4-pentenoate was replaced by methyl 2,2-dimethyl-4-pentenoate (prepared as described in Wender, P. A.; Koehler, M. F. T.; Sendzik, M. *Org. Lett.* 2003, 5, 4549-4552.). $^1$H NMR (500 MHz, CDCl$_3$) δ 0.87 (s, 6H), 1.23 (s, 9H), 1.30-1.34 (m, 2H), 1.70-1.77 (m, 2H), 2.80 (s, 3H), 3.31 (s, 2H), 4.23 (t, J=6.8 Hz, 2H).

Intermediate 34

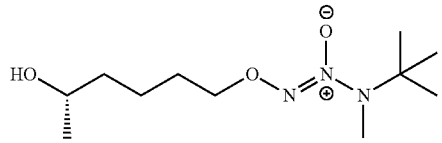

O$^2$-[(5S)-5-hydroxyhexyl] 1-(N-tert-butylmethylamino)diazen-1-ium-1,2-diolate

Step A: O$^2$-(5-oxohexyl) 1-(N-tert-butylmethylamino)diazen-1-ium-1,2-diolate

The title compound was prepared by following the procedure for intermediate 17, except that the reagent 5-bromo-1-pentanol was replaced by 6-bromohexan-2-one (prepared as described in Zhang, W.-C.; Li, C.-J. *J. Org. Chem.* 2000, 65, 5831-5833.). $^1$H NMR (500 MHz, CDCl$_3$) δ 1.22 (s, 9H), 1.66 (quintet, J=8.6 Hz, 2H), 1.76 (quintet, J=8.6 Hz, 2H), 2.12 (s, 3H), 2.46 (t, J=7.2 Hz, 2H), 2.80 (s, 3H), 4.24 (t, J=6.6 Hz, 2H).

Step B: O$^2$-[(5S)-5-hydroxyhexyl] 1-(N-tert-butylmethylamino)diazen-1-ium-1,2-diolate O$^2$-(5-oxohexyl) 1-(N-tert-butylmethylamino)diazen-1-ium-1,2-diolate (900 mg, 3.67 mmol) was added to a 0.1 M pH 7 phosphate buffer (81 mL) containing isopropanol (9 mL), reduced nicotinamide adenine dinucleotide phosphate (450 mg), and KRED NAD 101 (450 mg). The reaction mixture was stirred for 24 hours at 30° C. The aqueous layer was centrifuged with ethyl acetate (3×90 mL) for extraction. The combined organic extracts were concentrated in vacuo, and the residue was purified by column chromatography on silica gel, eluting with 0-100% ethyl acetate/hexanes to give the title compound as a yellow oil. $^1$H NMR (500 MHz, CDCl$_3$) δ 1.18 (d, J=6.2 Hz, 3H), 1.23 (s, 9H), 1.37 (s, 1H), 1.39-1.53 (m, 4H), 1.74-1.81 (m, 2H), 2.81 (s, 3H), 3.80 (sextet, J=6.0 Hz, 1H), 4.26 (t, J=6.8 Hz, 2H); t$_R$ (ChiralPak AS, 5/95 isopropanol/heptane, 0.75 mL/min) 12.9 min.

Intermediate 35

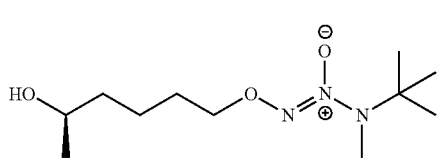

O$^2$-[(5R)-5-hydroxyhexyl] 1-(N-tert-butylmethylamino)diazen-1-ium-1,2-diolate

The title compound was prepared by following the procedure for intermediate 34, except that the enzyme KRED NAD 101 was replaced by Biocatalytics enzyme EXP-A1C; t$_R$ (ChiralPal AS, 5/95 isopropanol/heptane, 0.75 mL/min) 11.8 min.

Intermediate 36

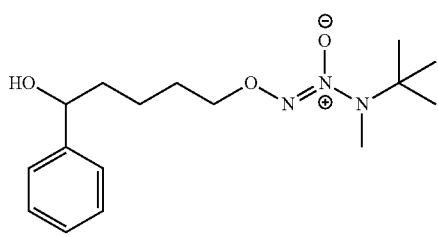

O$^2$-(5-hydroxy-5-phenylpentyl) 1-(N-tert-butylmethylamino)diazen-1-ium-1,2-diolate Step A: O$^2$-(5-oxo-5-phenylpentyl) 1-(N-tert-butylmethylamino)diazen-1-ium-1,2-diolate The title compound was prepared by following the procedure for intermediate 17, except that the reagent 5-bromo-1-pentanol was replaced by 5-bromo-1-phenylpentan-1-one (prepared as described in Sonda, S.; Katayama, K.; Kawahara, T.; Sato, N.; Asano, K. Bioorg. Med. Chem. 2004, 12, 2737-2747.). $^1$H NMR (500 MHz, CDCl$_3$) δ 1.23 (s, 9H), 1.83-1.89 (m, 4H), 2.80 (s, 3H), 3.02 (t, J=6.9 Hz, 2H), 4.30 (t, J=6.2 Hz, 2H), 7.46 (t, J=6.5 Hz, 2H), 7.56 (t, J=7.4 Hz, 1H), 7.95 (d, J=7.1 Hz, 2H).

Step B: O$^2$-(5-hydroxy-5-phenylpentyl) 1-(N-tert-butylmethylamino)diazen-1-ium-1,2-diolate The title compound was prepared by following step A for intermediate 26, except that the reagent 1-phenylpentane-1,5-diol was replaced by O$^2$-(5-oxo-5-phenylpentyl) 1-(N-tert-butylmethylamino)diazen-1-ium-1,2-diolate. $^1$H NMR (500 MHz, CDCl$_3$) δ 1.22 (s, 9H), 1.32-1.52 (m, 2H), 1.77 (quintet, J=6.0 Hz, 2H), 1.80-2.05 (m, 2H), 2.80 (s, 3H), 4.23 (t, J=6.9 Hz, 2H), 4.66 (dt, J=1.6, 5.7 Hz, 1H), 7.24-7.29 (m, 1H), 7.31-7.38 (m, 4H).

Intermediate 37

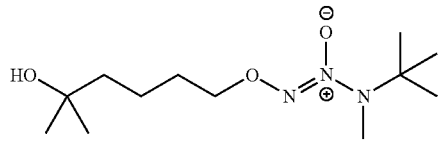

O$^2$-(5-hydroxy-5-methylhexyl) 1-(N-tert-butylmethylamino)diazen-1-ium-1,2-diolate A 3.0 M diethyl ether solution of methylmagnesium bromide (0.80 mL, 2.40 mmol) was added to a diethyl ether solution (20 mL) of O$^2$-(5-oxohexyl) 1-(N-tert-butylmethylamino)diazen-1-ium-1,2-diolate (synthesized by following step A for intermediate 34, 587 mg, 2.39 mmol) at 0° C. The reaction mixture was stirred for 2 hours, quenched with saturated aqueous ammonium chloride (10 mL), and extracted with diethyl ether (2×15 mL). The combined organic extracts were concentrated in vacuo, and the residue was purified by column chromatography on silica gel, eluting with 0-100% ethyl acetate/hexanes to give the title compound as a colorless oil. $^1$H NMR (500 MHz, CDCl$_3$) δ 1.19 (s, 6H), 1.22 (s, 9H), 1.41-1.50 (m, 4H), 1.76 (quintet, J=7.1 Hz, 2H), 2.80 (s, 3H), 4.26 (t, J=6.9 Hz, 2H).

Intermediate 38

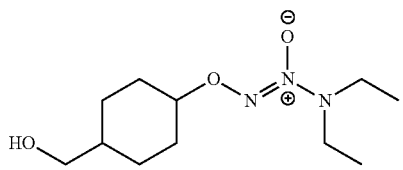

O$^2$-[4-(hydroxymethyl)cyclohexyl] 1-(N,N-diethylamino)diazen-1-ium-1,2-diolate Step A: Ethyl 4-[(methylsulfonyl)oxy]cyclohexanecarboxylate Methanesulfonyl chloride (2.4 mL, 31 mmol) was slowly added to a dichloromethane solution (75 mL) of ethyl 4-hydroxycyclohexanecarboxylate (4.63 mL, 28.7 mmol) and triethylamine (8.2 mL, 59 mmol) at 0° C. The reaction mixture was stirred for 30 minutes, concentrated in vacuo and diluted in diethyl ether (100 mL). The solution was washed with 10% hydrochloric acid (25 mL), water (25 mL), and saturated sodium bicarbonate (15 mL). The organics were dried (magnesium sulfate) and concentrated in vacuo to afford the title compound. $^1$H NMR (500 MHz, CDCl$_3$) δ 1.23 (t, J=7.1 Hz, 3H), 1.54-1.82 (m, 4H), 1.87-1.97 (m, 2H), 2.00-2.08 (m, 2H), 2.34-2.41 (m, 1H), 3.00 (s, 3H), 4.13 (q, J=7.1 Hz, 2H), 4.88-4.92 (m, 1H).

Step B: O²-[4-(ethoxycarbonyl)cyclohexyl] 1-(N,N-diethylamino)diazen-1-ium-1,2-diolate The title compound was prepared by following the procedure for intermediate 6, except that the reagent 3-bromopropan-1-ol was replaced by ethyl 4-[(methylsulfonyl)oxy] cyclohexanecarboxylate. ¹H NMR (500 MHz, CDCl₃) δ 1.08 (t, J=7.1 Hz, 6H), 1.25 (t, J=7.1 Hz, 3H), 1.52-1.62 (m, 3H), 1.68-1.80 (m, 1H), 2.04-2.11 (m, 2H), 2.18-2.24 (m, 2H), 2.25-2.34 (m, 1H), 3.06 (q, J=7.1 Hz, 4H), 4.12 (q, J=7.1 Hz, 2H), 4.23-4.30 (m, 1H).

Step C: O²-[4-(hydroxymethyl)cyclohexyl] 1-(N,N-diethylamino)diazen-1-ium-1,2-diolate The title compound was prepared by following step A for intermediate 26, except that the reagent methyl 5-oxo-5-phenylpentanoate was replaced by O²-[4-(ethoxycarbonyl)cyclohexyl] 1-(N,N-diethylamino)diazen-1-ium-1,2-diolate. ¹H NMR (500 MHz, CDCl₃) δ 1.08 (t, J=7.1 Hz, 6H), 1.01-1.10 (m, 2H), 1.46-1.58 (m, 2H), 1.65-1.70 (m, 1H), 1.86-1.93 (m, 2H), 2.16-2.23 (m, 2H), 3.07 (q, J=7.1 Hz, 4H), 4.04 (d, J=6.0 Hz, 2H), 4.18 (m, 1H).

Intermediate 39

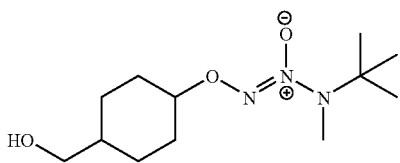

O²-[4-(hydroxymethyl)cyclohexyl] 1-(N-tert-butylmethylamino)diazen-1-ium-1,2-diolate The title compound was prepared by following the procedure for intermediate 38, except that the reagent sodium 1-(N,N-diethylamino)diazen-1-ium-1,2-diolate was replaced by sodium 1-(N-tert-butylmethylamino)diazen-1-ium-1,2-diolate. ¹H NMR (500 MHz, CDCl₃) δ 1.01-1.10 (m, 2H), 1.22 (s, 9H), 1.46-1.58 (m, 2H), 1.65-1.70 (m, 1H), 1.86-1.93 (m, 2H), 2.16-2.23 (m, 2H), 2.80 (s, 3H), 3.47 (d, J=6.0 Hz, 2H), 4.18-4.25 (m, 1H).

Intermediate 40

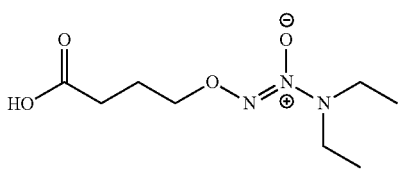

O²-[3-(carboxylato)propyl] 1-(N,N-diethylamino)diazen-1-ium-1,2-diolate

Step A: O²-[3-(methoxycarbonyl)propyl] 1-(N,N-diethylamino)diazen-1-ium-1,2-diolate The title compound was prepared by following the procedure for intermediate 6, except that the reagent 3-bromopropan-1-ol was replaced by methyl 4-bromobutyrate. ¹H NMR (500 MHz, CDCl₃) δ 1.09 (t, J=7.1 Hz, 6H), 2.08 (quintet, J=6.9 Hz, 2H), 2.44 (t, J=7.3 Hz, 2H), 3.09 (q, J=7.1 Hz, 4H), 3.67 (s, 3H), 4.31 (t, J=6.3 Hz, 2H).

Step B: O²-[3-(carboxylato)propyl] 1-(N,N-diethylamino)diazen-1-ium-1,2-diolate

To a methanol solution (10 mL) of O²-[3-(methoxycarbonyl)propyl] 1-(N,N-diethylamino) diazen-1-ium-1,2-diolate (170 mg, 0.73 mmol) was added a 4.0 M sodium hydroxide (2.0 mL, 8.0 mmol) solution. After stirring for 2 days, the reaction mixture was acidified with 1.0 M hydrochloric acid and extracted with diethyl ether (3×50 mL). The combined organic extracts were concentrated in vacuo to afford the title compound as a colorless liquid. ¹H NMR (500 MHz, CDCl₃) δ 1.09 (t, J=7.1 Hz, 6H), 2.09 (quintet, J=6.8 Hz, 2H), 2.50 (t, J=7.4 Hz, 2H), 3.09 (q, J=7.2 Hz, 4H), 4.33 (t, J=6.3 Hz, 2H).

Intermediate 41

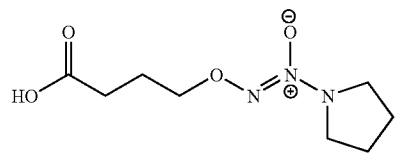

O²-[3-(carboxylato)propyl] 1-(pynolidin-1-yl)diazen-1-ium-1,2-diolate

The title compound was prepared by following the procedure for intermediate 40, except that the reagent sodium 1-(N,N-diethylamino)diazen-1-ium-1,2-diolate was replaced by sodium 1-(pyrrolidin-1-yl)diazen-1-ium-1,2-diolate. ¹H NMR (500 MHz, CDCl₃) δ 1.96-2.00 (m, 4H), 2.01 (quintet, J=6.0 Hz, 2H), 2.55 (t, J=6.0 Hz, 2H), 3.55 (t, J=7.0 Hz, 4H), 4.34 (t, J=6.0 Hz, 2H).

Intermediate 42

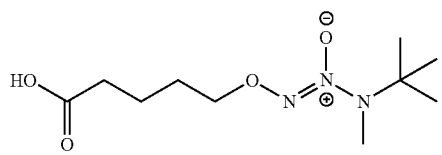

O²-[4-(carboxylato)butyl] 1-(N-tert-butylmethylamino)diazen-1-ium-1,2-diolate

The title compound was prepared by following step B for intermediate 22, except that the reagent O²-(5-(benzyloxy)pentyl) 1-[2-(hydroxymethyl)pyrrolidin-1-yl]diazen-1-ium-1,2-diolate was replaced by O²-(5-hydroxypentyl) 1-(N-tert-butylmethylamino)diazen-1-ium-1,2-diolate. ¹H NMR (500 MHz, CDCl₃) δ 1.21 (s, 9H), 1.68-1.76 (m, 2H), 1.76-1.84 (m, 2H), 2.37 (t, J=7.0 Hz, 2H), 2.78 (s, 3H), 4.25 (t, J=6.5 Hz, 2H).

Example 1

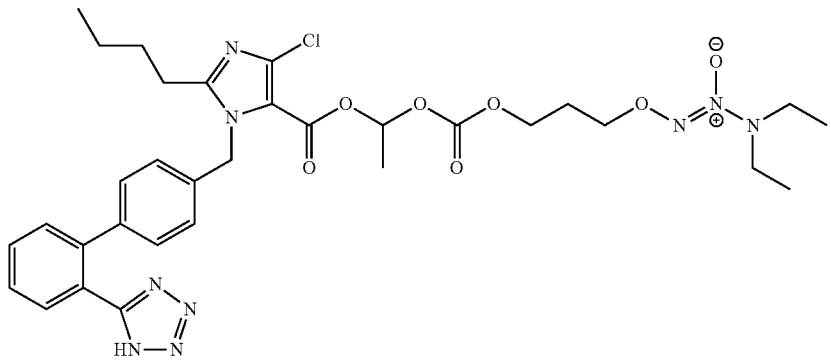

O²-(3-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}propyl) 1-(N,N-diethylamino)diazen-1-ium-1,2-diolate

Step A: O²-(3-{[(1-chloroethoxy)carbonyl]oxy}propyl) 1-(N,N-diethylamino)diazen-1-ium-1,2-diolate To a dichloromethane (10 mL) solution of 1-chloroethyl chloroformate (120 µL, 1.10 mmol) and O²-(3-hydroxypropyl) 1-(N,N-diethylamino)diazen-1-ium-1,2-diolate (intermediate 6, 172 mg, 0.899 mmol) at room temperature was added pyridine (182 µL, 2.25 mmol). After 16 hours, the reaction mixture was concentrated in vacuo, and the residue was purified by column chromatography on silica gel, eluting with 25/75→65/35 ethyl acetate/hexanes to give the title compound as a colorless liquid. ¹H NMR (500 MHz, CDCl₃) δ 1.09 (t, J=7.1 Hz, 6H), 1.82 (d, J=5.7 Hz, 3H), 2.16 (quintet, J=6.3 Hz, 2H), 3.09 (q, J=7.1 Hz, 4H), 4.32 (t, J=6.2 Hz, 2H), 4.37 (t, J=6.3 Hz, 2H), 6.41 (q, J=5.8 Hz, 1H).

Step B: O²-(3-{[(1-{[(2-butyl-4-chloro-1-{[2'-(1-trityl-1H-tetrazol-5-yl)biphenyl-4-yl]methyl}-1H-imidazol-5-yl)carbonyl]oxy}ethoxy)carbonyl]oxy}propyl) 1-(N,N-diethylamino)diazen-1-ium-1,2-diolate A mixture of 2-butyl-4-chloro-1-{[2'-(1-trityl-1H-tetrazol-5-yl)biphenyl-4-yl]methyl}-1H-imidazole-5-carboxylic acid (922 mg, 1.36 mmol) and cesium carbonate (656 mg, 2.02 mmol) was charged with a N,N-dimethylformamide (10 mL) solution of O²-(3-{[(1-chloroethoxy) carbonyl]oxy}propyl) 1-(N,N-diethylamino)diazen-1-ium-1,2-diolate (270 mg, 0.90 mmol). It was heated with microwaves (100° C., 10 minutes), and the reaction mixture was purified by column chromatography, eluting with 10/90→70/30 ethyl acetate/hexanes to give the title compound as a white solid. ¹H NMR (500 MHz, CDCl₃) δ 0.89 (t, J=7.3 Hz, 3H), 1.04 (t, J=7.1 Hz, 6H), 1.36 (sextet, J=7.4 Hz, 2H), 1.60 (d, J=5.4 Hz, 3H), 1.68 (quintet, J=7.7 Hz, 2H), 2.06 (quintet, J=6.3 Hz, 2H), 2.66 (t, J=7.8 Hz, 2H), 3.07 (q, J=7.1 Hz, 4H), 4.15-4.24 (m, 2H), 4.26 (t, J=6.3 Hz, 2H), 5.29 (d, J=16.2 Hz, 1H), 5.55 (d, J=16.2 Hz, 1H), 6.79 (d, J=8.0 Hz, 2H), 6.86 (q, J=5.5 Hz, 1H), 6.92 (d, J=7.8 Hz, 6H), 7.09 (d, J=8.2 Hz, 2H), 7.25 (t, J=7.8 Hz, 6H), 7.30-7.36 (m, 4H), 7.43-7.50 (m, 2H), 7.90 (dd, J=1.2, 7.5 Hz, 1H); LC-MS (M+H) found 940.5.

Step C: O²-(3-{[(1-{[(2-butyl-4-chloro-1-{[2'-(1-trityl-1H-tetrazol-5-yl)biphenyl-4-yl]methyl}-1H-imidazol-5-yl)carbonyl]oxy}ethoxy)carbonyl]oxy}propyl) 1-(N,N-diethylamino)diazen-1-ium-1,2-diolate A methanol (10 mL) solution of O²-(3-{[(1-{[(2-butyl-4-chloro-1-{[2'-(1-trityl-1H-tetrazol-5-yl)biphenyl-4-yl]methyl}-1H-imidazol-5-yl)carbonyl]oxy}ethoxy)carbonyl]oxy}propyl) 1-(N,N-diethylamino)diazen-1-ium-1,2-diolate (815 mg, 0.867 mmol) was heated to 70° C. for 2 hours. The reaction mixture was concentrated in vacuo, and the residue was purified by column chromatography, eluting with 1/99→10/90 methanol/dichloromethane to give the title compound as a white solid. ¹H NMR (500 MHz, CDCl₃) δ 0.89 (t, J=7.3 Hz, 3H), 1.04 (t, J=7.1 Hz, 6H), 1.36 (sextet, J=7.4 Hz, 2H), 1.60 (d, J=5.4 Hz, 3H), 1.68 (quintet, J=7.7 Hz, 2H), 2.06 (quintet, J=6.3 Hz, 2H), 2.66 (t, J=7.8 Hz, 2H), 3.07 (q, J=7.1 Hz, 4H), 4.15-4.24 (m, 2H), 4.26 (t, J=6.3 Hz, 2H), 5.39 (d, J=16.4 Hz, 1H), 5.62 (d, J=16.5 Hz, 1H), 6.85 (q, J=5.4 Hz, 1H), 6.96 (d, J=8.0 Hz, 2H), 7.15 (d, J=8.2 Hz, 2H), 7.43 (d, J=7.3 Hz, 1H), 7.52 (t, J=7.7 Hz, 1H), 7.59 (dt, J=1.3, 7.7 Hz, 1H), 7.94 (d, J=7.7 Hz, 1H); LC-MS (M+H) found 698.3. Chromatography of the racemic mixture over Chiralpak AD column, eluting with methanol/carbon dioxide, afforded the separate enantiomers.

Example 2

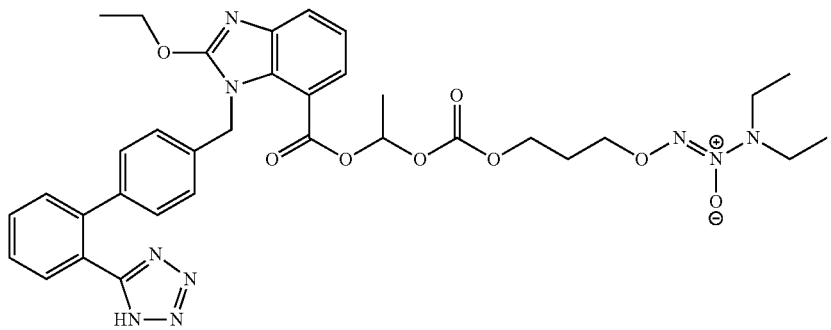

$O^2$-(3-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}propyl) 1-(N,N-diethylamino)diazen-1-ium-1,2-diolate The title compound was prepared by following the procedure for example 1, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. $^1$H NMR (500 MHz, CDCl$_3$) δ 1.05 (t, J=7.4 Hz, 6H), 1.47 (t, J=7.0 Hz, 3H), 1.52 (d, J=5.3 Hz, 3H), 1.95-2.05 (m, 2H), 3.09 (q, J=7.1 Hz, 4H), 4.12-4.21 (m, 2H), 4.25 (t, J=6.3 Hz, 2H), 4.40-4.43 (m, 1H), 4.52-4.56 (m, 1H), 5.57 (d, J=16.4 Hz, 1H), 5.69 (d, J=16.4 Hz, 1H), 6.76 (q, J=5.5 Hz, 1H), 6.87 (d, J=7.7 Hz, 2H), 6.95 (d, J=8.0 Hz, 2H), 7.05 (t, J=7.8 Hz, 1H), 7.34 (dd, J=1.8, 7.3 Hz, 1H), 7.52-7.57 (m, 4H), 7.97 (dd, J=2.0, 7.4 Hz, 1H); LC-MS (M+H) found 702.3. Chromatography of the racemic mixture over Chiralpak AD column, eluting with isopropanol/carbon dioxide, afforded the separate enantiomers.

Example 3

$O^2$-(3-{[(1-{[2-butyl-4-chloro-1-{[2'-(1H-tetrazol-5-yl)biphenyl-4-yl]methyl}-1H-imidazol-5-yl)carbonyl]oxy}ethoxy)carbonyl]oxy}propyl) 1-(N-ethylisopropylamino)diazen-1-ium-1,2-diolate The title compound was prepared by following the procedure for example 1, except that the reagent $O^2$-(3-hydroxypropyl) 1-(N,N-diethylamino)diazen-1-ium-1,2-diolate (intermediate 6) was replaced by $O^2$-(3-hydroxypropyl) 1-(N-ethylisopropylamino)diazen-1-ium-1,2-diolate (intermediate 7). $^1$H NMR (500 MHz, CDCl$_3$) δ 0.89 (t, J=7.3 Hz, 3H), 1.00 (t, J=6.9 Hz, 3H), 1.09 (d, J=6.4 Hz, 6H), 1.37 (sextet, J=7.6 Hz, 2H), 1.60 (d, J=5.5 Hz, 3H), 1.69 (quintet, J=7.6 Hz, 2H), 2.05 (quintet, J=6.2 Hz, 2H), 2.64 (t, J=8.0 Hz, 2H), 3.05 (q, J=7.1 Hz, 2H), 3.37 (septet, J=6.4 Hz, 1H), 4.20-4.28 (m, 2H), 4.34 (t, J=6.2 Hz, 2H), 5.28 (d, J=16.5 Hz, 1H), 5.56 (d, J=16.2 Hz, 1H), 6.86 (q, J=5.5 Hz, 1H), 6.96 (d, J=8.1 Hz, 2H), 7.15 (d, J=8.3 Hz, 2H), 7.43 (d, J=7.7 Hz, 1H), 7.51 (t, J=7.6 Hz, 1H), 7.58 (t, J=7.3 Hz, 1H), 7.93 (d, J=7.5 Hz, 1H); LC-MS (M+H) found 713.0.

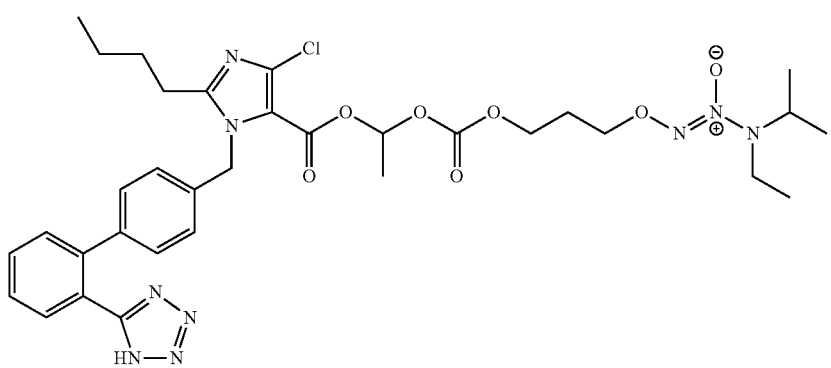

Example 4

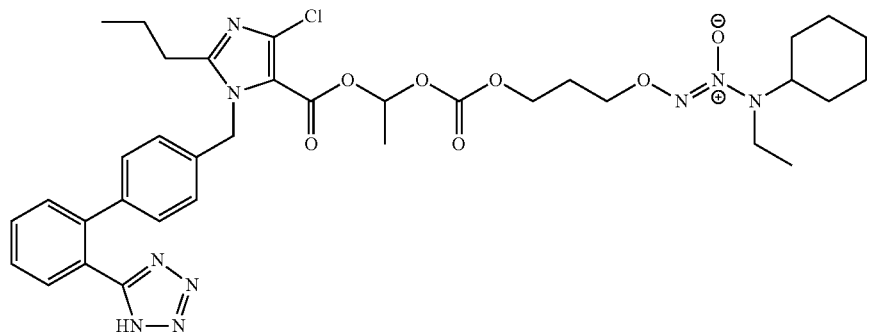

O²-(3-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}propyl) 1-(N-ethylcyclohexylamino)diazen-1-ium-1,2-diolate The title compound was prepared by following the procedure for example 1, except that the reagent O²-(3-hydroxypropyl) 1-(N,N-diethylamino)diazen-1-ium-1,2-diolate (intermediate 6) was replaced by O²-(3-hydroxypropyl) 1-(N-ethylcyclohexylamino)diazen-1-ium-1,2-diolate (intermediate 8). ¹H NMR (500 MHz, CDCl₃) δ 0.90 (t, J=7.3 Hz, 3H), 0.99 (t, J=6.8 Hz, 3H), 1.08-1.18 (m, 1H), 1.18-1.30 (m, 4H), 1.37 (sextet, J=7.6 Hz, 2H), 1.60 (d, J=5.5 Hz, 3H), 1.58-1.64 (m, 1H), 1.69 (quintet, J=7.5 Hz, 2H), 1.72-1.80 (m, 4H), 2.05 (quintet, J=6.1 Hz, 2H), 2.65 (t, J=7.3 Hz, 2H), 2.96-3.02 (m, 1H), 3.05 (q, J=7.1 Hz, 2H), 4.13-4.23 (m, 2H), 4.25 (t, J=6.4 Hz, 2H), 5.38 (d, J=16.2 Hz, 1H), 5.65 (d, J=16.5 Hz, 1H), 6.86 (q, J=5.4 Hz, 1H), 6.97 (d, J=8.2 Hz, 2H), 7.16 (d, J=8.0 Hz, 2H), 7.43 (dd, J=1.1, 7.8 Hz, 1H), 7.52 (dt, J=1.2, 7.6 Hz, 1H), 7.58 (dt, J=1.3, 7.5 Hz, 1H), 7.96 (dd, J=0.9, 7.8 Hz, 1H); LC-MS (M+H) found 751.7.

Example 5

O²-(3-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}propyl) 1-(N-tert-butylmethylamino)diazen-1-ium-1,2-diolate The title compound was prepared by following the procedure for example 1, except that the reagent O²-(3-hydroxypropyl) 1-(N,N-diethylamino)diazen-1-ium-1,2-diolate (intermediate 6) was replaced by O²-(3-hydroxypropyl) 1-(N-tert-butylmethylamino)diazen-1-ium-1,2-diolate (intermediate 9). ¹H NMR (500 MHz, CDCl₃) δ 0.90 (t, J=7.5 Hz, 3H), 1.18 (s, 9H), 1.37 (sextet, J=7.5 Hz, 2H), 1.61 (d, J=5.3 Hz, 3H), 1.70 (quintet, J=7.8 Hz, 2H), 2.05 (quintet, J=6.2 Hz, 2H), 2.66 (t, J=7.5 Hz, 2H), 2.75 (s, 3H), 4.10-4.20 (m, 2H), 4.25 (t, J=6.2 Hz, 2H), 5.39 (d, J=16.5 Hz, 1H), 5.63 (d, J=16.5 Hz, 1H), 6.86 (q, J=5.5 Hz, 1H), 6.96 (d, J=8.2 Hz, 2H), 7.15 (d, J=8.2 Hz, 2H), 7.43 (d, J=8.2 Hz, 1H), 7.50 (dt, J=1.2, 7.3 Hz, 1H), 7.57 (dt, J=1.3, 7.5 Hz, 1H), 7.93 (d, J=7.6 Hz, 1H); LC-MS (M+H) found 712.2.

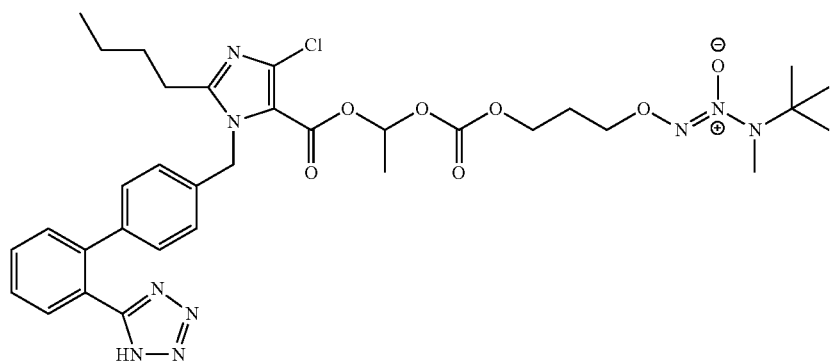

Example 6

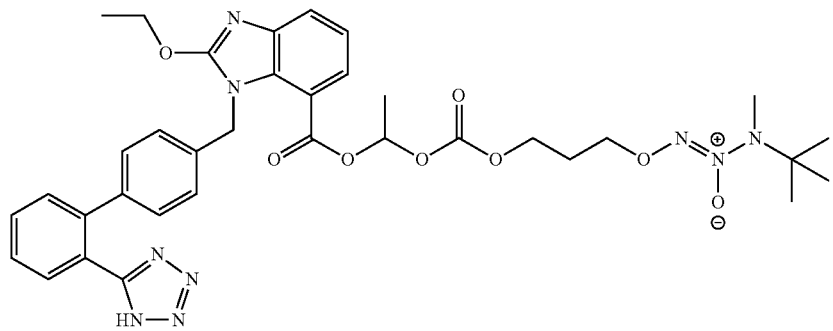

O²-(3-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}propyl) 1-(N-tert-butylmethylamino)diazen-1-ium-1,2-diolate The title compound was prepared by following the procedure for example 5, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. ¹H NMR (500 MHz, CDCl₃) δ 1.19 (s, 9H), 1.46 (t, J=7.1 Hz, 3H), 1.50 (d, J=5.2 Hz, 3H), 1.98-2.04 (m, 2H), 2.77 (s, 3H), 4.10-4.22 (m, 2H), 4.24 (t, J=6.2 Hz, 2H), 4.43-4.60 (m, 2H), 5.57 (d, J=16.7 Hz, 1H), 5.70 (d, J=16.7 Hz, 1H), 6.78 (q, J=5.5 Hz, 1H), 6.89 (d, J=8.2 Hz, 2H), 6.97 (d, J=8.2 Hz, 2H), 7.08 (t, J=8.0 Hz, 1H), 7.35 (dd, J=1.2, 7.3 Hz, 1H), 7.36-7.45 (m, 1H), 7.50-7.60 (m, 3H), 7.96 (dd, J=1.3, 7.5 Hz, 1H); LC-MS (M+H) found 716.3.

Example 7

O²-(3-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}propyl) 1-(N-tert-butylethylamino)diazen-1-ium-1,2-diolate The title compound was prepared by following the procedure for example 1, except that the reagent O²-(3-hydroxypropyl) 1-(N,N-diethylamino)diazen-1-ium-1,2-diolate (intermediate 6) was replaced by O²-(3-hydroxypropyl) 1-(N-tert-butylethylamino)diazen-1-ium-1,2-diolate (intermediate 10). ¹H NMR (500 MHz, CDCl₃) δ 0.90 (t, J=7.6 Hz, 3H), 0.96 (t, J=6.9 Hz, 3H), 1.18 (s, 9H), 1.37 (sextet, J=7.4 Hz, 2H), 1.61 (d, J=5.4 Hz, 3H), 1.70 (quintet, J=7.6 Hz, 2H), 2.05 (quintet, J=6.2 Hz, 2H), 2.66 (t, J=8.2 Hz, 2H), 3.05 (q, J=7.0 Hz, 2H), 4.15-4.22 (m, 2H), 4.15-4.20 (m, 1H), 4.24-4.30 (m, 1H), 5.39 (d, J=16.5 Hz, 1H), 5.63 (d, J=16.5 Hz, 1H), 6.85 (q, J=5.2 Hz, 1H), 6.96 (d, J=8.0 Hz, 2H), 7.15 (d, J=8.2 Hz, 2H), 7.43 (d, J=7.8 Hz, 1H), 7.51 (dt, J=1.1, 7.3 Hz, 1H), 7.58 (dt, J=1.1, 7.3 Hz, 1H), 7.93 (dd, J=1.3, 7.5 Hz, 1H); LC-MS (M+H) found 726.5.

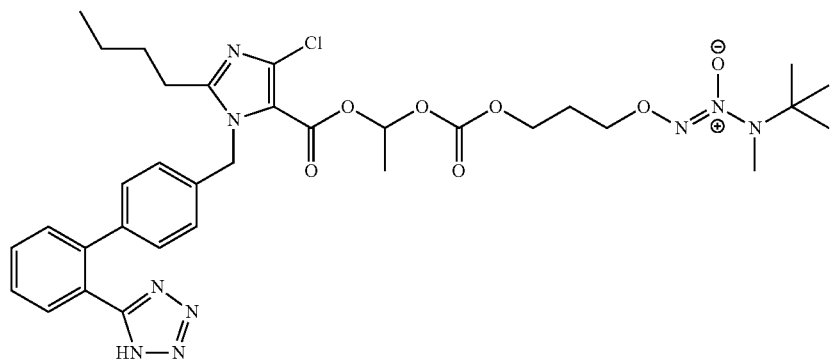

Example 8

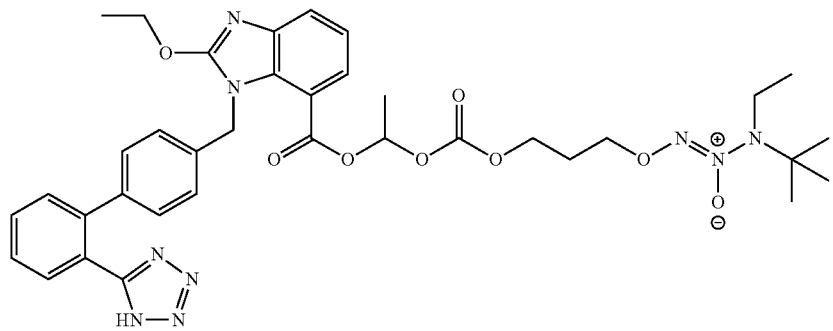

O²-(3-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}propyl) 1-(N-tert-butylethylamino)diazen-1-ium-1,2-diolate The title compound was prepared by following the procedure for example 7, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. $^1$H NMR (500 MHz, CDCl$_3$) δ 0.98 (t, J=7.1 Hz, 3H), 1.19 (s, 9H), 1.47 (t, J=7.1 Hz, 3H), 1.51 (d, J=5.4 Hz, 3H), 1.97-2.05 (m, 2H), 3.08 (q, J=7.1 Hz, 2H), 4.10-4.22 (m, 2H), 4.26 (t, J=6.2 Hz, 2H), 4.44-4.62 (m, 2H), 5.57 (d, J=16.5 Hz, 1H), 5.72 (d, J=16.5 Hz, 1H), 6.79 (q, J=5.5 Hz, 1H), 6.92 (d, J=8.0 Hz, 2H), 6.99 (d, J=8.3 Hz, 2H), 7.10 (t, J=8.0 Hz, 1H), 7.36 (dd, J=1.3, 7.6 Hz, 1H), 7.42-7.49 (m, 1H), 7.51-7.57 (m, 2H), 7.59 (d, J=8.0 Hz, 1H), 7.96 (d, J=7.1 Hz, 1H); LC-MS (M+H) found 730.5.

Example 9

O²-(3-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}propyl) 1-(pyrrolidin-1-yl)diazen-1-ium-1,2-diolate The title compound was prepared by following the procedure for example 1, except that the reagent O²-(3-hydroxypropyl) 1-(N,N-diethylamino)diazen-1-ium-1,2-diolate (intermediate 6) was replaced by O²-(3-hydroxypropyl) 1-(pyrrolidin-1-yl)diazen-1-ium-1,2-diolate (intermediate 11). $^1$H NMR (500 MHz, CDCl$_3$) δ 0.89 (t, J=7.3 Hz, 3H), 1.36 (sextet, J=7.4 Hz, 2H), 1.60 (d, J=5.4 Hz, 3H), 1.68 (quintet, J=7.7 Hz, 2H), 1.85-1.96 (m, 4H), 2.06 (quintet, J=6.3 Hz, 2H), 2.66 (t, J=7.8 Hz, 2H), 3.55 (t, J=7.0 Hz, 4H), 4.15-4.24 (m, 2H), 4.26 (t, J=6.3 Hz, 2H), 5.39 (d, J=16.4 Hz, 1H), 5.62 (d, J=16.5 Hz, 1H), 6.85 (q, J=5.4 Hz, 1H), 6.96 (d, J=8.0 Hz, 2H), 7.15 (d, J=8.2 Hz, 2H), 7.43 (d, J=7.3 Hz, 1H), 7.52 (t, J=7.7 Hz, 1H), 7.59 (dt, J=1.3, 7.7 Hz, 1H), 7.94 (d, J=7.7 Hz, 1H); LC-MS (M+H) found 696.2.

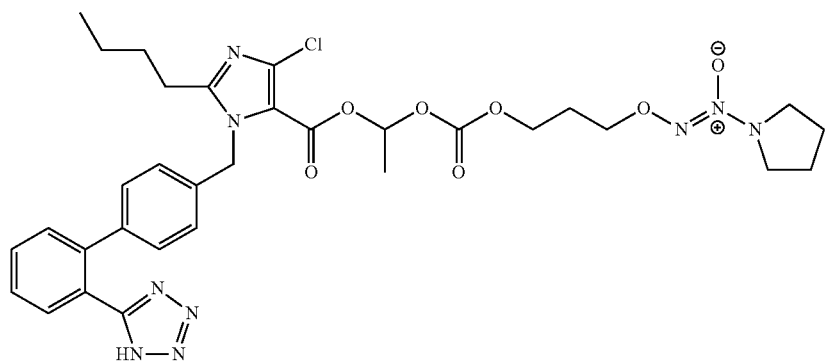

Example 10

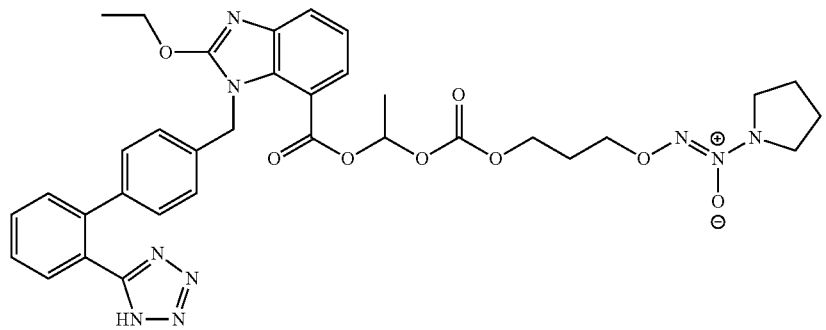

O²-(3-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}propyl) 1-(pyrrolidin-1-yl)diazen-1-ium-1,2-diolate The title compound was prepared by following the procedure for example 9, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. ¹H NMR (500 MHz, CDCl₃) δ 1.46 (t, J=7.0 Hz, 3H), 1.52 (d, J=5.5 Hz, 3H), 1.85-1.93 (m, 4H), 1.95-2.02 (m, 2H), 3.49 (t, J=6.6 Hz, 4H), 4.10-4.20 (m, 4H), 4.40-4.43 (m, 1H), 4.52-4.56 (m, 1H), 5.54 (d, J=16.4 Hz, 1H), 5.71 (d, J=16.4 Hz, 1H), 6.81 (q, J=5.5 Hz, 1H), 6.91 (d, J=8.0 Hz, 2H), 6.97 (d, J=8.3 Hz, 2H), 7.09 (t, J=8.0 Hz, 1H), 7.34 (dd, J=1.8, 7.3 Hz, 1H), 7.42-7.59 (m, 4H), 7.97 (dd, J=2.0, 7.4 Hz, 1H); LC-MS (M+H) found 700.2.

O²-(3-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}propyl) 1-(2-methylpiperidin-1-yl)diazen-1-ium-1,2-diolate The title compound was prepared by following the procedure for example 1, except that the reagent O²-(3-hydroxypropyl) 1-(N,N-diethylamino)diazen-1-ium-1,2-diolate (intermediate 6) was replaced by O²-(3-hydroxypropyl) 1-(pyrrolidin-1-yl)diazen-1-ium-1,2-diolate (intermediate 12). ¹H NMR (500 MHz, CDCl₃) δ 0.89 (t, J=6.2 Hz, 3H), 0.96 (d, J=5.9 Hz, 3H, D1), 0.96 (d, J=5.9 Hz, 3H, D2), 1.20-1.50 (m, 4H), 1.60 (d, J=5.3 Hz, 3H), 1.65-1.74 (m, 4H), 1.74-1.82 (m, 2H), 2.05 (quintet, J=6.0 Hz, 2H), 2.65 (t, J=7.6 Hz, 2H), 3.08-3.20 (m, 3H), 4.14-4.22 (m, 2H), 4.26 (t, J=6.4 Hz, 2H), 5.40 (d, J=16.7 Hz, 1H), 5.60 (d, J=16.4 Hz, 1H), 6.86 (q, J=5.5 Hz, 1H), 6.95 (d, J=7.5 Hz, 2H), 7.14 (d, J=8.1 Hz, 2H), 7.42 (d, J=7.8 Hz, 1H), 7.51 (dt, J=1.1, 7.8 Hz, 1H), 7.58 (dt, J=1.3, 7.6 Hz, 1H), 7.93 (d, J=7.8 Hz, 1H); LC-MS (M+H) found 724.2. Chromatography of the diastereomeric mixture over Chiralpak AD-H column, eluting with isopropanol/carbon dioxide, afforded the four separate diastereomers.

Example 11

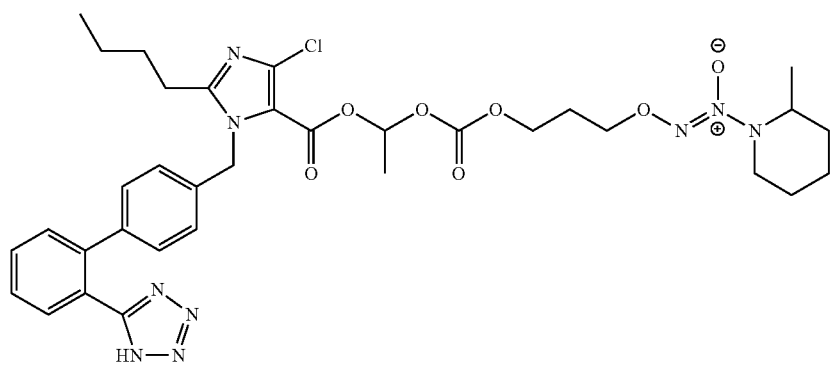

Example 12

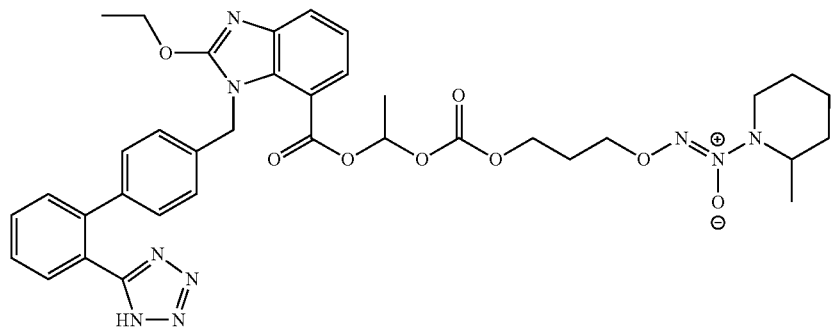

O²-(3-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}propyl) 1-(2-methylpiperidin-1-yl)diazen-1-ium-1,2-diolate The title compound was prepared by following the procedure for example 11, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. $^1$H NMR (500 MHz, CDCl$_3$) δ 0.97 (d, J=6.2 Hz, 3, D1), 0.97 (d, J=6.2 Hz, 3H, D2), 1.20-1.42 (m, 3H), 1.45 (t, J=7.1 Hz, 3H), 1.48 (d, J=6.5 Hz, 3H), 1.66-1.82 (m, 3H), 2.02 (quintet, J=6.1 Hz, 2H, D1), 2.02 (quintet, J=6.1 Hz, 2H, D2), 3.12-3.22 (m, 3H), 4.10-4.22 (m, 2H), 4.25 (t, J=6.2 Hz, 2H), 4.39-4.48 (m, 1H), 4.50-4.59 (m, 1H), 5.57 (d, J=16.7 Hz, 1H), 5.69 (d, J=16.2 Hz, 1H), 6.77 (q, J=5.3 Hz, 1H), 6.88 (d, J=7.7 Hz, 2H), 6.96 (d, J=8.2 Hz, 2H), 7.07 (t, J=8.0 Hz, 1H), 7.32-7.40 (m, 2H), 7.50-7.59 (m, 3H), 7.97 (dd, J=1.6, 7.4 Hz, 1H); LC-MS (M+H) found 728.3.

Example 13

O²-(3-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}propyl) 1-(cis-2,6-dimethylpiperidin-1-yl)diazen-1-ium-1,2-diolate The title compound was prepared by following the procedure for example 1, except that the reagent O²-(3-hydroxypropyl) 1-(N,N-diethylamino)diazen-1-ium-1,2-diolate (intermediate 6) was replaced by O²-(3-hydroxypropyl) 1-(cis-2,6-dimethylpiperidin-1-yl)diazen-1-ium-1,2-diolate (intermediate 13). $^1$H NMR (500 MHz, CDCl$_3$) δ 0.89 (t, J=7.3 Hz, 3H), 0.95 (d, J=5.9 Hz, 6H, D1), 0.95 (d, J=5.9 Hz, 6H, D2), 1.36 (sextet, J=7.6 Hz, 2H), 1.38-1.48 (m, 3H), 1.59 (d, J=5.3 Hz, 3H), 1.52-1.64 (m, 3H), 1.73-1.80 (m, 2H), 2.05 (quintet, J=6.2 Hz, 2H), 2.64 (t, J=7.4 Hz, 2H), 3.05-3.20 (m, 2H), 4.18 (t, J=6.4 Hz, 2H, D1), 4.18 (t, J=6.4 Hz, 2H, D2), 4.29 (t, J=5.9 Hz, 2H), 5.42 (d, J=16.2 Hz, 1H), 5.58 (d, J=16.2 Hz, 1H), 6.86 (q, J=5.3 Hz, 1H), 6.94 (d, J=8.0 Hz, 2H), 7.13 (d, J=8.2 Hz, 2H), 7.42 (dd, J=1.2, 7.8 Hz, 1H), 7.51 (dt, J=1.4, 7.6 Hz, 1H), 7.58 (dt, J=1.4, 7.6 Hz, 1H), 7.91 (dd, J=0.9, 7.3 Hz, 1H); LC-MS (M+H) found 738.3.

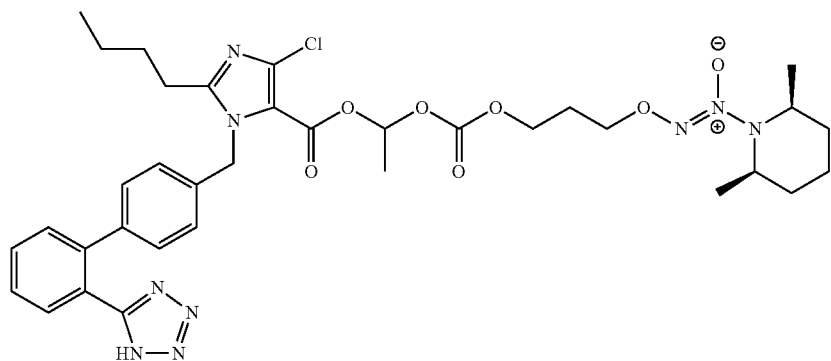

Example 14

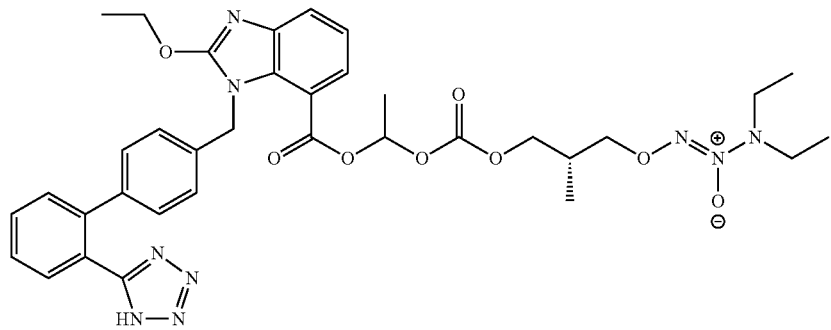

O²-[(2R)-3-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}-2-methylpropyl]1-(N,N-diethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-[(2R)-3-hydroxy-2-methylpropyl] 1-(N,N-diethylamino)diazen-1-ium-1,2-diolate (intermediate 14). $^1$H NMR (500 MHz, CDCl$_3$) δ 0.94 (d, J=7.0 Hz, 3H, D1), 0.95 (d, J=7.0 Hz, 3H, D2), 1.04 (t, J=7.0 Hz, 6H), 1.32-1.37 (m, 3H), 1.43 (t, J=7.0 Hz, 3H), 220-2.29 (m, 1H), 3.07 (q, J=7.0 Hz, 4H), 3.96-4.18 (m, 4H), 4.18-4.28 (m, 1H), 4.42-4.50 (m, 1H), 5.57 (d, J=17.0 Hz, 1H), 5.63 (d, J=17.0 Hz, 1H), 6.68 (q, J=5.0 Hz, 1H), 6.77 (d, J=8.0 Hz, 2H), 6.87 (d, J=8.0 Hz, 2H), 6.96 (t, J=8.0 Hz, 1H), 6.98-7.06 (m, 1H), 7.28-7.33 (m, 1H), 7.49 (d, J=7.5 Hz, 1H), 7.53-7.59 (m, 2H), 7.93-7.97 (m, 1H); LC-MS (M+H) found 716.3.

O²-(4-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}butyl) 1-(N,N-diethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(4-hydroxybutyl) 1-(N,N-diethylamino)diazen-1-ium-1,2-diolate (intermediate 15). $^1$H NMR (500 MHz, CDCl$_3$) δ 1.06 (t, J=7.0 Hz, 6H), 1.40-1.45 (m, 3H), 1.45 (t, J=7.0 Hz, 3H), 1.61-1.68 (m, 214), 1.69-1.76 (m, 2H), 3.08 (q, J=7.0 Hz, 4H), 4.03-4.11 (m, 2H), 4.20 (t, J=6.5 Hz, 2H), 4.31-4.41 (m, 1H), 4.47-4.56 (m, 1H), 5.58 (d, J=16.5 Hz, 1H), 5.67 (d, J=16.5 Hz, 1H), 6.73 (q, J=6.0 Hz, 1H), 6.92 (d, J=8.0 Hz, 2H), 6.92 (d, J=8.0 Hz, 2H), 7.02 (t, J=8.0 Hz, 1H), 7.18-7.27 (m, 1H), 7.30-7.35 (m, 1H), 7.50-7.58 (m, 3H), 7.95-8.00 (m, 1H); LC-MS (M+H) found 716.0. Chromatography of the racemic mixture over Chiralpak AD column, eluting with isopropanol/carbon dioxide, afforded the separate enantiomers.

Example 15

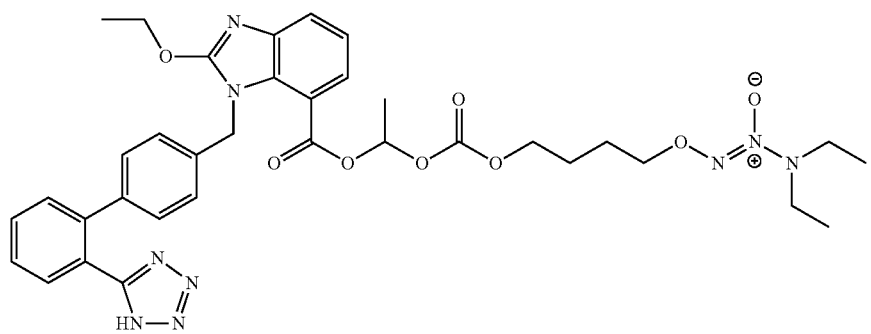

Example 16

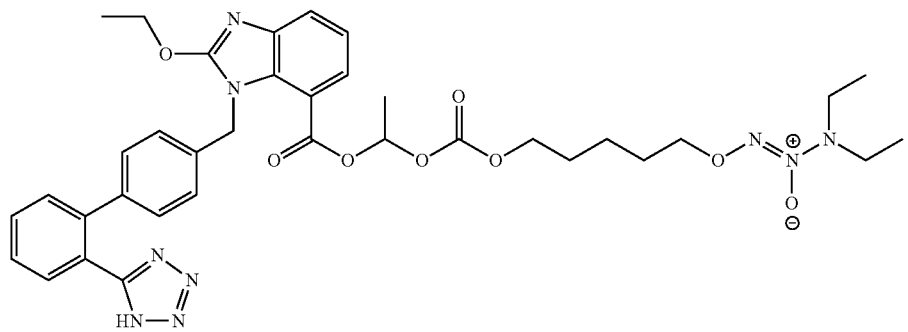

O$^2$-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}pentyl) 1-(N,N-diethylamino)diazen-1-ium-1,2-diolate The title compound was prepared by following the procedure for example 2, except that the reagent O$^2$-(3-hydroxypropyl) 1-(N,N-diethylamino)diazen-1-ium-1,2-diolate (intermediate 6) was replaced by O$^2$-(5-hydroxypentyl) 1-(N,N-diethylamino)diazen-1-ium-1,2-diolate (intermediate 16). $^1$H NMR (500 MHz, CDCl$_3$) δ 1.06 (t, J=7.0 Hz, 6H), 1.32-1.48 (m, 8H), 1.58 (quintet, J=7.0 Hz, 2H), 1.70 (quintet, J=7.0 Hz, 2H), 3.07 (q, J=7.0 Hz, 4H), 3.99-4.09 (m, 2H), 4.19 (t, J=6.5 Hz, 2H), 4.26-4.41 (m, 1H), 4.44-4.55 (m, 1H), 5.60-5.69 (m, 2H), 6.68-6.76 (m, 1H), 6.76-6.86 (m, 2H), 6.86-6.95 (m, 2H), 6.96-7.05 (m, 1H), 7.29-7.35 (m, 1H), 7.48-7.60 (m, 3H), 7.94-8.02 (m, 214); LC-MS (M+H) found 730.3. Chromatography of the racemic mixture over Chiralpak AD column, eluting with isopropanol/carbon dioxide, afforded the separate enantiomers.

Example 17

O$^2$-(5-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}pentyl) 1-(N-tert-butylmethylamino)diazen-1-ium-1,2-diolate The title compound was prepared by following the procedure for example 1, except that the reagent O$^2$-(3-hydroxypropyl) 1-(N,N-diethylamino)diazen-1-ium-1,2-diolate (intermediate 6) was replaced by O$^2$-(5-hydroxypentyl) 1-(N-tert-butylmethylamino)diazen-1-ium-1,2-diolate (intermediate 17). $^1$H NMR (500 MHz, CDCl$_3$) δ 0.88 (t, J=7.0 Hz, 3H), 1.20 (s, 9H), 1.29-1.40 (m, 4H), 1.57 (d, J=5.5 Hz, 3H), 1.53-1.71 (m, 6H), 2.58-2.66 (m, 2H), 2.78 (s, 3H), 4.00-4.10 (m, 2H), 4.14 (t, J=7.0 Hz, 2H), 5.42 (d, J=16.5 Hz, 1H), 5.54 (d, J=16.5 Hz, 1H), 6.84 (q, J=5.5 Hz, 1H), 6.93 (d, J=8.0 Hz, 2H), 7.11 (d, J=8.0 Hz, 2H), 7.42 (d, J=7.0 Hz, 1H), 7.50 (t, J=7.0 Hz, 1H), 7.58 (d, J=7.0 Hz, 1H), 7.86-7.92 (m, 1H); LC-MS (M+H) found 740.2.

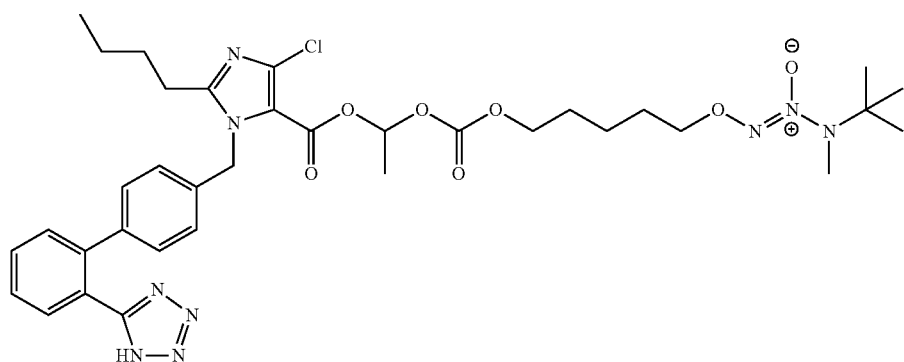

Example 18

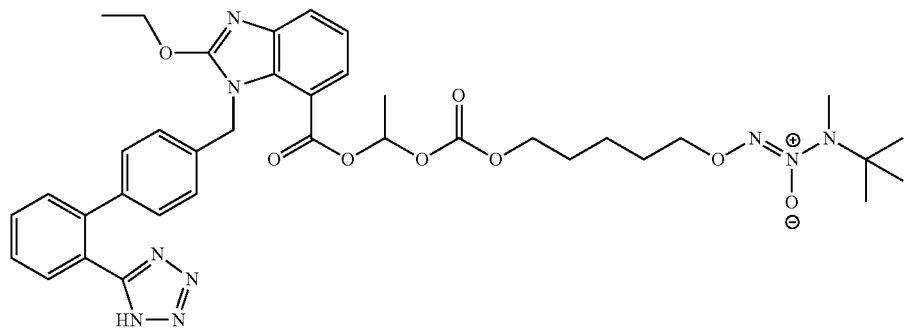

O²-(5-{[(1-{[(2-ethoxy-1-{[2'-(1H-tetrazol-5-yl) biphenyl-4-yl]methyl}-1H-benzimidazol-7-yl)carbonyl]oxy}ethoxy)carbonyl]oxy}pentyl) 1-(N-tert-butylmethylamino)diazen-1-ium-1,2-diolate The title compound was prepared by following the procedure for example 17, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. $^1$H NMR (500 MHz, CDCl$_3$) δ 1.24 (s, 9H), 1.36 (d, J=5.5 Hz, 3H), 1.34-1.43 (m, 2H), 1.45 (t, J=7.0 Hz, 3H), 1.61 (quintet, J=7.0 Hz, 2H), 1.73 (quintet, J=7.0 Hz, 2H), 2.82 (s, 3H), 4.01-4.12 (m, 2H), 4.21 (t, J=7.0 Hz, 2H), 4.20-4.30 (m, 1H), 4.43-4.50 (m, 1H), 5.61 (d, J=17.0 Hz, 1H), 5.65 (d, J=17.0 Hz, 1H), 6.70 (q, J=5.5 Hz, 1H), 6.77 (d, J=8.0 Hz, 2H), 6.88 (d, J=8.0 Hz, 2H), 6.94-7.02 (m, 2H), 7.30-7.35 (m, 1H), 7.48-7.53 (m, 1H), 7.56-7.63 (m, 2H), 7.97-8.02 (m, 1H); LC-MS (M+H) found 744.0. Chromatography of the racemic mixture over Chiralpak AD-H column, eluting with ethanol/carbon dioxide, afforded the separate enantiomers.

Example 19

O²-[5-({[1-({[4-(2-hydroxypropan-2-yl)-2-propyl-1-{[2'-(1H-tetrazol-5-yl)biphenyl-4-yl]methyl}-1H-imidazol-5-yl]carbonyl}oxy)ethoxy]carbonyl}oxy)pentyl] 1-(N-tert-butylmethylamino)diazen-1-ium-1,2-diolate The title compound was prepared by following the procedure for example 17, except that the reagent 2-butyl-4-chloro-1-{[2'-(1-trityl-1H-tetrazol-5-yl)biphenyl-4-yl]methyl}-1H-imidazole-5-carboxylic acid was replaced by 4-(2-hydroxypropan-2-yl)-2-propyl-1-{[2'-(1-trityl-1H-tetrazol-5-yl)biphenyl-4-yl]methyl}-1H-imidazole-5-carboxylic acid. $^1$H NMR (500 MHz, CDCl$_3$) δ 0.90 (t, J=7.0 Hz, 3H), 1.19 (s, 9H), 1.28-1.36 (m, 2H), 1.37 (d, J=5.5 Hz, 3H), 1.51 (d, J=5.5 Hz, 6H), 1.52-1.58 (m, 2H), 1.61-1.70 (m, 4H), 2.50 (t, J=8.0 Hz, 2H), 2.76 (s, 3H), 3.92-4.05 (m, 2H), 4.12-4.18 (m, 2H), 5.37 (s, 2H), 6.80 (q, J=5.5 Hz, 1H), 6.78 (d, J=8.0 Hz, 2H), 7.05 (d, J=8.0 Hz, 2H), 7.41 (d, J=7.5 Hz, 1H), 7.47 (t, J=7.5 Hz, 1H), 7.56 (t, J=7.5 Hz, 1H), 7.77 (d, J=7.5 Hz, 1H); LC-MS (M+H) found 750.4.

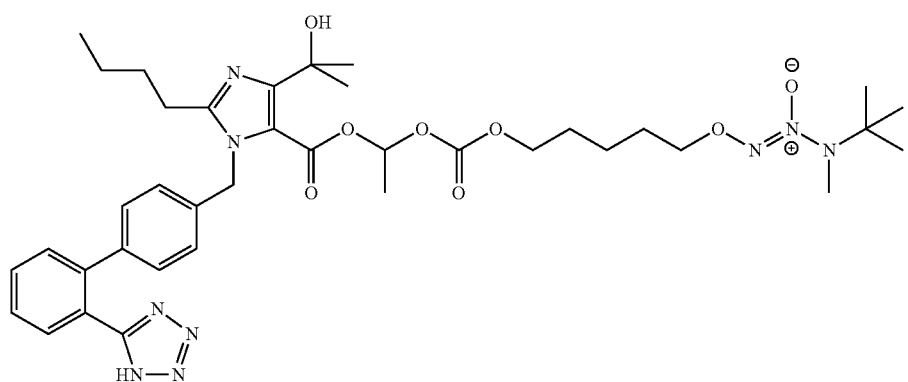

Example 20

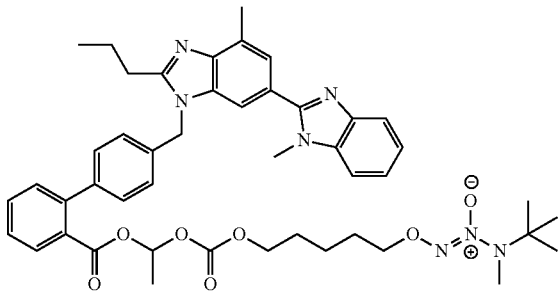

O²-{5-[({1-[({4'-[(1,7'-dimethyl-2'-propyl-1H,3'H-2,
5'-bibenzimidazol-3'-yl)methyl]biphenyl-2-
yl}carbonyl)oxy]ethoxy}carbonyl)oxy]pentyl} 1-(N-
tert-butylmethylamino)diazen-1-ium-1,2-diolate The title compound was prepared by following the procedure for example 17, except that the reagent 2-butyl-4-chloro-1-{[2'-(1-trityl-1H-tetrazol-5-yl)biphenyl-4-yl]methyl}-1H-imidazole-5-carboxylic acid was replaced by 4'-[(1,7'-dimethyl-2'-propyl-1H,3'H-2,5'-bibenzimidazol-3'-yl)methyl]biphenyl-2-carboxylic acid. ¹H NMR (500 MHz, CDCl₃) δ 1.02 (t, J=7.0 Hz, 3H), 1.17 (s, 9H), 1.18-1.22 (m, 3H), 1.40 (quintet, J=7.5 Hz, 2H), 1.62 (quintet, J=7.5 Hz, 2H), 1.72 (quintet, J=8.0 Hz, 2H), 1.85 (sextet, J=8.0 Hz, 2H), 2.72 (s, 3H), 2.75 (s, 3H), 2.90 (t, J=8.0 Hz, 2H), 3.75 (s, 3H), 3.99-4.10 (m, 2H), 4.18 (t, J=7.0 Hz, 2H), 5.41 (s, 2H), 6.67 (q, J=5.5 Hz, 1H), 7.05 (d, J=8.0 Hz, 2H), 7.20 (d, J=8.0 Hz, 2H), 7.21-7.28 (m, 3H), 7.29-7.38 (m, 2H), 7.40 (s, 1H), 7.44-7.50 (m, 2H), 7.75-7.79 (m, 1H), 7.82 (d, J=8.0 Hz, 1H); LC-MS (M+H) found 818.5. Chromatography of the racemic mixture over Chiralcel OD column, eluting with methanol/carbon dioxide, afforded the separate enantiomers.

Example 21

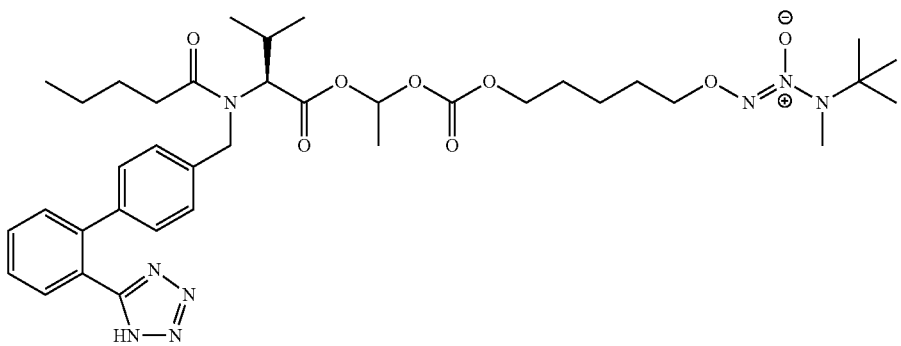

O²-{5-[({1-[(N-pentanoyl-N-{[2'-(1H-tetrazol-5-yl)
biphenyl-4-yl]methyl}-L-valyl)oxy]
ethoxy}carbonyl)oxy]pentyl} 1-(N-tert-butylmethy-
lamino)diazen-1-ium-1,2-diolate The title compound was prepared by following the procedure for example 17, except that the reagent 2-butyl-4-chloro-1-{[2'-(1-trityl-1H-tetrazol-5-yl)biphenyl-4-yl]methyl}-1H-imidazole-5-carboxylic acid was replaced by N-pentanoyl-N-{[2'-(1-trityl-1H-tetrazol-5-yl)biphenyl-4-yl]methyl}-L-valine. ¹H NMR (500 MHz, CDCl₃) δ 0.81-1.03 (m, 8H), 1.09 (t, J=7.0 Hz, 3H), 1.21 (s, 9H), 1.34-1.40 (m, 5H), 1.56-1.78 (m, 6H), 2.26-2.36 (m, 2H), 2.78 (s, 3H), 2.88-3.00 (m, 1H), 3.96-4.13 (m, 2H), 4.15-4.22 (m, 2H), 4.53 (d, J=18.0 Hz, 1H), 4.68 (d, J=18.0 Hz, 1H), 4.71-4.84 (m, 1H), 6.57-6.63 (m, 1H), 6.99-7.14 (m, 4H), 7.35 (d, J=7.5 Hz, 1H), 7.39-7.51 (m, 2H), 7.54 (t, J=7.5 Hz, 1H); LC-MS (M+H) found 739.4. Chromatography of the diastereomeric mixture over Chiralcel OD column, eluting with methanol/carbon dioxide, afforded the separate diastereomers.

Example 22

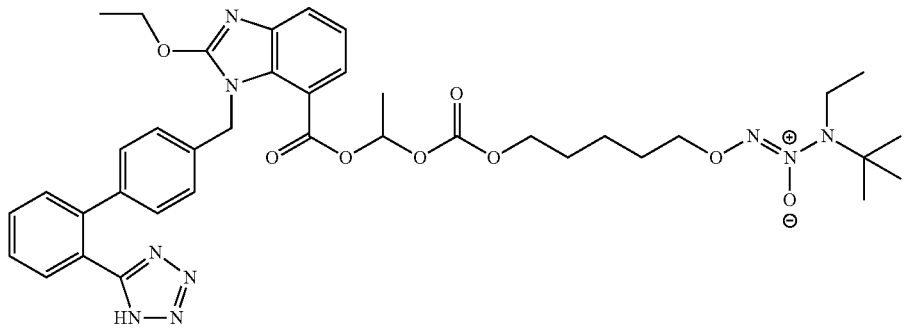

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}pentyl) 1-(N-tert-butylethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(5-hydroxypentyl) 1-(N-tert-butylethylamino)diazen-1-ium-1,2-diolate (intermediate 18). ¹H NMR (500 MHz, CDCl₃) δ 1.01 (t, J=7.0 Hz, 3H), 1.21 (s, 9H), 1.30-1.38 (m, 2H), 1.41-1.48 (m, 6H), 1.56 (quintet, J=7.0 Hz, 2H), 1.68 (quintet, J=7.0 Hz, 2H), 3.09 (q, J=7.0 Hz, 2H), 3.97-4.08 (m, 2H), 4.19 (t, J=7.0 Hz, 2H), 4.34-4.44 (m, 1H), 4.49-4.57 (m, 1H), 5.59 (d, J=16.5 Hz, 1H), 5.68 (d, J=16.5 Hz, 1H), 6.74 (q, J=5.5 Hz, 1), 6.84 (d, J=8.0 Hz, 2H), 6.94 (d, J=8.0 Hz, 2H), 7.05 (t, J=8.0 Hz, 1H), 7.25-7.32 (m, 1H), 7.32-7.36 (m, 1H), 7.52-7.60 (m, 3H), 7.97-8.02 (m, 1H); LC-MS (M+H) found 758.6.

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}pentyl) 1-(2-methylpiperidin-1-yl)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(5-hydroxypentyl) 1-(2-methylpiperidin-1-yl)diazen-1-ium-1,2-diolate (intermediate 19). ¹H NMR (500 MHz, CDCl₃) δ 0.98 (d, J=6.0 Hz, 3H), 1.17-1.50 (m, 10H), 1.53-1.62 (m, 2H), 1.64-1.84 (m, 6H), 3.10-3.23 (m, 3H), 3.96-4.11 (m, 2H), 4.12-4.30 (m, 3H), 4.38-4.51 (m, 1H), 5.54-5.66 (m, 2H), 6.64-6.71 (m, 1H), 6.75 (d, J=7.5 Hz, 2H), 6.85 (d, J=7.5 Hz, 2H), 6.91-7.06 (m, 2H), 7.25-7.34 (m, 1H), 7.48 (d, J=8.0 Hz, 1H), 7.50-7.62 (m, 2H), 7.93-8.01 (m, 1H); LC-MS (M+H) found 756.2.

Example 23

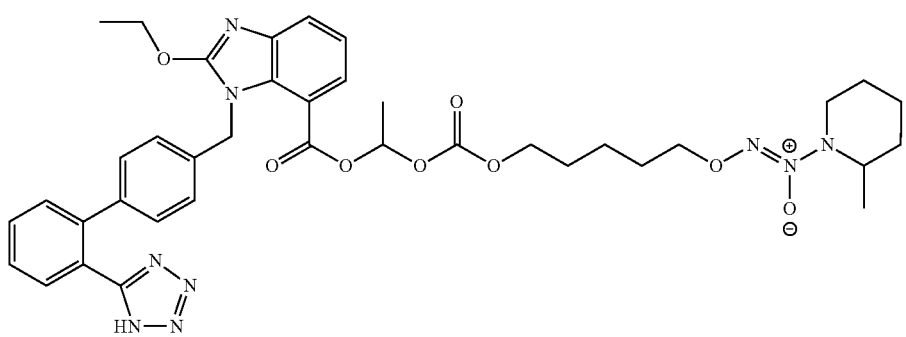

Example 24

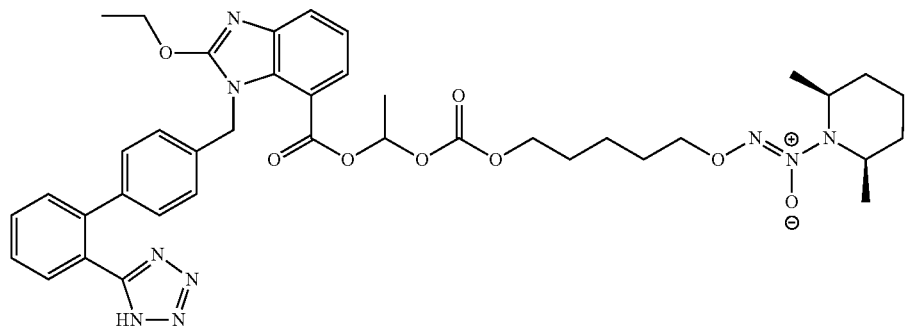

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}pentyl) 1-(cis-2,6-dimethylpiperidin-1-yl)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(5-hydroxypentyl) 1-(cis-2,6-dimethylpiperidin-1-yl)diazen-1-ium-1,2-diolate (intermediate 20). ¹H NMR (500 MHz, CDCl₃) δ 0.88 (t, J=7.0 Hz, 3H), 0.99 (d, J=5.5 Hz, 6H), 1.21-1.32 (m, 2H), 1.32-1.39 (m, 2H), 1.39-1.48 (m, 5H), 1.53-1.61 (m, 2H), 1.63-1.73 (m, 2H), 1.73-1.80 (m, 2H), 3.10-3.19 (m, 2H), 3.96-4.08 (m, 2H), 4.21 (t, J=7.0 Hz, 2H), 4.21-4.30 (m, 1H), 4.38-4.50 (m, 1H), 5.59 (d, J=16.5 Hz, 1H), 5.64 (d, J=16.5 Hz, 1H), 6.65-6.72 (m, 1H), 6.72-6.81 (m, 2H), 6.83-6.90 (m, 2H), 6.93-7.00 (m, 2H), 7.00-7.10 (m, 1H), 7.28-7.33 (m, 2H), 7.53-7.60 (m, 2H), 7.67 (d, J=7.5 Hz, 1H); LC-MS (M+H) found 770.4.

Example 25

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}pentyl) 1-[4-(ethoxycarbonyl)piperazin-1-yl]diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(5-hydroxypentyl) 1-[4-(ethoxycarbonyl)piperazin-1-yl]diazen-1-ium-1,2-diolate (intermediate 21). ¹H NMR (500 MHz, CDCl₃) δ 1.26 (t, J=7.0 Hz, 3H), 1.32-1.40 (m, 2H), 1.42-1.50 (m, 6H), 1.58 (quintet, J=7.0 Hz, 2H), 1.69 (quintet, J=7.0 Hz, 2H), 3.36 (t, J=5.0 Hz, 4H), 3.64 (t, J=5.0 Hz, 4H), 3.99-4.10 (m, 2H), 4.11-4.17 (m, 4H), 4.37-4.47 (m, 1H), 4.49-4.58 (m, 1H), 5.59 (d, J=17.0 Hz, 1H), 5.68 (d, J=17.0 Hz, 1H), 6.76 (q, J=5.0 Hz, 1H), 6.86 (d, J=6.5 Hz, 2H), 6.96 (d, J=6.5 Hz, 2H), 7.06 (t, J=7.0 Hz, 1H), 7.35 (d, J=7.0 Hz, 2H), 7.52-7.59 (m, 3H), 7.97-8.02 (m, 1H); LC-MS (M+H) found 815.8.

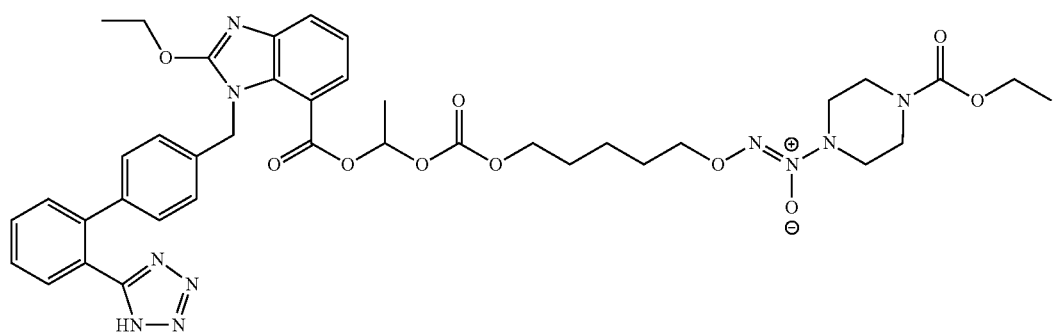

Example 26

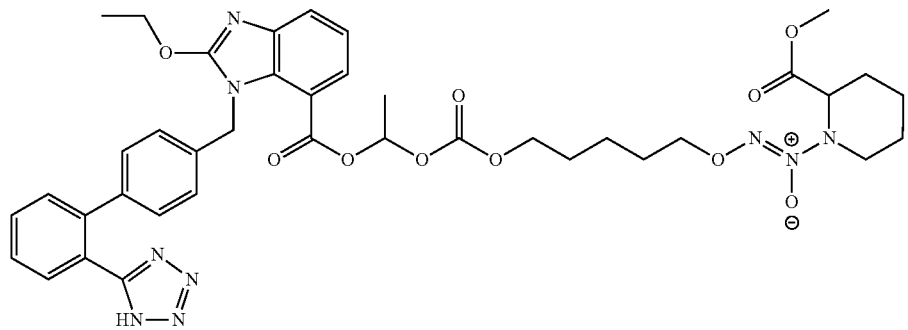

$O^2$-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}pentyl) 1-[2-(methoxycarbonyl)piperidin-1-yl]diazen-1-ium-1,2-diolate The title compound was prepared by following the procedure for example 2, except that the reagent $O^2$-(3-hydroxypropyl) 1-(N,N-diethylamino)diazen-1-ium-1,2-diolate (intermediate 6) was replaced by $O^2$-(5-hydroxypentyl) 1-[2-(methoxycarbonyl)piperidin-1-yl]diazen-1-ium-1,2-diolate (intermediate 22). $^1$H NMR (500 MHz, CDCl$_3$) δ 1.28-1.36 (m, 21), 1.48 (t, J=7.1 Hz, 3H), 1.53 (d, J=5.3 Hz, 3H), 1.50-1.60 (m, 4H), 1.61-1.68 (m, 2H), 1.69-1.77 (m, 1H), 1.80-1.87 (m, 1H), 1.96-2.07 (m, 2H), 3.57 (t, J=6.6 Hz, 2H), 3.69 (s, 3H, D1), 3.69 (s, 3H, D2), 3.98-4.08 (m, 2H), 4.08-4.15 (m, 2H), 4.46-4.56 (m, 2H), 4.56-4.63 (m, 1H), 5.60 (d, J=16.5 Hz, 1H), 5.73 (d, J=16.5 Hz, 1H), 6.79 (q, J=5.5 Hz, 1H), 6.90 (d, J=7.8 Hz, 2H), 7.00 (d, J=8.3 Hz, 2H), 7.11 (t, J=7.8 Hz, 1H), 7.37 (dd, J=1.4, 7.6 Hz, 1H), 7.47-7.60 (m, 4H), 8.00 (d, J=7.4 Hz, 1H); LC-MS (M+H) found 800.6.

$O^2$-(6-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}hexyl) 1-(N,N-diethylamino)diazen-1-ium-1,2-diolate The title compound was prepared by following the procedure for example 2, except that the reagent $O^2$-(3-hydroxypropyl) 1-(N,N-diethylamino)diazen-1-ium-1,2-diolate (intermediate 6) was replaced by $O^2$-(6-hydroxyhexyl) 1-(N,N-diethylamino)diazen-1-ium-1,2-diolate (intermediate 23). $^1$H NMR (500 MHz, CDCl$_3$) δ 1.06 (t, J=7.0 Hz, 6H), 1.22-1.37 (m, 7H), 1.42 (t, J=7.0 Hz, 3H), 1.50-1.58 (m, 2H), 1.65-1.73 (m, 2H), 3.06 (q, J=7.0 Hz, 4H), 3.96-4.08 (m, 2H), 4.17-4.27 (m, 1H), 4.21 (t, J=6.5 Hz, 2H), 4.37-4.47 (m, 1H), 5.55-5.66 (m, 2H), 6.67 (q, J=4.5 Hz, 1H), 6.74 (d, J=6.5 Hz, 2H), 6.85 (d, J=6.5 Hz, 2H), 6.90-7.02 (m, 2H), 7.27-7.33 (m, 1H), 7.48 (d, J=7.0 Hz, 1H), 7.53-7.62 (m, 2H), 7.95-8.02 (m, 1H); LC-MS (M+H) found 744.5.

Example 27

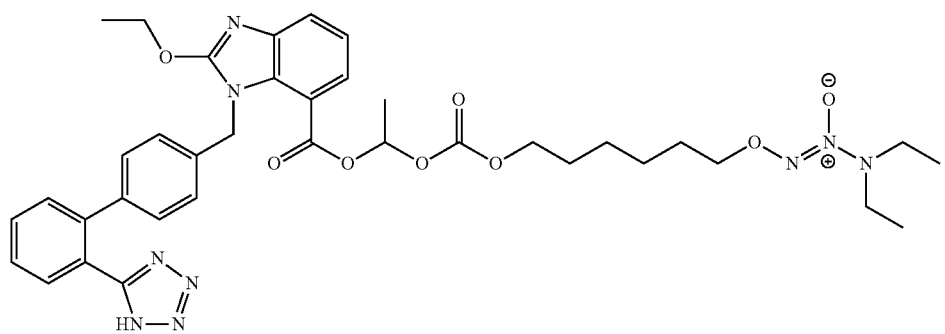

Example 28

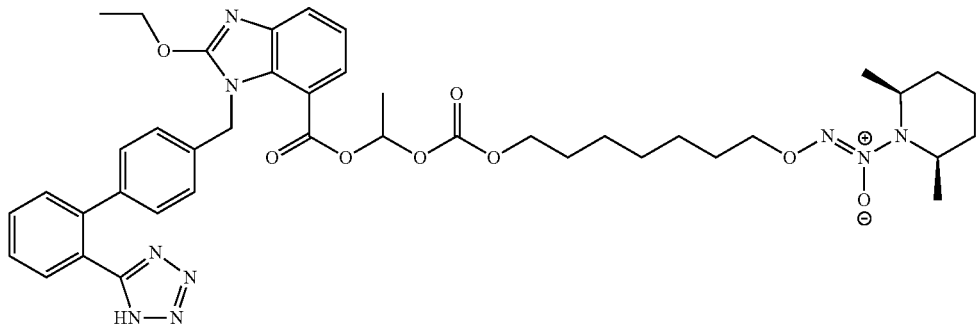

O²-(7-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}heptyl) 1-(cis-2,6-dimethylpiperidin-1-yl)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(7-hydroxyheptyl) 1-(cis-2,6-dimethylpiperidin-1-yl)diazen-1-ium-1,2-diolate (intermediate 24). ¹H NMR (500 MHz, CDCl₃) δ 0.99 (d, J=6.0 Hz, 6H), 1.21-1.27 (m, 4H), 1.27-1.35 (m, 4H), 1.36-1.44 (m, 6H), 1.47-1.56 (m, 4H), 1.64-1.80 (m, 4H), 3.10-3.19 (m, 2H), 3.95-4.07 (m, 2H), 4.14-4.22 (m, 1H), 4.23 (t, J=7.0 Hz, 2H), 4.38-4.46 (m, 1H), 5.60 (s, 2H), 6.66 (q, J=5.5 Hz, 1H), 6.72 (d, J=7.5 Hz, 2H), 6.84 (d, J=7.5 Hz, 2H), 6.88-6.98 (m, 2H), 7.29 (d, J=6.5 Hz, 1H), 7.47 (d, J=6.5 Hz, 1H), 7.53-7.60 (m, 2H), 7.97 (d, J=6.5 Hz, 1H); LC-MS (M+H) found 798.7.

O²-(6-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}hexan-2-yl) 1-(N-tert-butylmethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(6-hydroxyhexan-2-yl) 1-(N-tert-butylmethylamino)diazen-1-ium-1,2-diolate (intermediate 25). ¹H NMR (500 MHz, CDCl₃) δ 1.20 (s, 9H), 1.29 (t, J=7.1 Hz, 3H), 1.30-1.44 (m, 2H), 1.47 (t, J=7.1 Hz, 3H), 1.50 (d, J=5.2 Hz, 3H), 1.52-1.62 (m, 3H), 1.64-1.78 (m, 1H), 2.78 (s, 3H), 3.98-4.08 (m, 2H), 4.34 (sextet, J=6.4 Hz, 1H), 4.40-4.52 (m, 1H), 4.57 (t, J=6.9 Hz, 1H), 5.59 (d, J=16.7 Hz, 1H), 5.70 (d, J=16.9 Hz, 1H, D1), 5.70 (d, J=16.9 Hz, 1H, D2), 6.77 (q, J=5.5 Hz, 1H, D1), 6.77 (q, J=5.5 Hz, 1H, D2), 6.89 (d, J=6.9 Hz, 2H), 6.98 (d, J=6.9 Hz, 2H), 7.08 (t, J=8.0 Hz, 1H), 7.36 (d, J=7.4 Hz, 1H), 7.38-7.46 (m, 1H), 7.51-7.59 (m, 3H), 8.00 (t, J=7.4 Hz, 1H); LC-MS (M+H) found 758.7.

Example 29

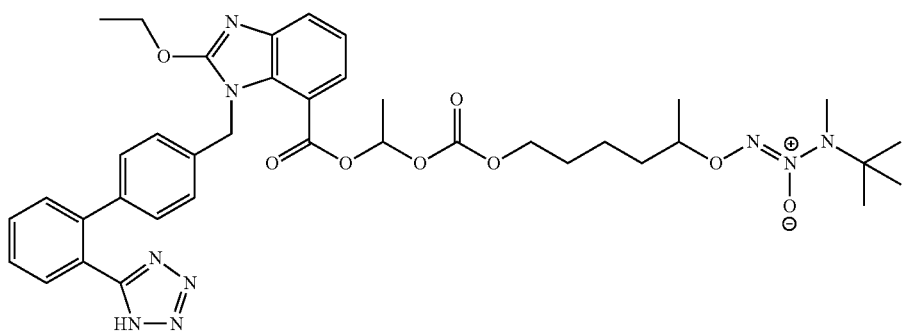

Example 30

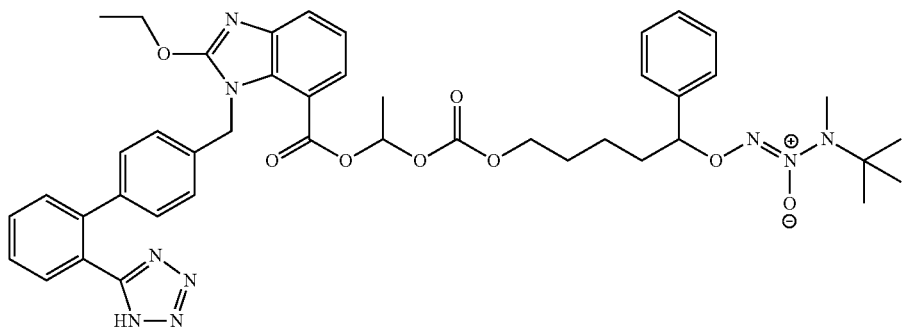

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}-1-phenylpentyl) 1-(N-tert-butylmethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(5-hydroxy-1-phenylpentyl) 1-(N-tert-butylmethylamino)diazen-1-ium-1,2-diolate (intermediate 26). $^1$H NMR (500 MHz, CDCl$_3$) δ 1.06 (s, 9H, D1), 1.06 (s, 9H, D2), 1.22-1.36 (m, 1H), 1.42 (d, J=5.5 Hz, 3H), 1.45 (t, J=6.7 Hz, 3H), 1.51-1.62 (m, 3H), 1.74-1.86 (m, 1H), 1.97-2.16 (m, 1H), 2.72 (s, 3H), 3.95-4.07 (m, 2H), 4.30-4.44 (m, 1H), 4.48-4.58 (m, 1H), 5.12-5.17 (m, 1H), 5.66 (d, J=16.5 Hz, 1H, D1), 5.66 (d, J=16.5 Hz, 1H, D2), 5.80 (d, J=16.5 Hz, 1H), 6.72 (q, J=5.2 Hz, 1H), 6.80-6.85 (m, 2H), 6.92 (d, J=7.5 Hz, 2H), 7.03 (t, J=7.8 Hz, 1H), 7.22-7.36 (m, 7H), 7.51-7.60 (m, 3H), 7.98 (dt, J=2.5, 6.2 Hz, 1H); LC-MS (M+H) found 820.8.

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}-2-methylpentyl) 1-(N-tert-butylmethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(5-hydroxy-2-methylpentyl) 1-(N-tert-butylmethylamino)diazen-1-ium-1,2-diolate (intermediate 27). $^1$H NMR (500 MHz, CDCl$_3$) δ 0.88 (d, J=6.7 Hz, 3H, D1), 0.89 (d, J=6.7 Hz, 3H, D2), 1.20 (s, 9H), 1.36-1.48 (m, 1H), 1.46 (d, J=5.5 Hz, 3H), 1.45 (t, J=7.1 Hz, 3H), 1.48-1.70 (m, 3H), 1.82-1.94 (m, 1H), 2.78 (s, 3H), 3.96-4.10 (m, 2H), 4.36-4.48 (m, 2H), 4.50-4.58 (m, 2H), 5.59 (d, J=16.7 Hz, 1H), 5.68 (d, J=16.7 Hz, 1H), 6.75 (q, J=5.5 Hz, 1H, D1), 6.75 (q, J=5.5 Hz, 1H, D2), 6.86 (d, J=7.8 Hz, 2H), 6.96 (d, J=7.8 Hz, 2H), 7.05 (t, J=7.8 Hz, 1H), 7.28-7.33 (m, 1H), 7.34 (d, J=7.4 Hz, 1H), 7.52-7.69 (m, 3H), 8.00 (d, J=7.8 Hz, 1H); LC-MS (M+H) found 758.5.

Example 31

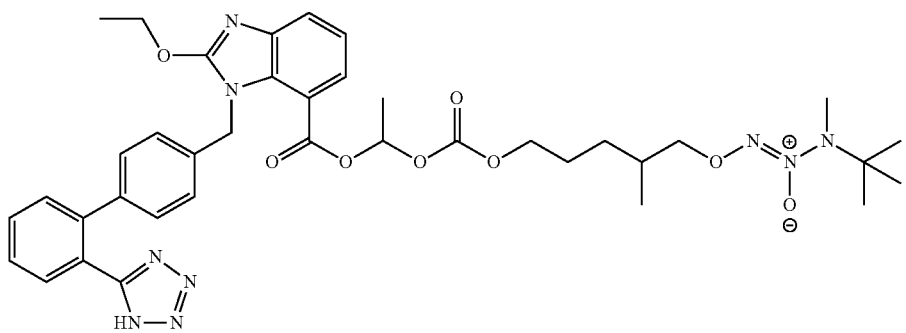

Example 32

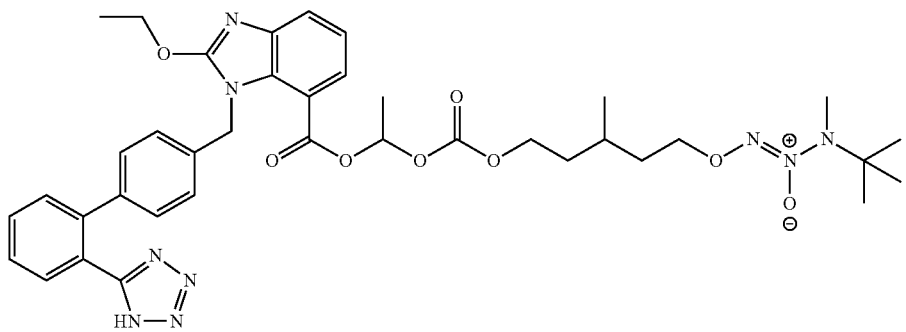

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}-3-methylpentyl) 1-(N-tert-butylmethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(5-hydroxy-3-methylpentyl) 1-(N-tert-butylmethylamino)diazen-1-ium-1,2-diolate (intermediate 28). Chromatography of the racemic mixture over Chiralpak AD-H column, eluting with methanol/carbon dioxide, afforded the four separate stereoisomers, two of which are enantiomeric to each other.

Diastereomer A: ¹H NMR (500 MHz, CD₃CN) δ 0.88 (d, J=6.3 Hz, 3H), 1.12 (s, 9H), 1.41 (t, J=7.1 Hz, 3H), 1.43 (d, J=5.4 Hz, 3H), 1.44-1.50 (m, 2H), 1.60-1.71 (m, 3H), 2.68 (s, 3H), 4.12-4.19 (m, 4H), 4.51 (qd, J=7.1, 10.3 Hz, 1H), 4.56 (qd, J=7.1, 10.3 Hz, 1H), 5.53 (d, J=16.4 Hz, 1H), 5.58 (d, J=16.5 Hz, 1H), 6.80 (q, J=5.4 Hz, 1H), 6.91 (d, J=8.0 Hz, 2H), 6.98 (d, J=8.1 Hz, 2H), 7.13 (t, J=7.9 Hz, 1H), 7.43 (dd, J=1.2, 7.7 Hz, 1H), 7.51-7.55 (m, 3H), 7.61 (dt, J=1.4, 7.6 Hz, 1H), 7.70 (dd, J=1.4, 7.6 Hz, 1H); LC-MS (M+H) found 758.7.

Diastereomer B: ¹H NMR (500 MHz, CD₃CN) δ 0.88 (d, J=6.3 Hz, 3H), 1.13 (s, 9H), 1.40 (t, J=7.1 Hz, 3H), 1.42 (d, J=5.5 Hz, 3H), 1.43-1.50 (m, 2H), 1.58-1.74 (m, 3H), 2.68 (s, 3H), 4.09-4.23 (m, 4H), 4.44-4.60 (m, 2H), 5.52 (d, J=16.4 Hz, 1H), 5.57 (d, J=16.5 Hz, 1H), 6.78 (q, J=5.4 Hz, 1H), 6.90 (d, J=8.0 Hz, 2H), 6.96 (d, J=8.0 Hz, 2H), 7.08-7.16 (m, 1H), 7.42 (d, J=7.8 Hz, 1H), 7.49-7.54 (m, 3H), 7.60 (dt, J=1.4, 7.6 Hz, 1H), 7.70 (d, J=7.7 Hz, 1H); LC-MS (M+H) found 758.7.

Example 33

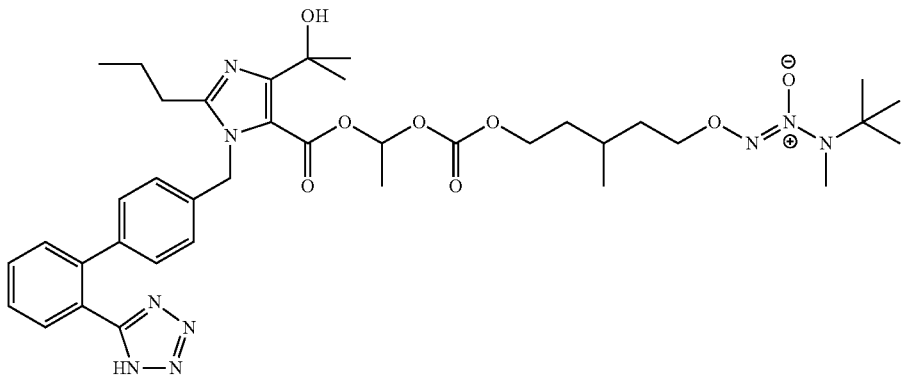

O²-[5-({1-({[4-(2-hydroxypropan-2-yl)-2-propyl-1-{[2'-(1H-tetrazol-5-yl)biphenyl-4-yl]methyl}-1H-imidazol-5-yl]carbonyl}oxy)ethoxy]carbonyl}oxy)-3-methylpentyl] 1-(N-tert-butylmethylamino)diazen-1-ium-1,2-diolate The title compound was prepared by following the procedure for example 32, except that the reagent 2-ethoxy-1-{[2'-(1-trityl-1H-tetrazol-5-yl)biphenyl-4-yl]methyl}-1H-benzimidazole-7-carboxylic acid was replaced by 4-(2-hydroxypropan-2-yl)-2-propyl-1-{[2'-(1-trityl-1H-tetrazol-5-yl)biphenyl-4-yl]methyl}-1H-imidazole-5-carboxylic acid. ¹H NMR (500 MHz, CDCl₃) δ 0.86 (d, J=7.0 Hz, 3H, D1), 0.87 (d, J=7.0 Hz, 3H, D2), 0.97 (t, J=7.0 Hz, 3H), 1.21 (s, 9H), 1.38-1.47 (m, 1H), 1.55 (d, J=5.5 Hz, 3H), 1.47-1.56 (m, 1H), 1.58-1.75 (m, 5H), 1.70 (s, 6H), 2.79 (s, 3H), 3.00 (t, J=7.5 Hz, 2H), 4.12-4.16 (m, 2H), 4.16-4.38 (m, 2H), 5.55 (d, J=16.5 Hz, 1H), 5.59 (d, J=16.5 Hz, 1H), 6.87 (q, J=5.0 Hz, 1H), 6.94 (d, J=8.0 Hz, 2H), 7.12 (d, J=8.0 Hz, 2H), 7.43 (d, J=8.0 Hz, 1H), 7.49 (t, J=7.0 Hz, 1H), 7.59 (t, J=7.0 Hz, 1H), 7.77 (d, J=8.0 Hz, 1H); LC-MS (M+H) found 764.7.

Example 34

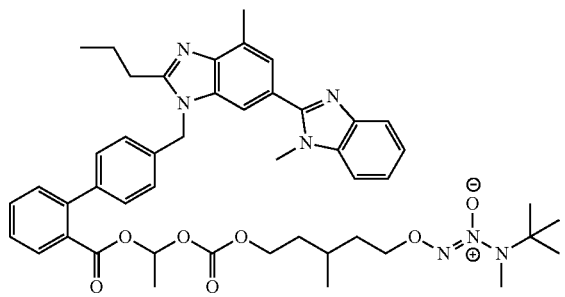

O²-{5-[({1-[({4'-[(1,7'-dimethyl-2'-propyl-1H,3'H-2,5'-bibenzimidazol-3'-yl)methyl]biphenyl-2-yl}carbonyl)oxy]ethoxy}carbonyl)oxy]-3-methylpentyl} 1-(N-tert-butylmethylamino)diazen-1-ium-1,2-diolate The title compound was prepared by following the procedure for example 32, except that the reagent 2-ethoxy-1-{[2'-(1-trityl-1H-tetrazol-5-yl)biphenyl-4-yl]methyl}-1H-benzimidazole-7-carboxylic acid was replaced by 4'-[(1,7'-dimethyl-2'-propyl-1H,3'H-2,5'-bibenzimidazol-3'-yl)methyl]biphenyl-2-carboxylic acid. ¹H NMR (500 MHz, CDCl₃) δ 0.92 (d, J=5.5 Hz, 3H), 1.09 (t, J=7.5 Hz, 3H), 1.20 (s, 9H), 1.31 (d, J=5.5 Hz, 3H), 1.44-1.53 (m, 1H), 1.64-1.75 (m, 2H), 1.75-1.83 (m, 1H), 1.92 (sextet, J=7.5 Hz, 2H), 2.77 (s, 3H), 2.78 (s, 3H), 3.29 (t, J=7.5 Hz, 2H), 4.01 (s, 3H), 4.04-4.19 (m, 2H), 4.21-4.31 (m, 2H), 5.71 (s, 2H), 6.67 (q, J=5.5 Hz, 1H), 7.20 (d, J=8.5 Hz, 2H), 7.23-7.31 (m, 3H), 7.41 (t, J=7.5 Hz, 1H), 7.52 (t, J=7.5 Hz, 1H), 7.54-7.65 (m, 4H), 7.87 (d, J=6.5 Hz, 1H), 7.89-7.94 (m, 1H), 8.22 (s, 1H); LC-MS (M+H) found 832.7.

Example 35

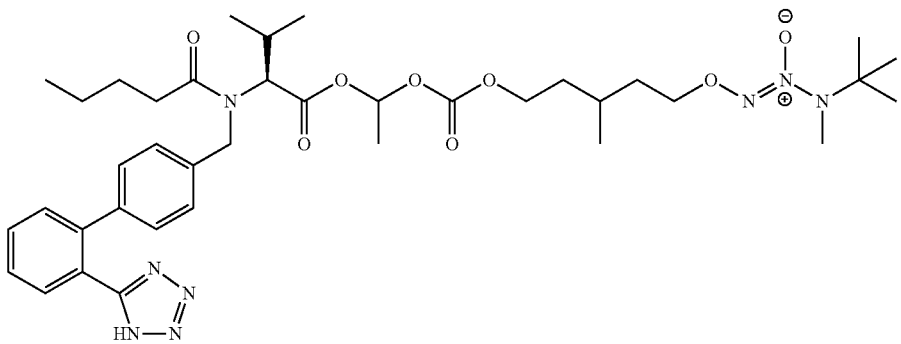

O²-{3-methyl-5-[({1-[(N-pentanoyl-N-{[2'-(1H-tetrazol-5-yl)biphenyl-4-yl]methyl}-L-valyl)oxy]ethoxy}carbonyl)oxy]pentyl} 1-(N-tert-butylmethylamino)diazen-1-ium-1,2-diolate The title compound was prepared by following the procedure for example 32, except that the reagent 2-ethoxy-1-{[2'-(1-trityl-1H-tetrazol-5-yl)biphenyl-4-yl]methyl}-1H-benzimidazole-7-carboxylic acid was replaced by N-pentanoyl-N-{[2'-(1-trityl-1H-tetrazol-5-yl)biphenyl-4-yl]methyl}-L-valine. LC-MS (M+Na) found 775.6.

Example 36

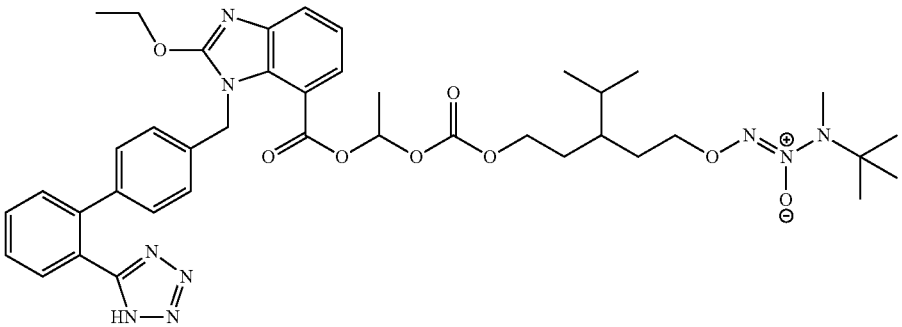

$O^2$-[3-(2-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}ethyl)-4-methylpentyl] 1-(N-tert-butylmethylamino)diazen-1-ium-1,2-diolate The title compound was prepared by following the procedure for example 2, except that the reagent $O^2$-(3-hydroxypropyl) 1-(N,N-diethylamino)diazen-1-ium-1,2-diolate (intermediate 6) was replaced by $O^2$-[3-(2-hydroxyethyl)-4-methylpentyl] 1-(N-tert-butylmethylamino)diazen-1-ium-1,2-diolate (intermediate 29). $^1$H NMR (500 MHz, CDCl$_3$) δ 0.76-0.81 (m, 6H), 1.19 (s, 9H), 1.23-1.27 (m, 1H), 1.30-1.37 (m, 2H), 1.37-1.48 (m, 3H), 1.48-1.57 (m, 1H), 1.57-1.67 (m, 3H), 1.69-1.88 (m, 2H), 2.77 (s, 3H), 3.96-4.13 (m, 21-1), 4.13-4.20 (m, 2H), 4.26-4.43 (m, 1H), 4.46-4.58 (m, 1H), 5.56-5.71 (m, 2H), 6.69-6.77 (m, 1H), 6.78-6.88 (m, 2H), 6.88-6.97 (m, 2H), 6.98-7.07 (m, 1H), 7.30-7.36 (m, 1H), 7.50-7.60 (m, 4H), 7.96-8.01 (m, 1H); LC-MS (M+H) found 786.6.

Example 37

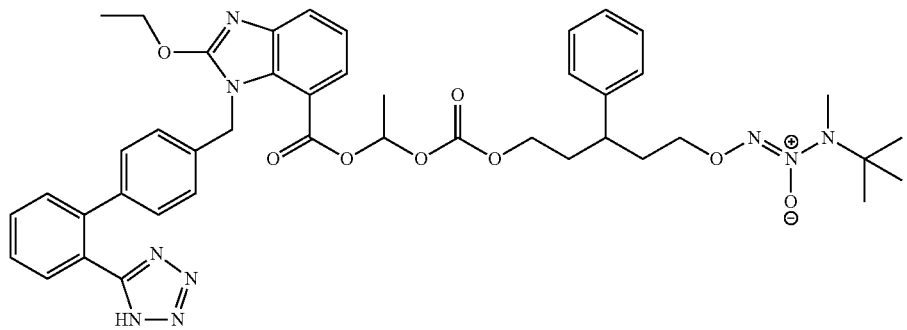

$O^2$-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}-3-phenylpentyl) 1-(N-tert-butylmethylamino)diazen-1-ium-1,2-diolate The title compound was prepared by following the procedure for example 2, except that the reagent $O^2$-(3-hydroxypropyl) 1-(N,N-diethylamino)diazen-1-ium-1,2-diolate (intermediate 6) was replaced by $O^2$-(5-hydroxy-3-phenylpentyl) 1-(N-tert-butylmethylamino)diazen-1-ium-1,2-diolate (intermediate 30). $^1$H NMR (500 MHz, CDCl$_3$) δ 0.87 (t, J=7.0 Hz, 3H), 1.19 (s, 9H), 1.46-1.58 (m, 4H), 1.78-2.18 (m, 4H), 2.76 (s, 3H), 3.79-4.08 (m, 4H), 4.68-4.83 (m, 2H), 5.57-5.76 (m, 2H), 6.72-6.82 (m, 1H), 6.91-7.08 (m, 6H), 7.08-7.39 (m, 6H), 7.42-7.57 (m, 2H), 7.70-7.90 (m, 2H); LC-MS (M+H) found 820.9.

Example 38

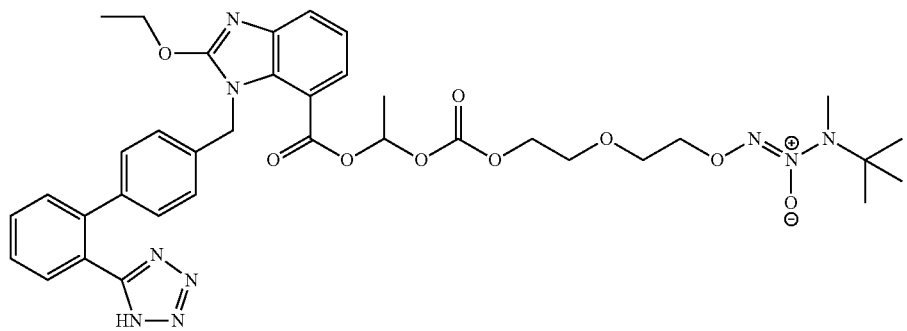

O²-[11-(2-ethoxy-1-{[2'-(1H-tetrazol-5-yl)biphenyl-4-yl]methyl}-1H-benzimidazol-7-yl)-9-methyl-7,11-dioxo-3,6,8,10-tetraoxaundec-1-yl] 1-(N-tert-butylmethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-[2-(2-hydroxyethoxy)ethyl] 1-(N-tert-butylmethylamino)diazen-1-ium-1,2-diolate (intermediate 31). ¹H NMR (500 MHz, CDCl₃) δ 1.19 (s, 9H), 1.44-1.52 (m, 6H), 2.76 (s, 3H), 3.57-3.70 (m, 4H), 4.14-4.28 (m, 4H), 4.42-4.52 (m, 1H), 4.52-4.61 (m, 1H), 5.56 (d, J=16.5 Hz, 1H), 5.68 (d, J=16.5 Hz, 1H), 6.79 (q, J=5.5 Hz, 1H), 6.87 (d, J=8.0 Hz, 2H), 6.99 (d, J=8.0 Hz, 2H), 7.07 (t, J=7.5 Hz, 1H), 7.36 (d, J=6.5 Hz, 1H), 7.38-7.43 (m, 1H), 7.50-7.58 (m, 3H), 7.97 (d, J=7.5 Hz, 1H); LC-MS (M+H) found 746.6.

Example 39

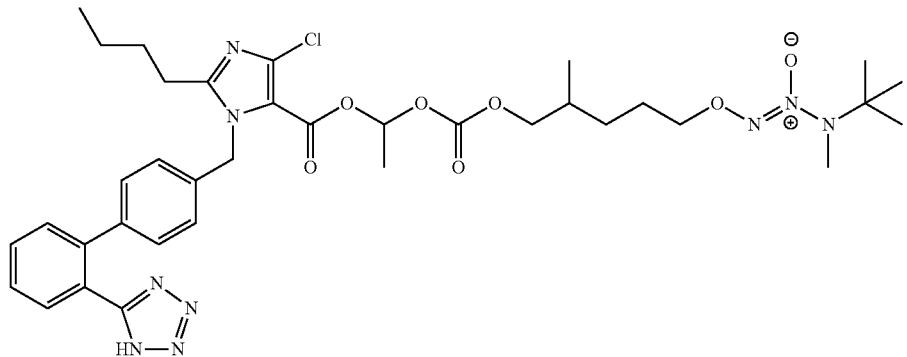

O²-(5-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}-4-methylpentyl) 1-(N-tert-butylmethylamino)diazen-1-ium-1,2-diolate The title compound was prepared by following the procedure for example 1, except that the reagent O²-(3-hydroxypropyl) 1-(N,N-diethylamino)diazen-1-ium-1,2-diolate (intermediate 6) was replaced by O²-(5-hydroxy-4-methylpentyl) 1-(N-tert-butylmethylamino)diazen-1-ium-1,2-diolate (intermediate 32). ¹H NMR (500 MHz, CDCl₃) δ 0.83-0.90 (m, 6H), 1.20 (s, 9H, D1), 1.20 (s, 9H, D2), 1.30-1.44 (m, 4H), 1.59 (d, J=5.5 Hz, 3H), 1.60-1.80 (m, 5H), 2.63 (t, J=6.9, 2H, D1), 2.63 (t, J=6.9, 2H, D2), 2.78 (s, 3H, D1), 2.78 (s, 3H, D2), 3.82-3.96 (m, 2H), 4.13 (t, J=6.9 Hz, 2H), 5.43 (d, J=16.4 Hz, 1H, D1), 5.43 (d, J=16.4 Hz, 1H, D2), 5.57 (d, J=16.5 Hz, 1H, D1), 5.57 (d, J=16.5 Hz, 1H, D2), 6.85 (q, J=5.5 Hz, 1H), 6.94 (d, J=8.5 Hz, 2H, D1), 6.94 (d, J=8.5 Hz, 2H, D2), 7.13 (d, J=8.0 Hz, 2H, D1), 7.13 (d, J=8.0 Hz, 2H, D2), 7.43 (d, J=7.5 Hz, 1H), 7.50 (t, J=7.5 Hz, 1H), 7.58 (dt, J=1.4, 7.5 Hz, 1H), 7.92 (dd, J=1.2, 7.6 Hz, 1H); LC-MS (M+H) found 754.6.

Example 40

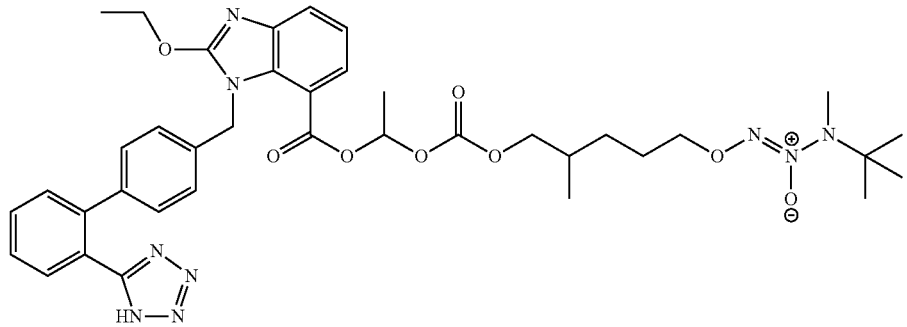

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}-4-methylpentyl) 1-(N-tert-butylmethylamino)diazen-1-ium-1,2-diolate The title compound was prepared by following the procedure for example 39, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. ¹H NMR (500 MHz, CDCl₃) δ 0.84 (d, J=6.1 Hz, 3H, D1), 0.84 (d, J=6.1 Hz, 3H, D2), 1.20 (s, 9H), 1.41 (d, J=5.5 Hz, 3H), 1.44 (t, J=7.3 Hz, 3H), 1.64-1.86 (m, 5H), 2.78 (s, 3H), 3.84-3.94 (m, 2H), 4.13-4.18 (m, 2H), 4.30-4.38 (m, 1H), 4.49-4.55 (m, 1H), 5.59 (d, J=16.7 Hz, 1H), 5.65 (d, J=16.7 Hz, 1H), 6.73 (q, J=5.5 Hz, 1H), 6.83 (d, J=7.8 Hz, 2H), 6.92 (d, J=8.0 Hz, 2H), 7.02 (t, J=7.4 Hz, 1H), 7.18-7.24 (m, 1H), 7.31-7.35 (m, 1H), 7.52-7.58 (m, 3H), 7.97-8.00 (m, 1H); LC-MS (M+H) found 758.5

Example 41

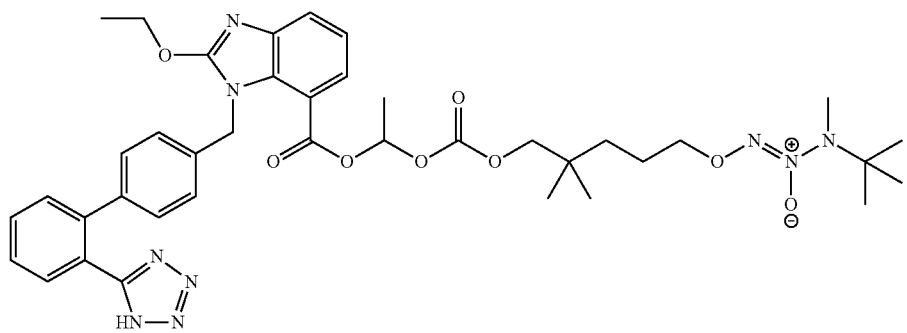

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}-4,4-dimethylpentyl) 1-(N-tert-butylmethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(5-hydroxy-4,4-dimethylpentyl) 1-(N-tert-butylmethylamino)diazen-1-ium-1,2-diolate (intermediate 33). ¹H NMR (500 MHz, CDCl₃) δ 0.82 (s, 6H), 1.20 (s, 9H), 1.23-1.34 (m, 2H), 1.39 (d, J=5.3 Hz, 3H), 1.44 (t, J=7.1 Hz, 3H), 1.61-1.70 (m, 2H), 2.78 (s, 3H), 3.74 (d, J=10.6 Hz, 1H), 3.79 (d, J=10.5 Hz, 1H), 4.14 (t, J=6.9 Hz, 2H), 4.24-4.34 (m, 1H), 4.46-4.54 (m, 1H), 5.59 (d, J=16.2 Hz, 1H), 5.63 (d, J=16.2 Hz, 1H), 6.71 (q, J=5.5 Hz, 1H), 6.81 (d, J=7.7 Hz, 2H), 6.91 (d, J=8.0 Hz, 2H), 6.99 (t, J=7.7 Hz, 1H), 7.10-7.18 (m, 1H), 7.32 (dd, J=3.4, 6.4 Hz, 1H), 7.51 (d, J=8.2 Hz, 1H), 7.56 (dt, J=3.2, 8.9 Hz, 2H), 7.98 (m, 1H); LC-MS (M+H) found 772.5.

Example 42

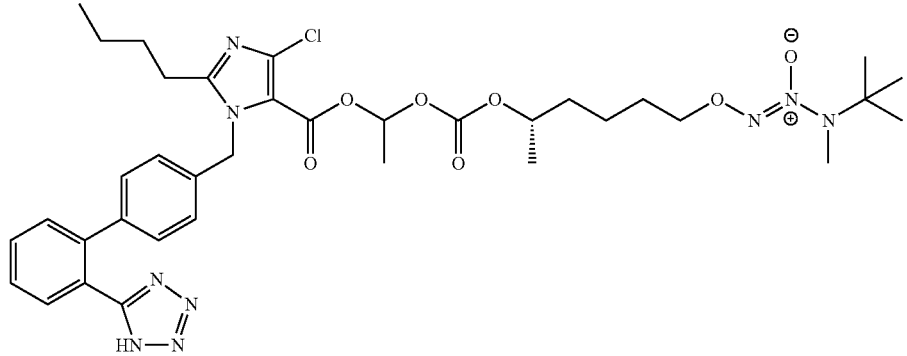

83

O²-[(5S)-5-{[(1-{[(2-butyl-4-chloro-1-{[2'-(1H-tetrazol-5-yl)biphenyl-4-yl]methyl}-1H-imidazol-5-yl)carbonyl]oxy}ethoxy)carbonyl]oxy}hexyl] 1-(N-tert-butylmethylamino)diazen-1-ium-1,2-diolate The title compound was prepared by following the procedure for example 1, except that the reagent O²-(3-hydroxypropyl) 1-(N,N-diethylamino)diazen-1-ium-1,2-diolate (intermediate 6) was replaced by O²-[(5S)-5-hydroxyhexyl] 1-(N-tert-butylmethylamino)diazen-1-ium-1,2-diolate (intermediate 34). ¹H NMR (500 MHz, CDCl₃) δ 0.81 (t, J=7.5 Hz, 3H), 1.17 (s, 9H), 1.23-1.42 (m, 7H), 1.48-1.72 (m, 9H), 2.54 (t, J=8.0 Hz, 2H), 2.74 (s, 3H), 4.09 (t, J=6.5 Hz, 1H), 4.16 (t, J=6.5 Hz, 1H), 4.56-4.75 (m, 1H), 5.36-5.53 (m, 2H), 6.73-6.83 (m, 1H), 6.83-6.94 (m, 2H), 7.02 (d, J=8.0 Hz, 2H), 7.38 (d, J=8.0 Hz, 1H), 7.44 (d, J=8.0 Hz, 1H), 7.54 (t, J=8.0 Hz, 1H), 7.73 (t, J=7.0 Hz, 1H); LC-MS (M+H) found 754.4.

Example 43

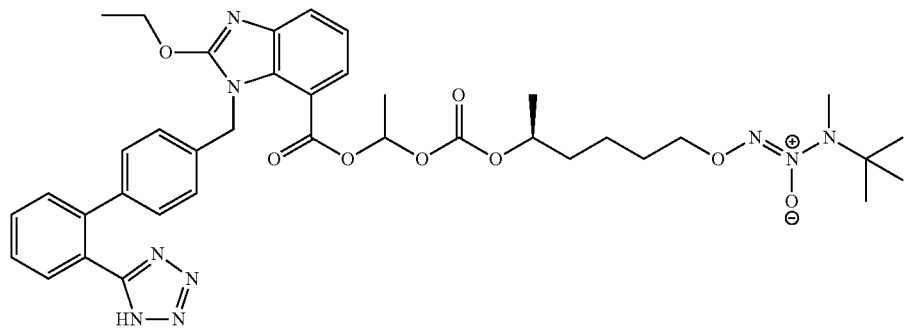

O²-[(5S)-5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}hexyl] 1-(N-tert-butylmethylamino)diazen-1-ium-1,2-diolate The title compound was prepared by following the procedure for example 42, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. Chromatography of the racemic mixture over Chiralpak AD-H column, eluting with isopropanol/carbon dioxide, afforded the two separate stereoisomers.

Diastereomer A: ¹H NMR (500 MHz, CDCl₃) δ 1.18 (d, J=6.7 Hz, 3H), 1.19 (s, 9H), 1.32-1.39 (m, 3H), 1.40-1.51 (m, 4H), 1.54-1.71 (m, 5H), 2.77 (s, 3H), 4.16 (t, J=6.6 Hz, 2H), 4.18-4.24 (m, 1H), 4.52-4.60 (m, 1H), 4.66 (sextet, J=6.2 Hz, 1H), 5.61 (s, 2H), 6.68 (q, J=5.4 Hz, 1H), 6.80 (d, J=7.7 Hz, 2H), 6.89 (d, J=7.9 Hz, 2H), 6.98 (t, J=7.9 Hz, 1H), 7.08 (s, 1H), 7.31 (dd, J=3.4, 6.2 Hz, 1H), 7.49 (d, J=7.8 Hz, 1H), 7.55-7.59 (m, 2H), 7.98 (dd, J=3.3, 5.8 Hz, 1H); LC-MS (M+H) found 758.6.

Diastereomer B: ¹H NMR (500 MHz, CDCl₃) δ 1.20 (d, J=6.7 Hz, 3H), 1.21 (s, 9H), 1.31-1.37 (m, 3H), 1.40-1.51 (m, 4H), 1.54-1.72 (m, 5H), 2.78 (s, 3H), 4.18 (t, J=6.6 Hz, 2H), 4.19-4.24 (m, 1H), 4.52-4.60 (m, 1H), 4.66 (sextet, J=6.2 Hz, 1H), 5.61 (s, 2H), 6.68 (q, J=5.4 Hz, 1H), 6.79 (d, J=7.8 Hz, 2H), 6.90 (d, J=7.9 Hz, 2H), 6.98 (t, J=7.9 Hz, 1H), 7.11 (s, 1H), 7.31 (dd, J=3.3, 6.2 Hz, 1H), 7.49 (d, J=7.8 Hz, 1H), 7.52-7.62 (m, 2H), 7.99 (dd, J=3.4, 5.8 Hz, 1H); LC-MS (M+H) found 758.6.

Example 44

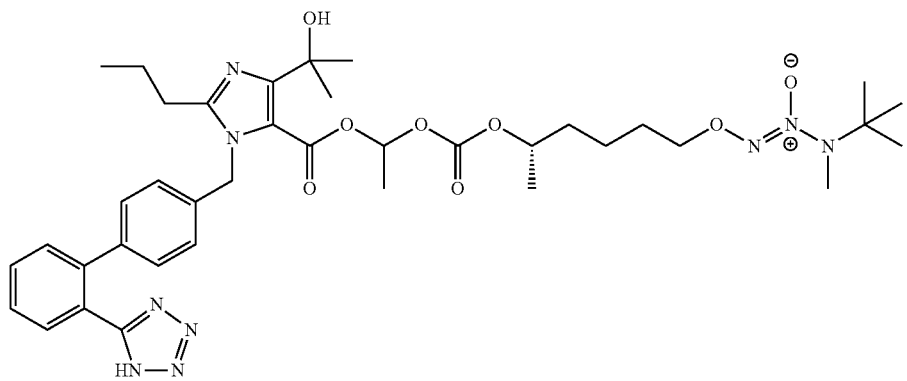

O²-[(5S)-5-({[1-({[4-(2-hydroxypropan-2-yl)-2-propyl-1-{[2'-(1H-tetrazol-5-yl)biphenyl-4-yl]methyl}-1H-imidazol-5-yl]carbonyl}oxy)ethoxy]carbonyl}oxy)hexyl] 1-(N-tert-butylmethylamino)diazen-1-ium-1,2-diolate The title compound was prepared by following the procedure for example 42, except that the reagent 2-ethoxy-1-{[2'-(1-trityl-1H-tetrazol-5-yl)biphenyl-4-yl]methyl}-1H-benzimidazole-7-carboxylic acid was replaced by 4-(2-hydroxypropan-2-yl)-2-propyl-1-{[2'-(1-trityl-1H-tetrazol-5-yl)biphenyl-4-yl]methyl}-1H-imidazole-5-carboxylic acid. ¹H NMR (500 MHz, CDCl₃) δ 0.95 (t, J=7.4 Hz, 3H), 1.16 (d, J=4.3 Hz, 3H, D1), 1.17 (d, J=4.3, Hz, 3H, D2), 1.20 (s, 9H), 1.26-1.35 (m, 2H), 1.43 (d, J=5.3 Hz, 3H, D1), 1.46 (d, J=5.3 Hz, 3H, D2), 1.50-1.60 (m, 8H), 1.65 (quintet, J=7.6 Hz, 2H), 1.71 (sextet, J=7.5 Hz, 2H), 2.58 (q, J=6.4 Hz, 2H), 2.78 (s, 3H), 4.14 (t, J=6.6 Hz, 2H, D1), 4.17 (t, J=6.6 Hz, 2H, D2), 4.64 (sextet, J=6.3 Hz, 1H), 5.41 (d, J=3.5 Hz, 2H), 6.83-6.88 (m, 3H), 7.11 (t, J=8.0 Hz, 2H), 7.44 (d, J=7.5 Hz, 1H), 7.48-7.54 (m, 1H), 7.59 (t, J=7.5 Hz, 1H), 7.90 (dd, J=5.7, 6.7 Hz, 1H); LC-MS (M+H) found 764.5.

Example 45

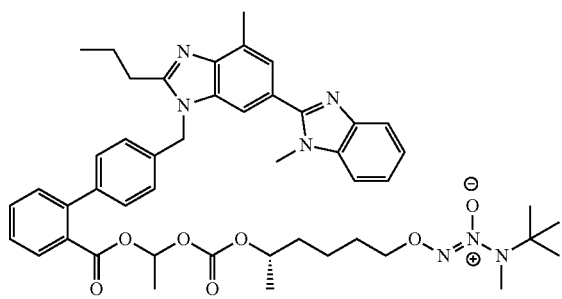

O²-{(5S)-5-[({1-[({4'-[(1,7'-dimethyl-2'-propyl-1H,3'H-2,5'-bibenzimidazol-3=40 yl)methyl]biphenyl-2-yl}carbonyl)oxy]ethoxy}carbonyl)oxy]hexyl} 1-(N-tert-butylmethylamino)diazen-1-ium-1,2-diolate The title compound was prepared by following the procedure for example 42, except that the reagent 2-ethoxy-1-{[2'-(1-trityl-1H-tetrazol-5-yl)biphenyl-4-yl]methyl}-1H-benzimidazole-7-carboxylic acid was replaced by 4'-[(1,7'-dimethyl-2'-propyl-1H,3'H-2,5'-bibenzimidazol-3'-yl)methyl]biphenyl-2-carboxylic acid. Chromatography of the diastereomeric mixture over Chiralpak AD-H column, eluting with isopropanol/carbon dioxide, afforded the two separate diastereomers.

Diastereomer A: ¹H NMR (500 MHz, CDCl₃) δ 1.07 (t, J=7.4 Hz, 3H), 1.20 (s, 9H), 1.25 (d, J=6.0 Hz, 3H), 1.25 (d, J=6.0 Hz, 3H), 1.32-1.46 (m, 2H), 1.59-1.69 (m, 2H), 1.74 (quintet, J=6.9 Hz, 2H), 1.89 (sextet, J=7.6 Hz, 2H), 2.77 (s, 3H), 2.78 (s, 3H), 2.94 (t, J=7.8 Hz, 2H), 3.80 (s, 3H), 4.20 (t, J=6.8 Hz, 2H), 4.72 (sextet, J=6.0 Hz, 1H), 5.45 (s, 2H), 6.71 (q, J=5.5 Hz, 1H), 7.09 (d, J=7.3 Hz, 2H), 7.25 (d, J=7.4 Hz, 2H), 7.26-7.31 (m, 3H), 7.34-7.38 (m, 1H), 7.41 (dt, J=1.3, 7.7 Hz, 1H), 7.45 (s, 1H), 7.47 (s, 1H), 7.51 (dt, J=1.3, 7.8 Hz, 1H), 7.79 (dd, J=3.4, 5.6 Hz, 1H), 7.86 (dd, J=1.2, 7.6 Hz, 1H); LC-MS (M+H) found 832.4.

Diastereomer B: ¹H NMR (500 MHz, CDCl₃) δ 1.07 (t, J=7.4 Hz, 3H), 1.22 (s, 9H), 1.23 (d, J=6.2 Hz, 3H), 1.29 (d, J=5.4 Hz, 3H), 1.34-1.46 (m, 2H), 1.60-1.69 (m, 2H), 1.74 (quintet, J=6.9 Hz, 2H), 1.89 (sextet, J=7.6 Hz, 2H), 2.77 (s, 3H), 2.80 (s, 3H), 2.94 (t, J=7.8 Hz, 2H), 3.80 (s, 3H), 4.23 (t, J=6.8 Hz, 2H), 4.72 (sextet, J=6.0 Hz, 1H), 5.45 (s, 2H), 6.72 (q, J=5.5 Hz, 1H), 7.09 (d, J=7.3 Hz, 2H), 7.25 (d, J=7.4 Hz, 21-1), 7.26-7.31 (m, 3H), 7.34_7.38 (m, 1H), 7.40 (dt, J=1.3, 7.7 Hz, 1H), 7.45 (s, 1H), 7.48 (s, 1H), 7.52 (dt, J=1.3, 7.8 Hz, 1H), 7.79 (dd, J=3.4, 5.6 Hz, 1H), 7.86 (dd, J=1.2, 7.6 Hz, 1H); LC-MS (M+H) found 832.4.

Example 46

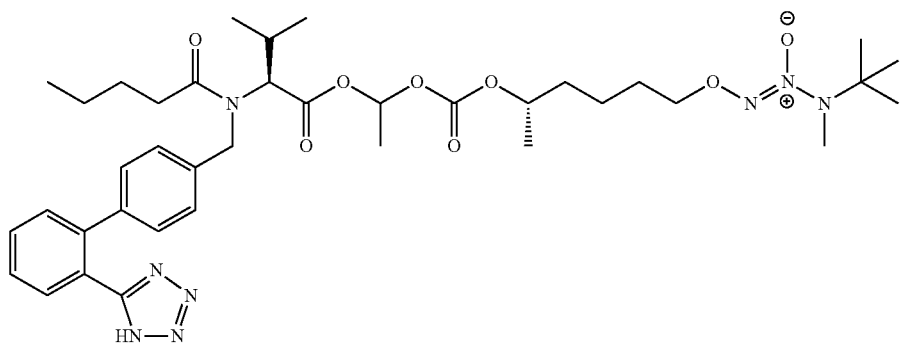

O²-{(5S)-5-[({1-[(N-pentanoyl-N-{[2'-(1H-tetrazol-5-yl)biphenyl-4-yl]methyl}-L-valyl)oxy]ethoxy}carbonyl)oxy]hexyl} 1-(N-tert-butylmethylamino)diazen-1-ium-1,2-diolate The title compound was prepared by following the procedure for example 42, except that the reagent 2-ethoxy-1-{[2'-(1-trityl-1H-tetrazol-5-yl)biphenyl-4-yl]methyl}-1H-benzimidazole-7-carboxylic acid was replaced by N-pentanoyl-N-{[2'-(1-trityl-1H-tetrazol-5-yl)biphenyl-4-yl]methyl}-L-valine. ¹H NMR (500 MHz, CDCl₃) δ 0.84-0.90 (m, 4H), 0.90-0.96 (m, 1H), 0.99 (dd, J=3.0, 8.3 Hz, 3H), 1.15-1.23 (m, 3H), 1.20 (s, 9H), 1.26-1.42 (m, 8H), 1.50-1.70 (m, 5H), 2.18-2.48 (m, 3H), 2.77 (s, 3H), 4.02-4.40 (m, 3H), 4.50-4.76 (m, 2H), 4.82-5.20 (m, 1H), 6.36-6.57 (m, 1H), 7.07 (dd, J=3.0, 8.2 Hz, 1H), 7.10-7.20 (m, 3H), 7.38-7.46 (m, 1H), 7.47-7.53 (m, 1H), 7.53-7.60 (m, 1H), 7.90-8.07 (m, 1H); LC-MS (M+H) found 753.5.

Example 47

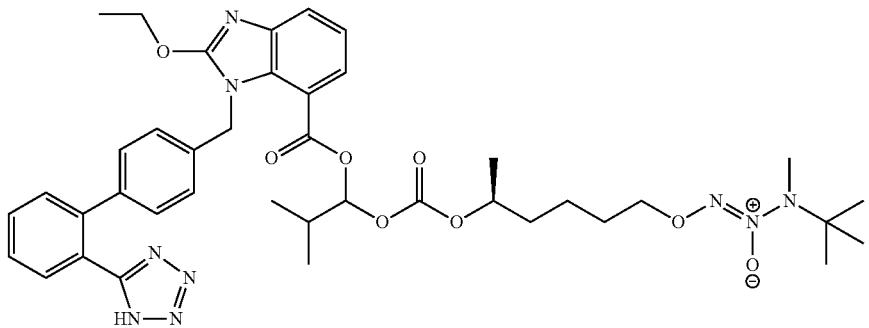

O²-[(5S)-5-{[(1-{[(2-ethoxy-1-{[2'-(1H-tetrazol-5-yl)biphenyl-4-yl]methyl}-1H-benzimidazol-7-yl)carbonyl]oxy}-2-methylpropoxy)carbonyl]oxy}hexyl] 1-(N-tert-butylmethylamino)diazen-1-ium-1,2-diolate The title compound was prepared by following the procedure for example 43, except that the reagent 1-chloroethyl chloroformate was replaced by 1-chloro-2-methylpropyl chloroformate. ¹H NMR (500 MHz, CDCl₃) δ 0.73-0.79 (m, 6H), 1.16-1.20 (m, 2H), 1.19 (s, 9H, D1), 1.21 (s, 9H), D2), 1.28-1.40 (m, 2H), 1.42 (t, J=7.1 Hz, 3H, D1), 1.42 (t, J=7.1 Hz, 3H, D2), 1.45-1.52 (m, 1H), 1.54-1.81 (m, 4H), 1.85-1.96 (m, 1H), 2.77 (s, 3H, D1), 2.79 (s, 3H, D2), 3.99-4.09 (m, 1H), 4.10-4.18 (m, 1H), 4.19 (t, J=6.8 Hz, 1H), 4.41-4.54 (m, 1H), 4.66 (sextet, J=5.9 Hz, 1H), 5.60 (d, J=16.8 Hz, 1H), 5.71 (d, J=16.8 Hz, 1H), 6.44 (d, J=5.2 Hz, 1H, D1), 6.44 (d, J=5.2 Hz, 1H, D2), 6.67-6.74 (m, 2H), 6.78-6.84 (m, 3H), 6.90 (d, J=8.0 Hz, 1H), 7.24-7.27 (m, 1H), 7.49 (t, J=6.9 Hz, 1H), 7.58 (dt, J=1.3, 6.0 Hz, 2H), 7.97 (dt, J=1.7, 5.5 Hz, 1H); LC-MS (M+H) found 786.4.

Example 48

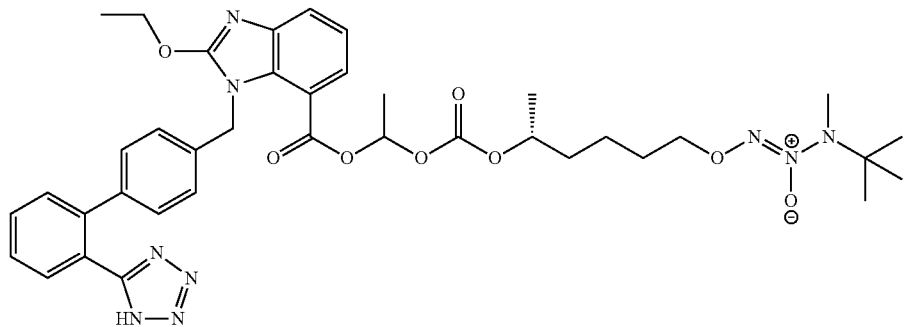

$O^2$-[(5R)-5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}hexyl] 1-(N-tert-butylmethylamino)diazen-1-ium-1,2-diolate The title compound was prepared by following the procedure for example 2, except that the reagent $O^2$-(3-hydroxypropyl) 1-(N,N-diethylamino)diazen-1-ium-1,2-diolate (intermediate 6) was replaced by $O^2$-[(5R)-5-hydroxyhexyl] 1-(N-tert-butylmethylamino)diazen-1-ium-1,2-diolate (intermediate 35).

Example 49

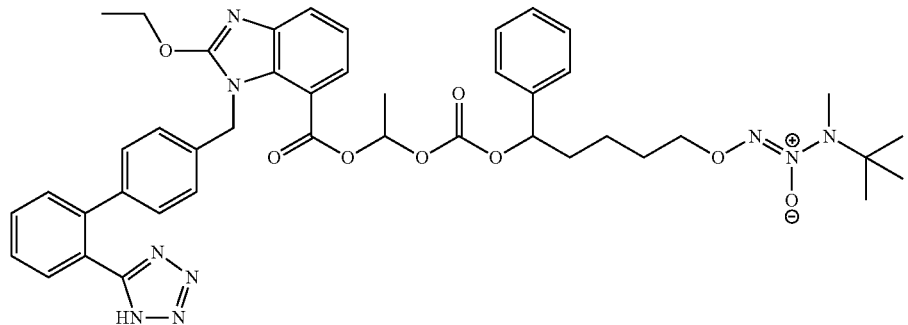

$O^2$-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}-5-phenylpentyl) 1-(N-tert-butylmethylamino)diazen-1-ium-1,2-diolate The title compound was prepared by following the procedure for example 2, except that the reagent $O^2$-(3-hydroxypropyl) 1-(N,N-diethylamino)diazen-1-ium-1,2-diolate (intermediate 6) was replaced by $O^2$-(5-hydroxy-5-phenylpentyl) 1-(N-tert-butylmethylamino)diazen-1-ium-1,2-diolate (intermediate 36). $^1$H NMR (500 MHz, CDCl$_3$) δ 1.20 (s, 9H), 1.44 (d, J=5.5 Hz, 3H), 1.45 (t, J=7.0 Hz, 3H), 1.56-1.76 (m, 4H), 1.82-1.96 (m, 2H), 2.76 (s, 3H), 4.12 (dt, J=2.5, 6.7 Hz, 2H), 4.40-4.49 (m, 1H), 4.51-4.61 (m, 1H), 5.39 (t, J=7.3 Hz, 1H), 5.57 (d, J=16.9 Hz, 1H), 5.70 (d, J=16.9 Hz, 1H), 6.68 (q, J=5.5 Hz, 1H), 6.85 (d, J=8.0 Hz, 2H), 6.95 (d, J=8.0 Hz, 2H), 7.07-7.14 (m, 3H), 7.17-7.22 (m, 3H), 7.36 (dd, J=1.8, 7.4 Hz, 1H), 7.38-7.42 (m, 1H), 7.54-7.60 (m, 3H), 7.99 (d, J=7.3 Hz, 1H); LC-MS (M+H) found 820.9.

Example 50

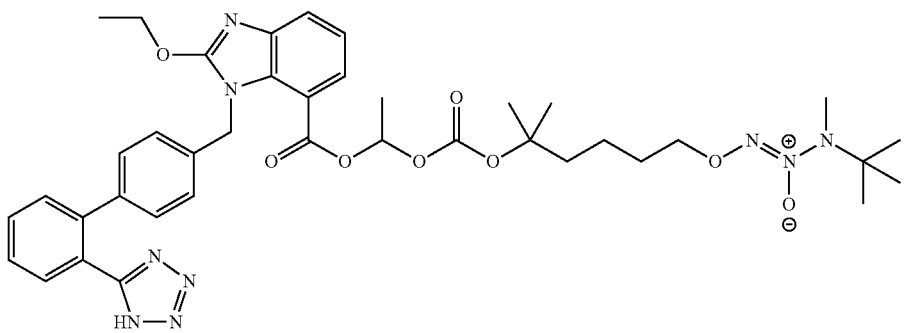

O²-(5-{[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}-5-methylhexyl) 1-(N-tert-butylmethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-(5-hydroxy-5-methylhexyl) 1-(N-tert-butylmethylamino)diazen-1-ium-1,2-diolate (intermediate 37). ¹H NMR (500 MHz, CDCl₃) δ 1.20 (s, 9H), 1.29 (d, J=5.0 Hz, 3H), 1.32-1.36 (m, 2H), 1.35 (s, 6H, D1), 1.35 (s, 6H, D2), 1.42 (t, J=7.1 Hz, 3H), 1.60-1.72 (m, 4H), 2.78 (s, 3H), 4.16 (t, J=6.8 Hz, 2H), 4.18-4.24 (m, 1H), 4.45-4.51 (m, 1H), 5.58 (d, J=17.1 Hz, 1H), 5.62 (d, J=16.9 Hz, 1H), 6.64 (q, J=5.3 Hz, 1H), 6.77 (d, J=7.6 Hz, 2H), 6.87 (d, J=8.2 Hz, 2H), 6.95 (t, J=8.0 Hz, 1H), 6.98-7.06 (m, 1H), 7.28-7.31 (m, 1H), 7.47 (d, J=8.3 Hz, 1H), 7.55-7.58 (m, 2H), 7.97 (dd, J=3.4, 6.4 Hz, 1H); LC-MS (M+H) found 772.9.

Example 51

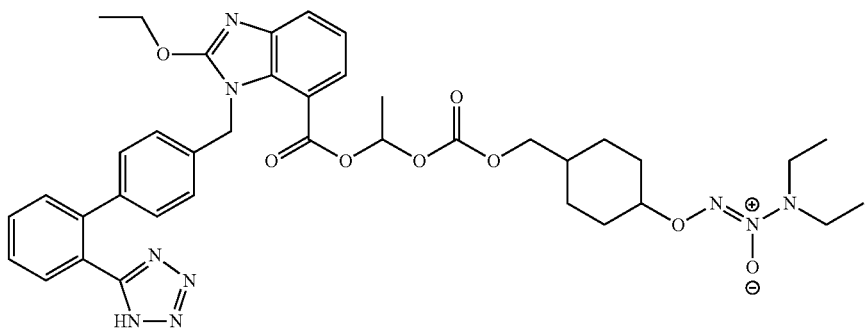

O²-[4-({[(1-{[(2-ethoxy-1-{[2'-(1H-tetrazol-5-yl)biphenyl-4-yl]methyl}-1H-benzimidazol-7-yl)carbonyl]oxy}ethoxy)carbonyl]oxy}methyl)cyclohexyl] 1-(N,N-diethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-[4-(hydroxymethyl)cyclohexyl] 1-(N,N-diethylamino)diazen-1-ium-1,2-diolate (intermediate 38). ¹H NMR (500 MHz, CDCl₃) δ 0.93-1.02 (m, 2H), 1.08 (t, J=7.1 Hz, 6H), 1.34-1.44 (m, 2H), 1.45 (t, J=7.1 Hz, 3H), 1.50 (d, J=5.5 Hz, 3H), 1.60-1.70 (m, 1H), 1.72-1.77 (m, 2H), 2.05-2.12 (m, 2H), 3.07 (q, J=7.1 Hz, 4H), 3.88 (d, J=5.9 Hz, 2H), 4.10-4.18 (m, 1H), 4.42-4.50 (m, 1H), 4.51-4.59 (m, 1H), 5.59 (d, J=16.7 Hz, 1H), 5.72 (d, J=16.9 Hz, 1H), 6.78 (q, J=5.5 Hz, 1H), 6.89 (d, J=7.6 Hz, 2H), 6.98 (d, J=8.2 Hz, 2H), 7.09 (t, J=7.8 Hz, 1H), 7.35 (dd, J=2.0, 6.9 Hz, 1H), 7.38-7.46 (m, 1H), 7.52-7.58 (m, 2H), 7.59 (d, J=7.3 Hz, 1H), 8.02 (dd, J=2.1, 6.9 Hz, 1H); LC-MS (M+H) found 756.8.

Example 52

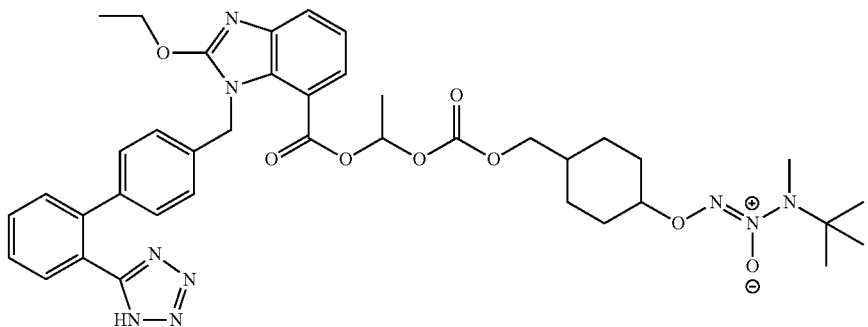

O²-[4-({[(1-{[(2-ethoxy-1-{[2'-(1H-tetrazol-5-yl) biphenyl-4-yl]methyl}-1H-benzimidazol-7-yl)carbonyl]oxy}ethoxy)carbonyl]oxy}methyl)cyclohexyl] 1-(N-tert-butylmethylamino)diazen-1-ium-1,2-diolate The title compound was prepared by following the procedure for example 2, except that the reagent O²-(3-hydroxypropyl) 1-(N,N-diethylamino)diazen-1-ium-1,2-diolate (intermediate 6) was replaced by O²-[4-(hydroxymethyl)cyclohexyl] 1-(N-tert-butylmethylamino)diazen-1-ium-1,2-diolate (intermediate 39). $^1$H NMR (500 MHz, CDCl$_3$) δ 0.93-1.02 (m, 2H), 1.23 (s, 9H), 1.34-1.44 (m, 2H), 1.45 (t, J=7.1 Hz, 3H), 1.50 (d, J=5.5 Hz, 3H), 1.60-1.70 (m, 1H), 1.72-1.77 (m, 2H), 2.05-2.12 (m, 2H), 2.80 (s, 3H), 3.88 (d, J=5.9 Hz, 2H), 4.10-4.18 (m, 1H), 4.42-4.50 (m, 1H), 4.51-4.59 (m, 1H), 5.59 (d, J=16.7 Hz, 1H), 5.72 (d, J=16.9 Hz, 1H), 6.78 (q, J=5.5 Hz, 1H), 6.89 (d, J=7.6 Hz, 2H), 6.98 (d, J=8.2 Hz, 2H), 7.09 (t, J=7.8 Hz, 1H), 7.35 (dd, J=2.0, 6.9 Hz, 1H), 7.38-7.46 (m, 1H), 7.52-7.58 (m, 2H), 7.59 (d, J=7.3 Hz, 1H), 8.02 (dd, J=2.1, 6.9 Hz, 1H); LC-MS (M+H) found 770.9.

Example 53

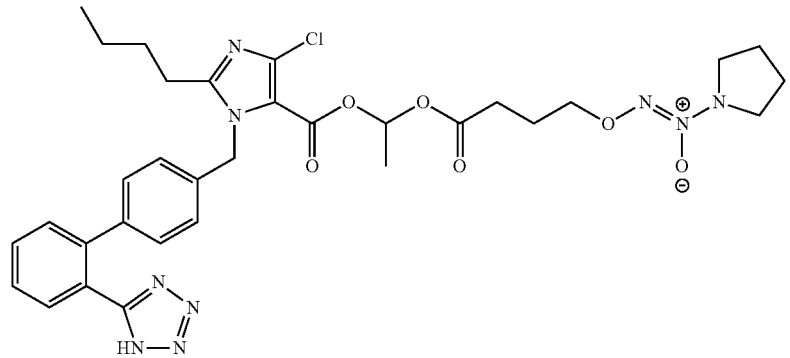

O²-[4-(1-{[(2-butyl-4-chloro-1-{[2'-(1H-tetrazol-5-yl)biphenyl-4-yl]methyl}-1H-imidazol-5-yl)carbonyl]oxy}ethoxy)-4-oxobutyl] 1-(pyrrolidin-1-yl)diazen-1-ium-1,2-diolate Step A: O²-{4-oxo-4-[1-(phenylthio)ethoxy]butyl} 1-(pyrrolidin-1-yl)diazen-1-ium-1,2-diolate To a N,N-dimethylformamide (5 mL) solution of O²-[3-(carboxylato)propyl] 1-(pyrrolidin-1-yl)diazen-1-ium-1,2-diolate (intermediate 41, 483 mg, 2.23 mmol) and potassium tert-butoxide (358 mg, 3.19 mmol) at room temperature was added 1-chloroethyl phenyl sulfide (4.0 mL, 5.9 mmol, prepared as described in Benneche, T.; Strande, P.; Wiggen, U. *Acta Chem. Scand.* 1989, 43, 74-77.). After 16 hours, the reaction mixture was purified by column chromatography on silica gel, eluting with 7/93→60/40 ethyl acetate/hexanes to give the title compound as a colorless liquid. $^1$H NMR (500 MHz, CDCl$_3$) δ 1.50 (d, J=6.5 Hz, 3H), 1.90-1.95 (m, 4H), 1.95-2.05 (m, 2H), 2.45 (t, J=6.4 Hz, 2H), 3.45-3.55 (m, 4H), 4.15 (t, J=6.4 Hz, 2H), 6.21 (q, J=6.4 Hz, 1H), 7.25-7.35 (m, 3H), 7.40-7.50 (m, 2H).

Step B: O²-[4-(1-chloroethoxy)-4-oxobutyl] 1-(pyrrolidin-1-yl)diazen-1-ium-1,2-diolate To a dichloromethane (1 mL) solution of O²-{4-oxo-4-[1-(phenylthio)ethoxy]butyl} 1-(pyrrolidin-1-yl)diazen-1-ium-1,2-diolate (246 mg, 0.697 mmol) was added a 1.0 M dichloromethane solution of sulfuryl chloride (1.5 mL, 1.50 mmol) at room temperature. After 3 hours, the reaction was concentrated in vacuo, and the residue was purified by column chromatography on silica gel, eluting with 7/93→60/40 ethyl acetate/hexanes to give the title compound as a colorless liquid. $^1$H NMR (500 MHz, CDCl$_3$) δ 1.78 (d, J=5.7 Hz, 3H), 1.94 (m, 4H), 2.05-2.15 (m, 2H), 2.50 (t, J=7.4 Hz, 2H), 3.45-3.60 (m, 4H), 4.15-4.25 (m, 2H), 6.53 J=6.0 Hz, 1H).

Step C: O²-[4-(1-{[(2-butyl-4-chloro-1-{[2'-(1-trityl-1H-tetrazol-5-yl)biphenyl-4-yl]methyl}-1H-imidazol-5-yl)carbonyl]oxy}ethoxy)-4-oxobutyl] 1-(pyrrolidin-1-yl)diazen-1-ium-1,2-diolate The title compound was prepared by following step B in example 1, except that the reagent O²-(3-{[(1-chloroethoxy)carbonyl]oxy}propyl) 1-(N,N-diethylamino)diazen-1-ium-1,2-diolate was replaced by O²-[4-(1-chloroethoxy)-4-oxobutyl] 1-(pyrrolidin-1-yl)diazen-1-ium-1,2-diolate. $^1$H NMR (500 MHz, CDCl$_3$) δ 0.88 (t, J=7.4 Hz, 3H), 1.34 (sextet, J=7.6 Hz, 2H), 1.58 (d, J=5.5 Hz, 3H), 1.66-1.74 (m, 2H), 1.86-1.93 (m, 4H), 1.95-2.05 (m, 2H), 2.35 (t, J=7.3 Hz, 2H), 2.61 (t, J=6.9 Hz, 2H), 3.40-3.50 (m, 4H), 4.09 (t, J=6.2 Hz, 2H), 5.22 (d, J=16.7 Hz, 1H), 5.88 (d, J=16.5 Hz, 1H), 6.79 (d, J=8.0 Hz, 2H), 6.86 (q, J=5.5 Hz, 1H), 6.92 (d, J=7.8 Hz, 6H), 7.09 (d, J=8.2 Hz, 2H), 7.25 (t, J=7.8 Hz, 6H), 7.31-7.35 (m, 4H), 7.43-7.50 (m, 2H), 7.90 (d, J=7.7 Hz, 1H); LC-MS (M+H) found 922.2.

Step D: O²-[4-(1-{[(2-butyl-4-chloro-1-{[2'-(1H-tetrazol-5-yl)biphenyl-4-yl]methyl}-1H-imidazol-5-yl)carbonyl]oxy}ethoxy)-4-oxobutyl] 1-(pyrrolidin-1-yl)diazen-1-ium-1,2-diolate The title compound was prepared by following step C in example 1, except that the reagent O²-(3-{[(1-{[(2-butyl-4-chloro-1-{[2'-(1-trityl-1H-tetrazol-5-yl)biphenyl-4-yl]methyl}-1H-imidazol-5-yl)carbonyl]oxy}ethoxy)carbonyl]oxy}propyl) 1-(N,N-diethylamino)diazen-1-ium-1,2-diolate was replaced by O²-[4-(1-{[(2-butyl-4-chloro-1-{[2'-(1-trityl-1H-tetrazol-5-yl)biphenyl-4-yl]methyl}-1H-imidazol-5-yl)carbonyl]oxy}ethoxy)-4-oxobutyl] 1-(pyrrolidin-1-yl)diazen-1-ium-1,2-diolate. ¹H NMR (500 MHz, CDCl₃) δ 0.88 (t, J=7.4 Hz, 3H), 1.34 (sextet, J=7.6 Hz, 2H), 1.58 (d, J=5.5 Hz, 3H), 1.68-1.72 (m, 2H), 1.86-1.93 (m, 4H), 1.95-2.05 (m, 2H), 2.35 (t, J=7.3 Hz, 2H), 2.61 (t, J=6.9 Hz, 2H), 3.40-3.50 (m, 4H), 4.09 (t, J=6.2 Hz, 2H), 5.22 (d, J=16.7 Hz, 1H), 5.88 (d, J=16.5 Hz, 1H), 6.86 (d, J=8.1 Hz, 2H), 6.98 (q, J=5.5 Hz, 1H), 7.12 (d, J=8.0 Hz, 2H), 7.4 (d, J=7.6 Hz, 1H), 7.50 (t, J=7.6 Hz, 1H), 7.57 (t, J=7.8 Hz, 1H), 7.87 (d, J=7.7 Hz, 1H); LC-MS (M+H) found 680.1.

Example 54

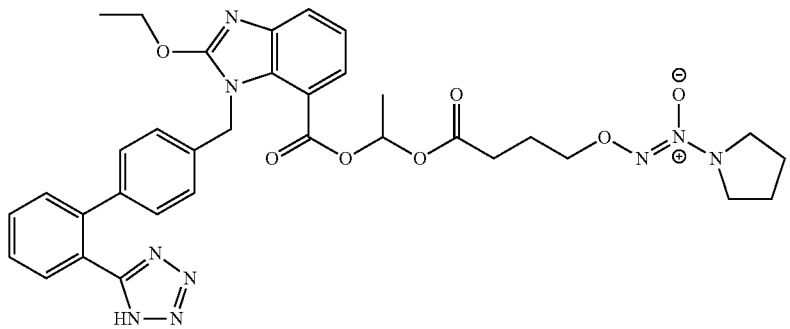

O²-[4-(1-{[(2-ethoxy-1-{[2'-(1H-tetrazol-5-yl)biphenyl-4-yl]methyl}-1H-benzimidazol-7-yl)carbonyl]oxy}ethoxy)-4-oxobutyl] 1-(pyrrolidin-1-yl)diazen-1-ium-1,2-diolate The title compound was prepared by following the procedure for example 53, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. ¹H NMR (500 MHz, CDCl₃) δ 1.46 (t, J=7.0 Hz, 3H), 1.52 (d, J=5.5 Hz, 3H), 1.86-1.93 (m, 4H), 1.95-2.10 (m, 2H), 2.35 (t, J=7.3 Hz, 2H), 3.49 (t, J=6.6 Hz, 4H), 4.09 (t, J=6.2 Hz, 2H), 4.40-4.43 (m, 1H), 4.52-4.56 (m, 1H), 5.54 (d, J=16.4 Hz, 1H), 5.71 (d, J=16.4 Hz, 1H), 6.81 (q, J=5.5 Hz, 1H), 6.91 (d, J=8.0 Hz, 2H), 6.97 (d, J=8.3 Hz, 2H), 7.09 (t, J=8.0 Hz, 1H), 7.34 (dd, J=1.8, 7.3 Hz, 1H), 7.42-7.59 (m, 4H), 7.97 (dd, J=2.0, 7.4 Hz, 1H); LC-MS (M+H) found 684.1.

Example 55

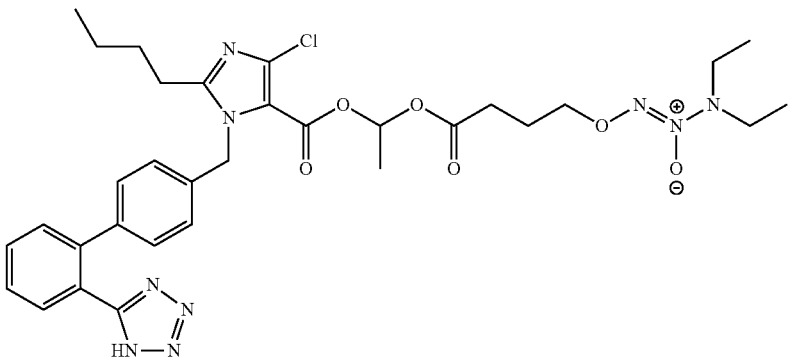

O²-[4-(1-{[2-butyl-4-chloro-1-{[2'-(1H-tetrazol-5-yl)biphenyl-4-yl]methyl}-1H-imidazol-5-yl)carbonyl]oxy}ethoxy)-4-oxobutyl] 1-(N,N-diethylamino)diazen-1-ium-1,2-diolate The title compound was prepared by following the procedure for example 53, except that the reagent O²-[3-(carboxylato)propyl] 1-(pyrrolidin-1-yl)diazen-1-ium-1,2-diolate (intermediate 41) was replaced by O²-[3-(carboxylato)propyl] 1-(N,N-diethylamino)diazen-1-ium-1,2-diolate (intermediate 40). ¹H NMR (500 MHz, CDCl₃) δ 0.88 (t, J=7.3 Hz, 3H), 1.08 (t, J=7.1 Hz, 6H), 1.38 (sextet, J=7.5 Hz, 2H), 1.58 (d, J=5.5 Hz, 3H), 1.75 (m, 2H), 2.03 (quintet, J=6.4 Hz, 2H), 2.35 (t, J=7.0 Hz, 2H), 2.62 (t, J=7.6 Hz, 2H), 3.09 (q, J=7.3 Hz, 4H), 4.26 (t, J=6.4 Hz, 2H), 5.22 (d, J=16.7 Hz, 1H), 5.88 (d, J=16.5 Hz, 1H), 6.86 (d, J=8.1 Hz, 2H), 6.98 (q, J=5.5 Hz, 1H), 7.09 (d, J=8.2 Hz, 2H), 7.40 (d, J=7.6 Hz, 1H), 7.50 (t, J=7.6 Hz, 1H), 7.57 (t, J=7.8 Hz, 1H), 7.90 (d, J=7.7 Hz, 1H); LC-MS (M+H) found 682.1.

Example 56

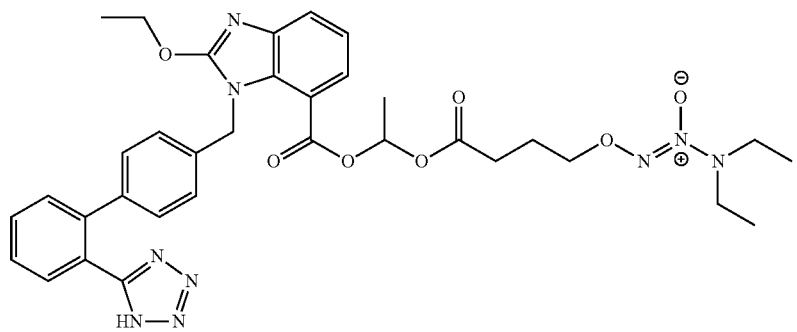

O²-[4-(1-{[(2-ethoxy-1-{[2'-(1H-tetrazol-5-yl)biphenyl-4-yl]methyl}-1H-benzimidazol-7-yl)carbonyl]oxy}ethoxy)-4-oxobutyl] 1-(N,N-diethylamino)diazen-1-ium-1,2-diolate The title compound was prepared by following the procedure for example 55, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. ¹H NMR (500 MHz, CDCl₃) δ 1.03 (t, J=7.1 Hz, 6H), 1.44 (d, J=5.5 Hz, 3H), 1.45 (t, J=7.1 Hz, 3H), 1.98 (quintet, J=6.9 Hz, 2H), 2.35 (dt, J=2.3, 7.5 Hz, 2H), 3.08 (q, J=7.1 Hz, 4H), 4.21 (t, J=6.2 Hz, 2H), 4.40-4.50 (m, 1H), 4.50-4.58 (m, 1H), 5.52 (d, J=16.5 Hz, 1H), 5.74 (d, J=16.2 Hz, 1H), 6.87-6.92 (m, 3H), 6.97 (d, J=8.2 Hz, 2H), 7.08 (t, J=7.8 Hz, 1H), 7.35 (dd, J=1.3, 7.5 Hz, 1H), 7.36-7.43 (m, 1H), 7.49-7.58 (m, 3H), 7.93 (d, J=7.3 Hz, 1H); LC-MS (M+H) found 686.2.

Example 57

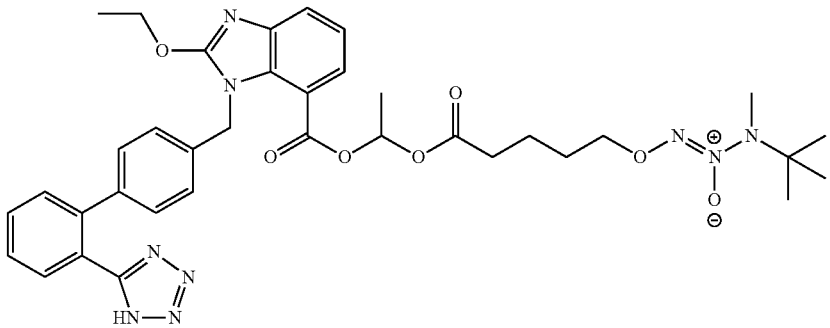

O²-[5-(1-{[(2-ethoxy-1-{[2'-(1H-tetrazol-5-yl)biphe-nyl-4-yl]methyl}-1H-benzimidazol-7-yl)carbonyl]oxy}ethoxy)-5-oxopentyl] 1-(N-tert-butylmethy-lamino)diazen-1-ium-1,2-diolate The title compound was prepared by following the procedure for example 54, except that the reagent O²-[3-(carboxylato)propyl] 1-(pyrrolidin-1-yl)diazen-1-ium-1,2-diolate (intermediate 41) was replaced by O²-[4-(carboxylato)butyl] 1-(N-tert-butylmethylamino)diazen-1-ium-1,2-diolate (intermediate 42). ¹H NMR (500 MHz, CDCl₃) δ 1.19 (s, 9H), 1.30-1.35 (m, 3H), 1.42 (t, J=7.0 Hz, 3H), 1.57-1.70 (m, 4H), 2.20-2.29 (m, 2H), 2.76 (s, 3H), 4.14 (t, J=5.5 Hz, 2H), 4.21-4.32 (m, 1H), 4.41-4.50 (m, 1H), 5.54 (d, J=17.0 Hz, 1H), 5.69 (d, J=17.0 Hz, 1H), 6.74-6.83 (m, 3H), 6.88 (d, J=7.0 Hz, 2H), 6.97 (t, J=7.0 Hz, 1H), 7.04-7.14 (m, 1H), 7.27-7.33 (m, 1H), 7.48 (d, J=7.5 Hz, 1H), 7.51-7.58 (m, 2H), 7.90-7.95 (m, 1H); LC-MS (M+H) found 714.5.

Vessel Relaxation

The ability of the compounds to induce vasorelaxation was tested in vitro in isolated rabbit thoracic aorta preparations (Wanstall J. C. et al., Br. J. Pharmacol., 134:463-472, 2001). Male New Zealand rabbits were anaesthetized with thiopental-Na (50 mg/kg, iv), sacrificed by exsanguinations and then the thorax was opened and the aorta dissected. Aortic ring preparations (4 mm in length) were set up in physiological salt solution (PSS) at 37° C. in small organ chambers (5 ml). The composition of PSS was (mM): NaCl 130, NaHCO₃ 14.9, KH₂PO₄ 1.2, MgSO₄ 1.2, HEPES 10, CaCl₂, ascorbic acid 170 and glucose 1.1 (95% O₂/5% CO₂; pH 7.4). Each ring was mounted under 2 g passive tension. Isometric tension was recorded with a Grass transducer (Grass FT03) attached to a BIOPAC MP150 System. Preparations were allowed to equilibrate for 1 h, and then contracted submaximally with noradrenaline (NA, 1 µM) and, when the contraction was stable, acetylcholine (ACh, 10 µM) was added. A relaxant response to ACh indicated the presence of a functional endothelium. Vessels that were unable to contract NA or showed no relaxation to ACh were discarded. When a stable precontraction was reached, a cumulative concentration-response curve to either of the vasorelaxant agents was obtained in the presence of a functional endothelium. Each arterial ring was exposed to only one combination of inhibitor and vasorelaxant. Moreover, the effect of the soluble guanylyl cyclase inhibitor ODQ (1-H-(1,2,4)-oxadiazol(4,3-a)quinoxalin-1-one) on vasorelaxation elicited by the compounds was examined preincubating the aortic rings with ODQ (10 µM) for 20 min.

Examples 32 and 48 were evaluated for vessel relaxation. In vitro, tissue-based measure of vessel relaxation, determined in rabbit aortic slices, demonstrated vessel relaxation according to the indicated EC₅₀ (molar concentration of compound which produces 50% of the maximum possible response for that compound—Data Table 1).

Data Table 1

|  | EC₅₀ in vessel relaxation assay |
| --- | --- |
| Example 32 | 46 µM |
| Example 48 | >100 µM |

What is claimed is:
1. A compound having the general formula:

wherein R is selected from the group consisting of

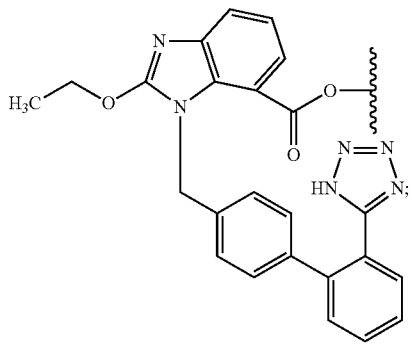

Y is

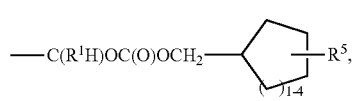

and
2) —C(R¹H)OC(O)X((CR¹²R¹³)—(CHR¹⁰)ₘ(CH₂)ₙ—Zₚ—(CH₂)_q—(CHR¹¹)ᵣ—(CR¹⁶R¹⁷))—R⁵;

Z is —O— or —(CR¹⁴R¹⁵)—;

m, n, p, q, and r are independently selected from the group consisting of 0 and 1;

X is —O— or —(CR¹⁸R¹⁹)—;

R¹ is selected from the group consisting of hydrogen, C₁₋₄ alkyl, aryl, C₁₋₄ alkylarylene, and arylC₁₋₄ alkylene;

R⁵ is —O—N=N(O)—NR³R⁴;

R³ and R⁴ are independently selected from the group consisting of unsubstituted or substituted C₁₋₆ alkyl, unsubstituted or substituted C₁₋₆ alkenyl, unsubstituted or substituted morpholino, amino, unsubstituted or substituted benzyl, unsubstituted or substituted phenyl, unsubstituted or substituted arylC₁₋₄ alkyl, or R³ and R⁴ together with the nitrogen atom to which they are attached, form a ring selected from the group consisting of

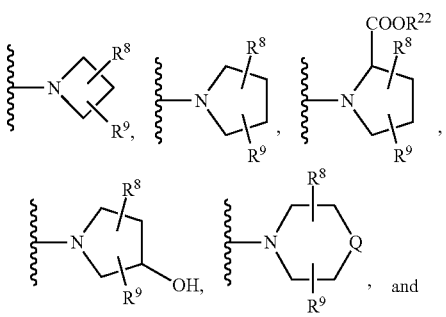

-continued

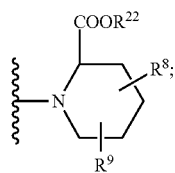

Q is selected from the group consisting of —(CR²OR²¹)—, —S—, —N(R⁶)— and —O—;

R⁶ is selected from the group consisting of hydrogen, unsubstituted or substituted $C_{1-6}$ alkyl, and —COOR²²;

R⁸, R⁹ and R²² are independently selected from the group consisting of hydrogen and unsubstituted or substituted $C_{1-6}$ alkyl;

R¹⁰ and R¹¹ are independently selected from the group consisting of hydrogen and unsubstituted or substituted $C_{1-6}$ alkyl;

R¹², R¹³, R¹⁴, R¹⁵, R¹⁶, R¹⁷, R¹⁸, R¹⁹, R²⁰ and R²¹ are independently selected from the group consisting of hydrogen, unsubstituted or substituted $C_{1-6}$ alkyl, and unsubstituted or substituted aryl;

or a stereoisomer thereof, or a pharmaceutically acceptable salt thereof, or a pharmaceutically acceptable salt of the stereoisomer thereof.

2. A compound of claim 1, or a pharmaceutically acceptable salt thereof, wherein R¹ is selected from the group consisting of CH₃ and CH(CH₃)₂.

3. A compound of claim 1, or a pharmaceutically acceptable salt thereof, wherein R¹⁰ and R¹¹ are independently selected from the group consisting of hydrogen and CH₃.

4. A compound of claim 1, or a pharmaceutically acceptable salt thereof, wherein R¹², R¹⁴, and R¹⁶ are independently selected from the group consisting of hydrogen, CH₃, and —C₆H₅.

5. A compound of claim 1, or a pharmaceutically acceptable salt thereof, wherein R¹³, R¹⁵ and R¹⁷ are independently selected from the group consisting of hydrogen and CH₃.

6. A compound of claim 1, or a pharmaceutically acceptable salt thereof, wherein R¹⁸, R¹⁹, R²⁰, and R²¹ are hydrogen.

7. A compound of claim 1, or a pharmaceutically acceptable salt thereof, wherein p is 1 and m, n, q, and r are 0.

8. A compound of claim 1, or a pharmaceutically acceptable salt thereof, wherein m, p and r are 1 and n and q are 0.

9. A compound of claim 1, or a pharmaceutically acceptable salt thereof, wherein m, n, p, q and r are 1.

10. A compound of claim 1, or a pharmaceutically acceptable salt thereof, wherein Z is selected from the group consisting of —O—, —(CH₂)—, —CH(CH₃)—, —CH(C₆H₅)—, and —(C(CH₃)₂)—.

11. A compound of claim 1, or a pharmaceutically acceptable salt thereof, wherein R³ is —CH₂CH₃ or —CH₃, and R⁴ is —CH₂CH₃, —C(CH₃)₃, —CH(CH₃)₂, or a cyclohexyl ring, or R³ and R⁴ together with the nitrogen atom to which they are attached form a ring selected from the group consisting of

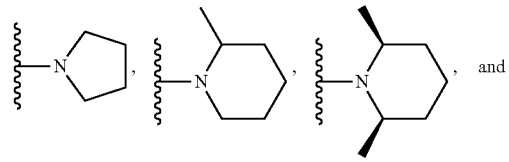

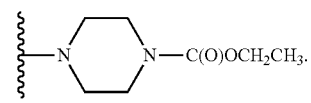

12. A compound of claim 1, or a pharmaceutically acceptable salt thereof, wherein R is selected from the group consisting of

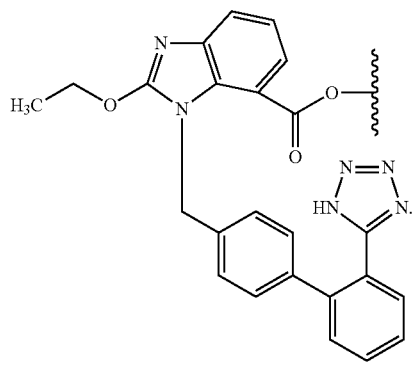

13. A compound of claim 1, wherein R⁵ is selected from the group consisting of

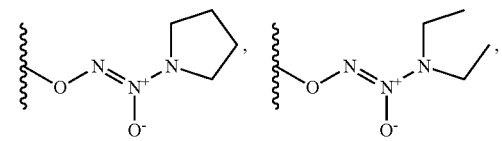

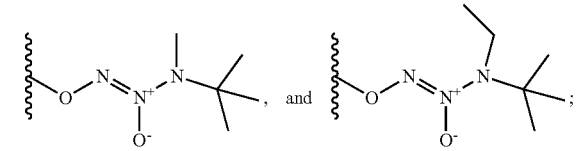

or a pharmaceutically acceptable salt thereof.

14. A compound of claim 1, listed in Compound Table

COMPOUND TABLE

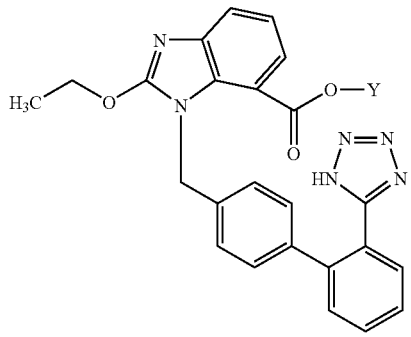

Y

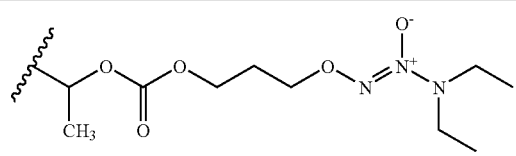

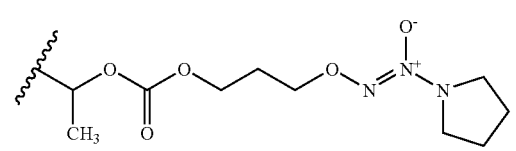

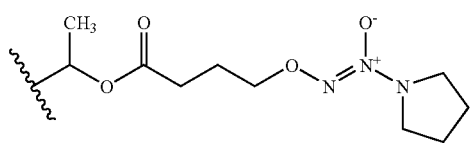

COMPOUND TABLE-continued

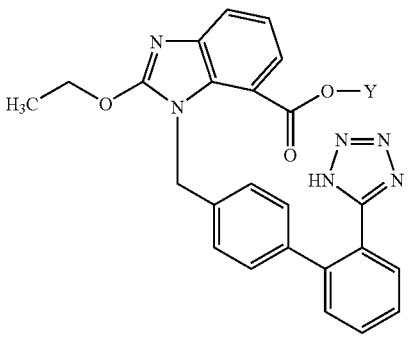

Y

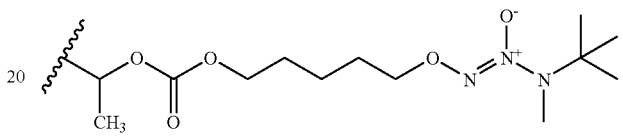

or a pharmaceutically acceptable salt thereof.

15. A compound of claim 1, or a pharmaceutically acceptable salt thereof, wherein Y is
—C(R$^1$H)OC(O)X((CR$^{12}$R$^{13}$)—(CHR$^{10}$)$_m$(CH$_2$)$_n$—Z$_p$—(CH$_2$)$_q$—(CHR$^{11}$)$_r$—(CR$^{16}$R$^{17}$))—R$^5$.

16. A pharmaceutical composition comprising a compound of claim 1 and a pharmaceutically acceptable carrier.

17. A pharmaceutical composition comprising a compound of claim 1, a diuretic, and a pharmaceutically acceptable carrier.

18. A method for treating hypertension in a patient which comprises administering to the patient a therapeutically effective amount of the composition of claim 16.

* * * * *